US012667716B2

(12) United States Patent　　(10) Patent No.:　US 12,667,716 B2
Fisher et al.　　　　　　　　　　(45) Date of Patent:　　Jun. 30, 2026

(54) VACUUM-ASSISTED ELECTROPORATION DEVICES, AND RELATED SYSTEMS AND METHODS

(71) Applicant: Inovio Pharmaceuticals Inc, Plymouth Meeting, PA (US)

(72) Inventors: Paul Fisher, Fallbrook, CA (US); Andrea Kemme, San Diego, CA (US); Eric Schade, San Diego, CA (US); Jay McCoy, Temecula, CA (US); Kate Broderick, San Diego, CA (US); Alison A. Generotti, Ocean City, NJ (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 600 days.

(21) Appl. No.: 17/207,545

(22) Filed: Mar. 19, 2021

(65) Prior Publication Data

US 2021/0290941 A1　Sep. 23, 2021

Related U.S. Application Data

(60) Provisional application No. 62/992,513, filed on Mar. 20, 2020.

(51) Int. Cl.
*A61N 1/04*　　　(2006.01)
*A61B 18/00*　　　(2006.01)
(Continued)

(52) U.S. Cl.
CPC ........... *A61N 1/0412* (2013.01); *A61M 37/00* (2013.01); *A61N 1/0476* (2013.01); *A61N 1/327* (2013.01); *A61M 2037/0007* (2013.01)

(58) Field of Classification Search
CPC .... A61N 1/327; A61N 1/0412; A61N 1/0476; A61N 1/0428; A61N 1/0432; A61N 1/30;
(Continued)

(56) References Cited

U.S. PATENT DOCUMENTS 6,022,316 A　　2/2000　Eppstein et al.
6,406,456 B1　　6/2002　Slate et al.
(Continued)

FOREIGN PATENT DOCUMENTS

CN　　　　103687644 A　　3/2014
CO　　　20220017706　　12/2022
(Continued)

OTHER PUBLICATIONS

ISA/220—Notification of Transmittal or Search Report and Written Opinion of the ISA, or the Declaration Mailed on Jun. 4, 2021 for WO Application No. PCT/US21/023344.
(Continued)

*Primary Examiner* — Chelsea E Stinson
*Assistant Examiner* — Hamza A Darb
(74) *Attorney, Agent, or Firm* — BakerHostetler

(57)　　　　　　　ABSTRACT

A device for vacuum-assisted in vivo electroporation of tissue includes a housing that defines a chamber and at least one opening into the chamber. A port extends through the housing, is remote from the at least one opening, and is connectable to a vacuum source. The port is configured to communicate vacuum pressure from the vacuum source to the chamber. A plurality of electrodes are positioned within the chamber and are configured to deliver one or more electroporation pulses to a targeted portion of tissue extending through the opening and held in the chamber responsive to the vacuum pressure.

13 Claims, 43 Drawing Sheets
(24 of 43 Drawing Sheet(s) Filed in Color)

(51) Int. Cl.
| | |
|---|---|
| *A61M 5/30* | (2006.01) |
| *A61M 37/00* | (2006.01) |
| *A61N 1/32* | (2006.01) |

(58) Field of Classification Search
CPC . A61N 1/325; A61N 1/00; A61M 2037/0007; A61M 37/00
See application file for complete search history.

(56) References Cited

U.S. PATENT DOCUMENTS

| | | | |
|---|---|---|---|
| 6,743,211 B1 | 6/2004 | Prausnitz et al. | |
| 7,367,341 B2 | 5/2008 | Anderson et al. | |
| RE43,009 E | 12/2011 | Chornenky et al. | |
| 8,545,497 B2 | 10/2013 | Morrissey et al. | |
| 8,915,894 B1 | 12/2014 | Lonky et al. | |
| 9,452,285 B2 | 9/2016 | Draghia-Akli et al. | |
| 10,045,911 B2 | 8/2018 | Williamson et al. | |
| 2002/0099323 A1 | 7/2002 | Dev et al. | |
| 2003/0153960 A1* | 8/2003 | Chornenky | A61N 1/327 607/72 |
| 2004/0120964 A1 | 6/2004 | Mikszta et al. | |
| 2005/0137531 A1 | 6/2005 | Prausnitz et al. | |
| 2005/0215941 A1 | 9/2005 | Bernard et al. | |
| 2006/0036209 A1 | 2/2006 | Subramony et al. | |
| 2006/0084938 A1* | 4/2006 | Zhang | A61N 1/327 604/501 |
| 2006/0224192 A1 | 10/2006 | Dimmer et al. | |
| 2007/0021712 A1 | 1/2007 | Bernard et al. | |
| 2007/0179535 A1 | 8/2007 | Morrissey et al. | |
| 2008/0091135 A1 | 4/2008 | Draghia-Akli et al. | |
| 2008/0215039 A1 | 9/2008 | Slatkine et al. | |
| 2009/0137949 A1 | 5/2009 | Landau et al. | |
| 2009/0326489 A1 | 12/2009 | Kensy et al. | |
| 2010/0210994 A1 | 8/2010 | Zarif | |
| 2011/0009807 A1* | 1/2011 | Kjeken | C12N 15/87 604/501 |
| 2013/0066296 A1 | 3/2013 | Broderick et al. | |
| 2014/0277219 A1 | 9/2014 | Nanda | |
| 2015/0088050 A1* | 3/2015 | Chang | A61N 1/327 604/20 |
| 2015/0305930 A1 | 10/2015 | Myung et al. | |
| 2015/0328449 A1* | 11/2015 | Soden | A61B 17/00234 604/20 |
| 2016/0089527 A1 | 3/2016 | Buss | |
| 2017/0305930 A1 | 10/2017 | Morimoto et al. | |
| 2018/0028260 A1 | 2/2018 | Onik et al. | |
| 2018/0070880 A1 | 3/2018 | Trembly et al. | |
| 2018/0169399 A1 | 6/2018 | Housley et al. | |
| 2018/0236225 A1 | 8/2018 | Broderick et al. | |
| 2018/0311497 A1 | 11/2018 | Viswanathan et al. | |
| 2018/0339090 A1 | 11/2018 | Santana | |
| 2019/0000489 A1 | 1/2019 | Broderick et al. | |
| 2019/0038884 A1 | 2/2019 | Roux et al. | |
| 2019/0046255 A1 | 2/2019 | Davalos et al. | |
| 2019/0117964 A1 | 4/2019 | Bahrami et al. | |
| 2019/0125165 A1* | 5/2019 | Ørntoft | A61B 18/1492 |
| 2019/0175836 A1 | 6/2019 | Bernard et al. | |
| 2019/0284263 A1 | 9/2019 | Smith et al. | |
| 2019/0336757 A1 | 11/2019 | Rodriguez et al. | |
| 2020/0016400 A1 | 1/2020 | Fisher et al. | |
| 2020/0038248 A1 | 2/2020 | Timnak et al. | |
| 2020/0054874 A1 | 2/2020 | Gehl et al. | |
| 2020/0289818 A1 | 9/2020 | Neken et al. | |
| 2020/0318055 A1 | 10/2020 | Dai | |
| 2021/0187287 A1* | 6/2021 | Bezalel | A61N 1/20 |
| 2022/0151861 A1 | 5/2022 | Ignon et al. | |

FOREIGN PATENT DOCUMENTS

| | | | |
|---|---|---|---|
| EP | 1100579 A1 | 5/2001 | |
| EP | 2680881 B1 | 4/2017 | |
| EP | 2475421 B1 | 8/2017 | |
| EP | 3515549 A1 | 7/2019 | |
| EP | 3524316 A1 | 8/2019 | |
| JP | 60-037337 U | 3/1985 | |
| JP | 2005-521538 A | 7/2005 | |
| JP | 2011-509743 A | 3/2011 | |
| JP | 2018-527052 A | 9/2018 | |
| JP | 2019-520132 A | 7/2019 | |
| JP | 2020-500039 A | 1/2020 | |
| JP | 7530439 B2 | 8/2024 | |
| KR | 10-1872408 B1 | 6/2018 | |
| WO | 2014/066655 A2 | 5/2014 | |
| WO | 2017/117508 A1 | 7/2017 | |
| WO | 2018/057900 A1 | 3/2018 | |
| WO | 2019/237107 A1 | 12/2019 | |
| WO | 2020/257895 A1 | 12/2020 | |
| WO | 2021/007315 A1 | 1/2021 | |
| WO | 2021/081381 A1 | 4/2021 | |

OTHER PUBLICATIONS

Fisher et al.; "Adipose tissue: a new target for electroporation-enhanced DNA vaccines"; Gene Therapy; vol. 24; 2017; p. 757-767.
ISA/220—Notification of Transmittal or Search Report and Written Opinion of the ISA, or the Declaration Mailed on Feb. 9, 2024 for WO Application No. PCT/US23/074307, 7 page(s).
Lallow et al.; "Novel suction-based in vivo cutaneous DNA transfection platform"; Science Advances; vol. 7 No. 45; Nov. 2021; 9 pages.
Schultheis et al.; "Characterization of guinea pig T cell responses elicited after EP-assisted delivery of DNA vaccines to the skin"; Vaccine; vol. 35; 2017; p. 61-70.
Schultheis et al.; "Optimized Interferon-gamma ELISpot Assay to Measure T Cell Responses in the Guinea Pig Model after Vaccination"; Journal of Visualized Experiments; vol. 143; e58595; Jan. 2019; 7 pages.
Supplementary European search report Mailed on Apr. 19, 2024 for EP Application Number 21770546, 10 page(s).
Extended European Search Report Mailed on Sep. 17, 2024 for EP Application No. 21770546, 11 page(s).

* cited by examiner

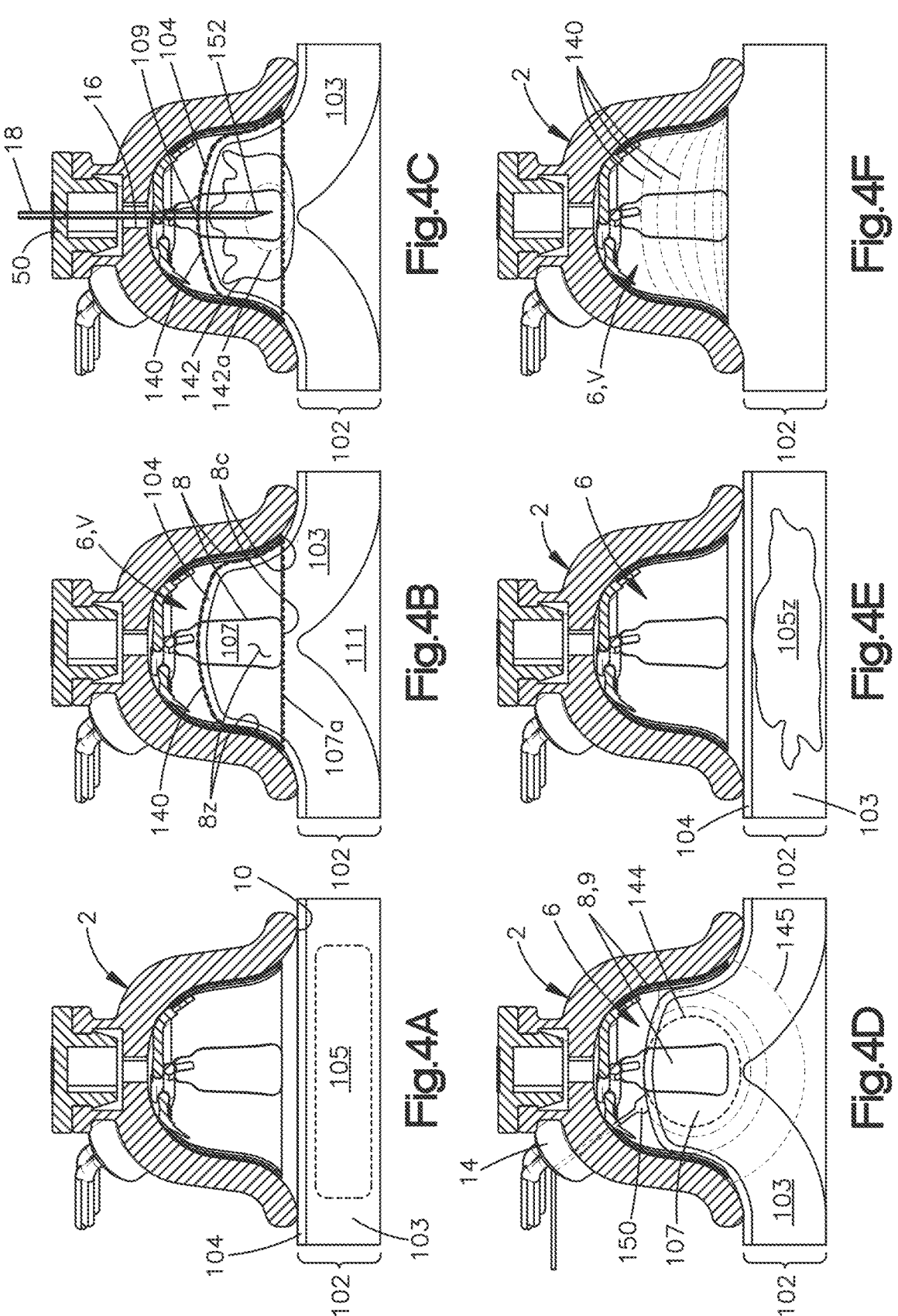

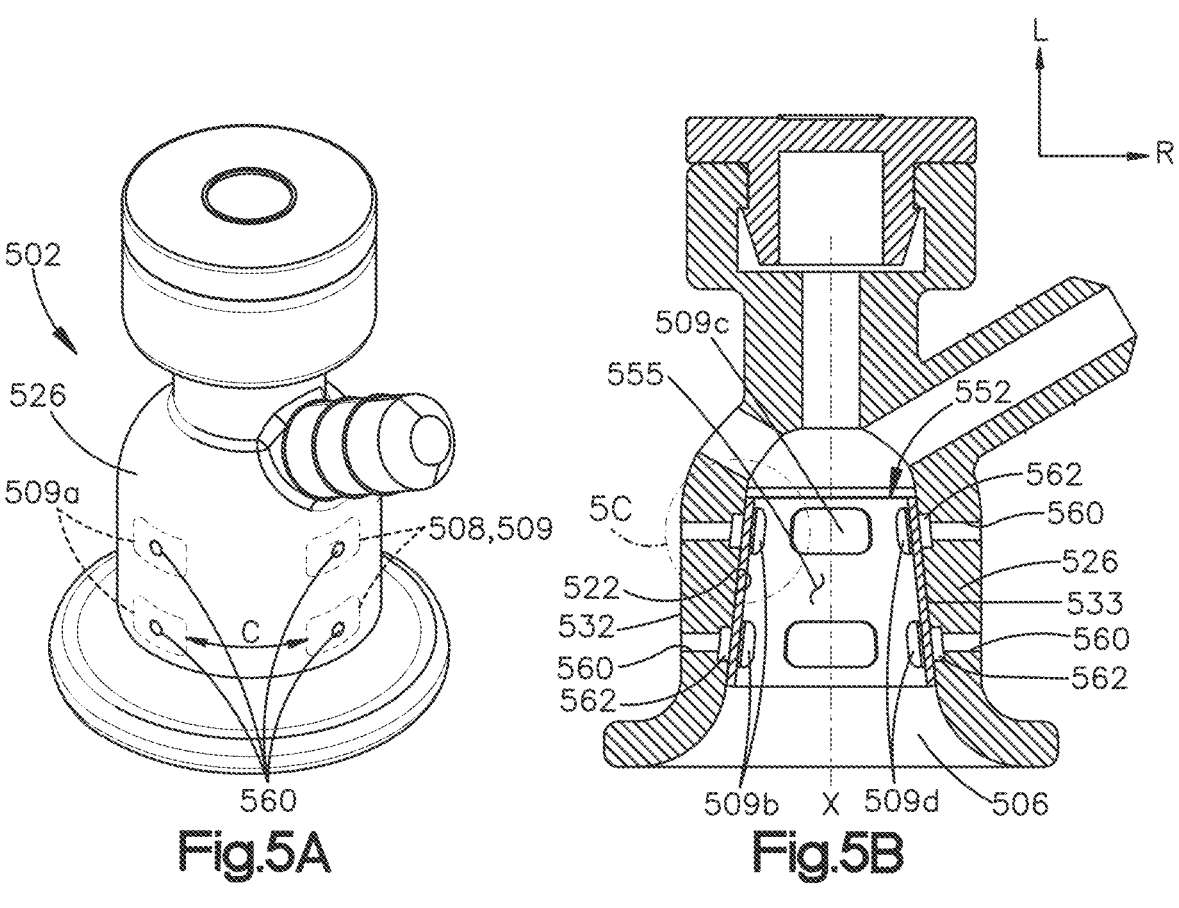
Fig.5A
Fig.5B
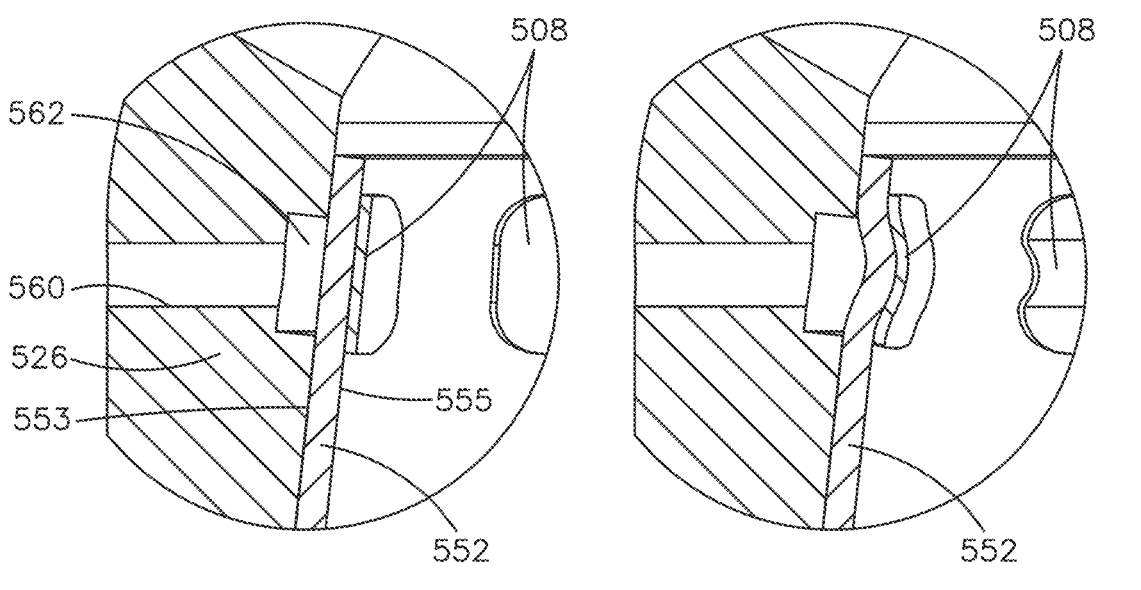
Fig.5C
Fig.5D

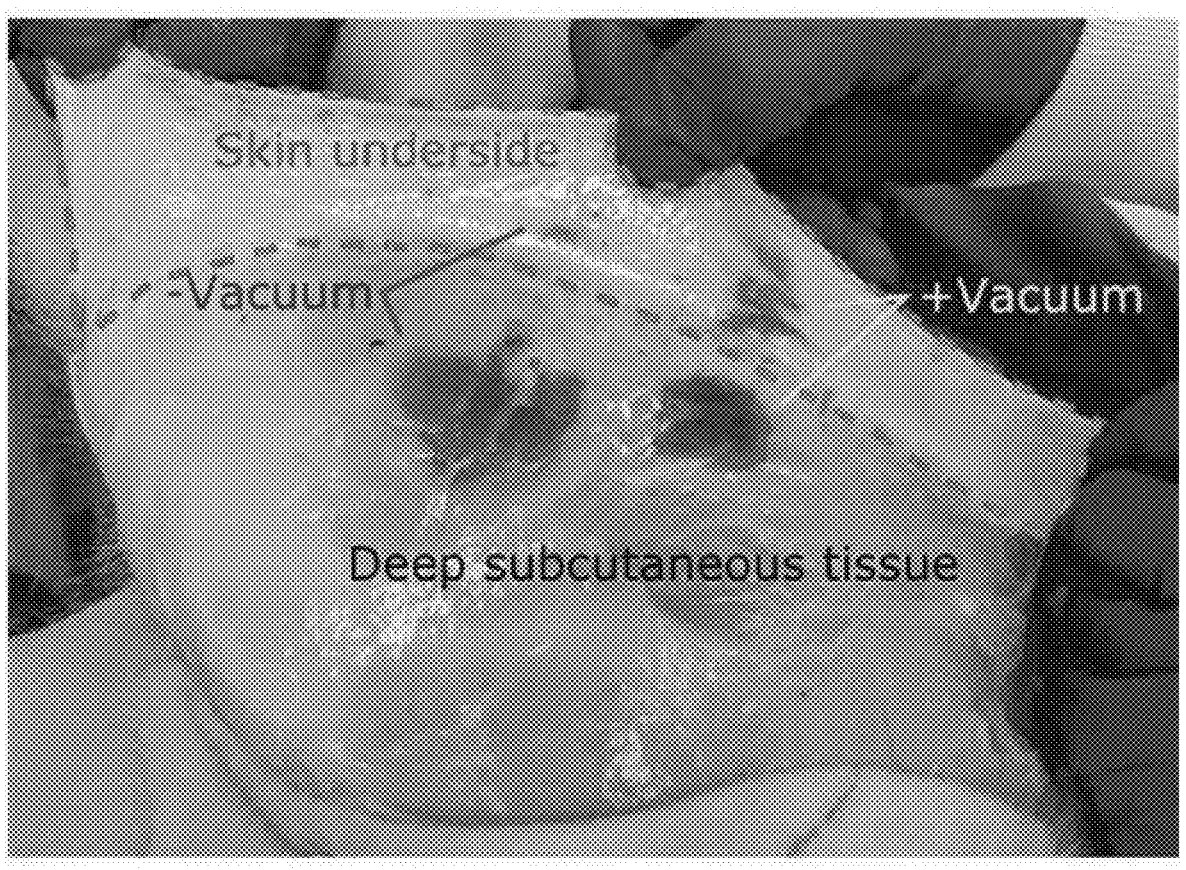
Fig.11A
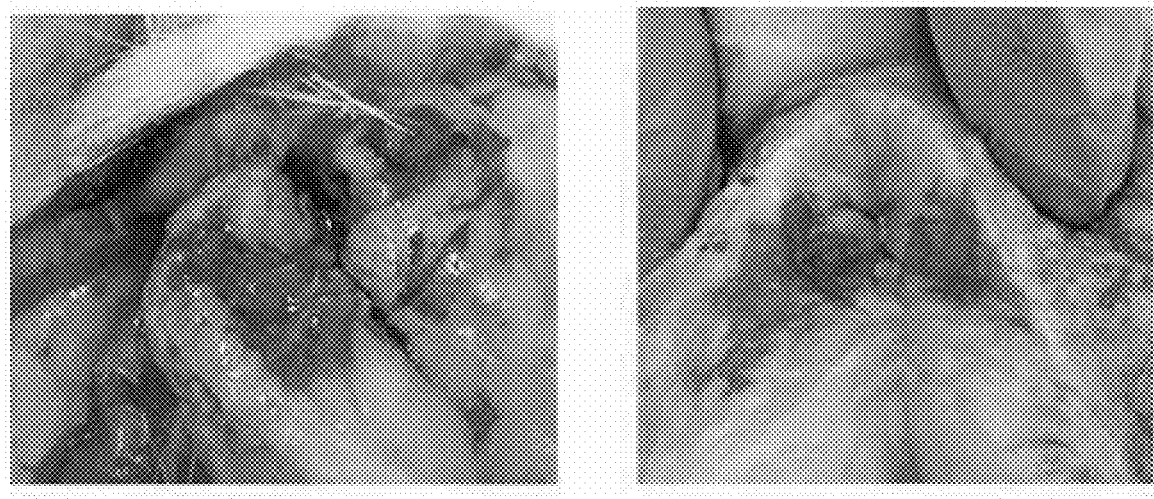
Fig.11B                              Fig.11C

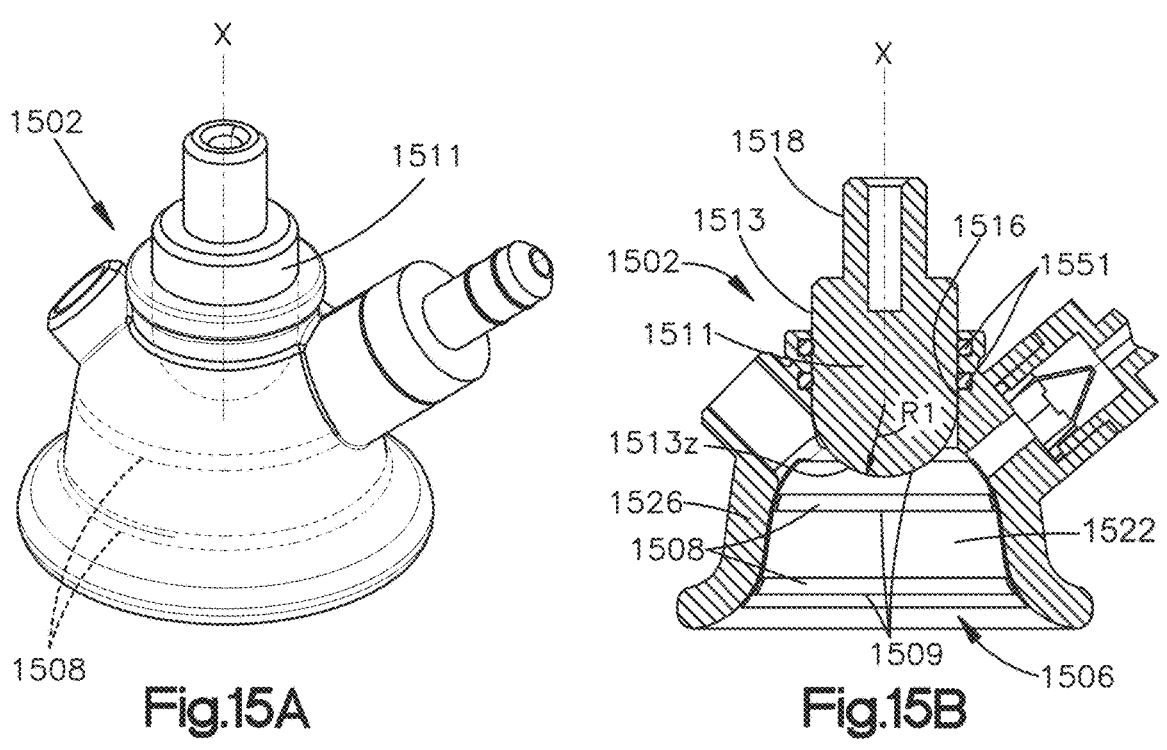
Fig.15A
Fig.15B
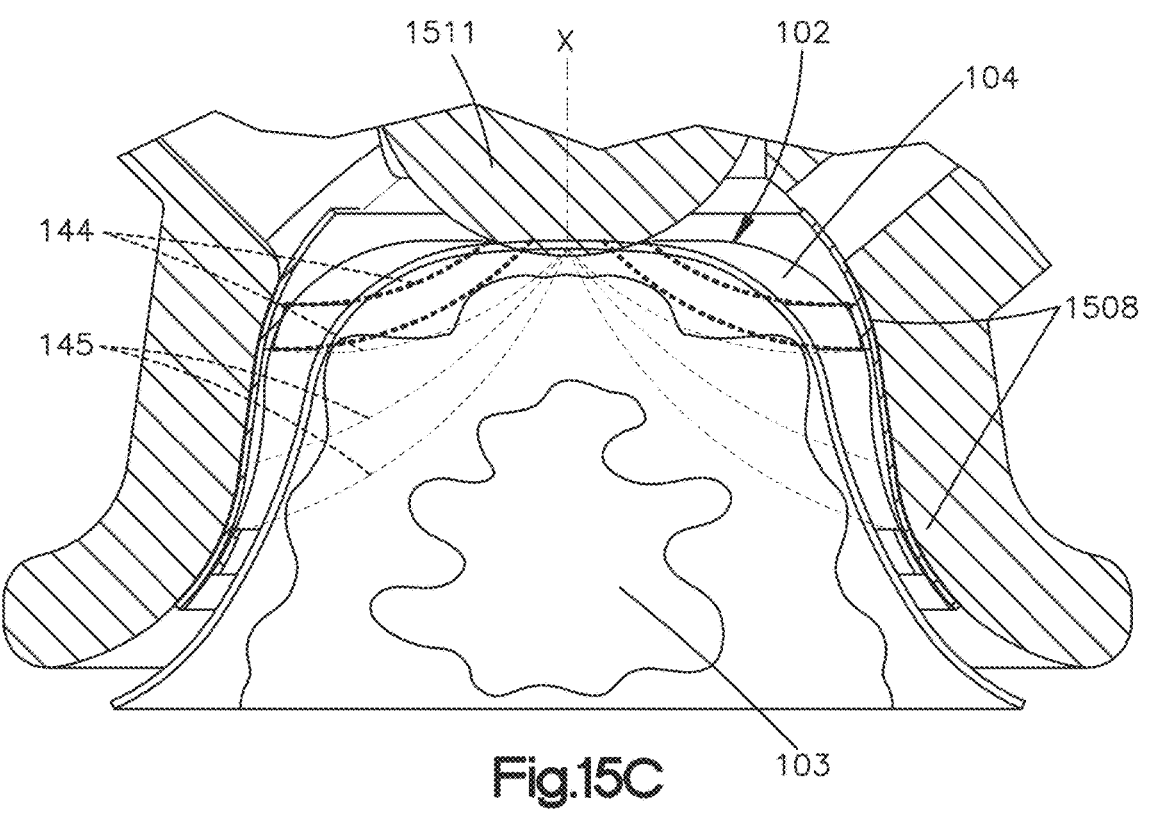
Fig.15C

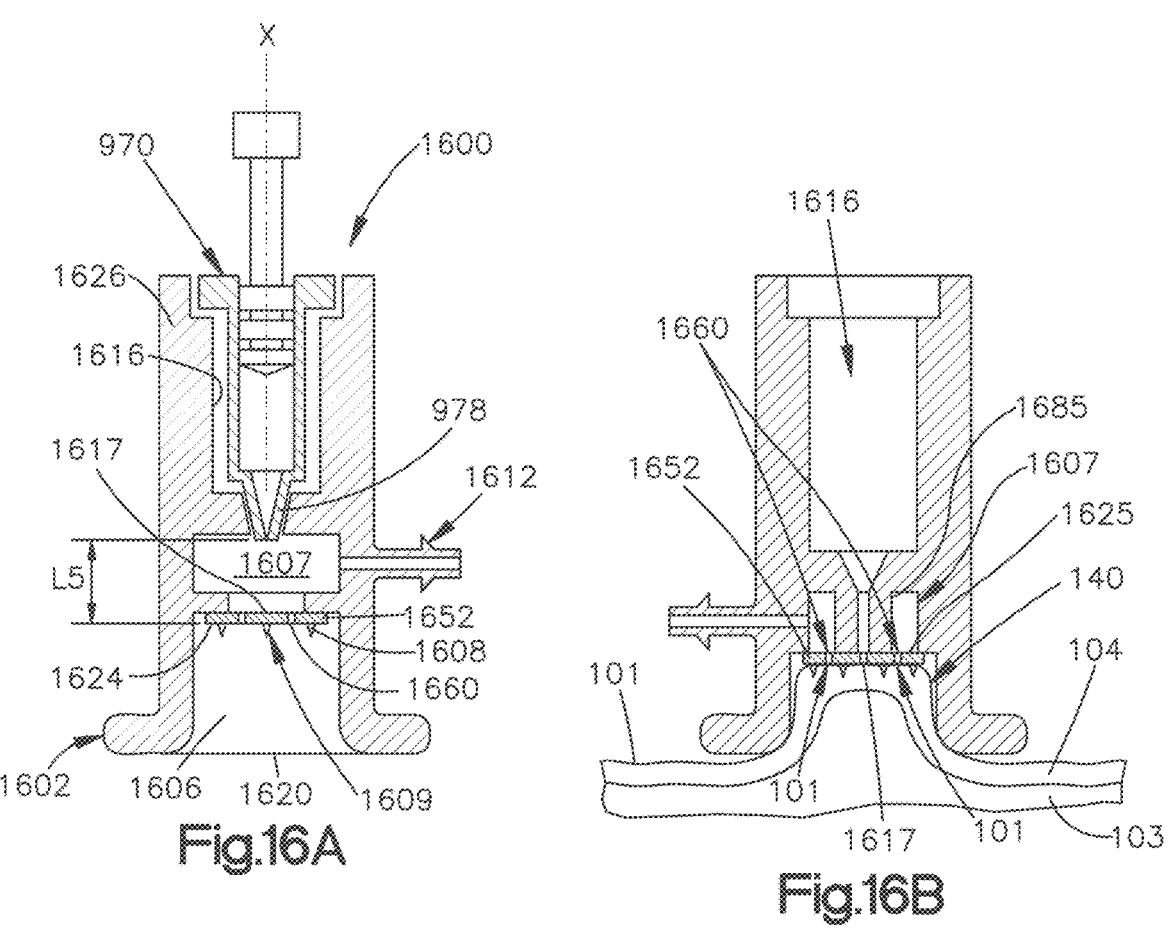
Fig.16A
Fig.16B
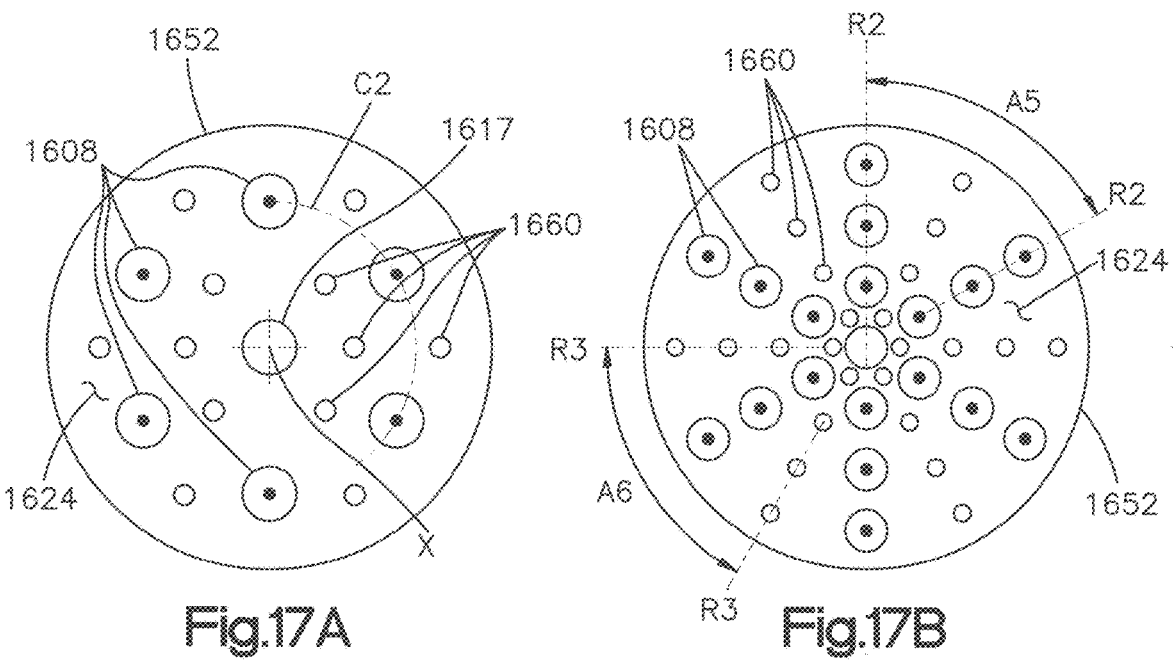
Fig.17A
Fig.17B

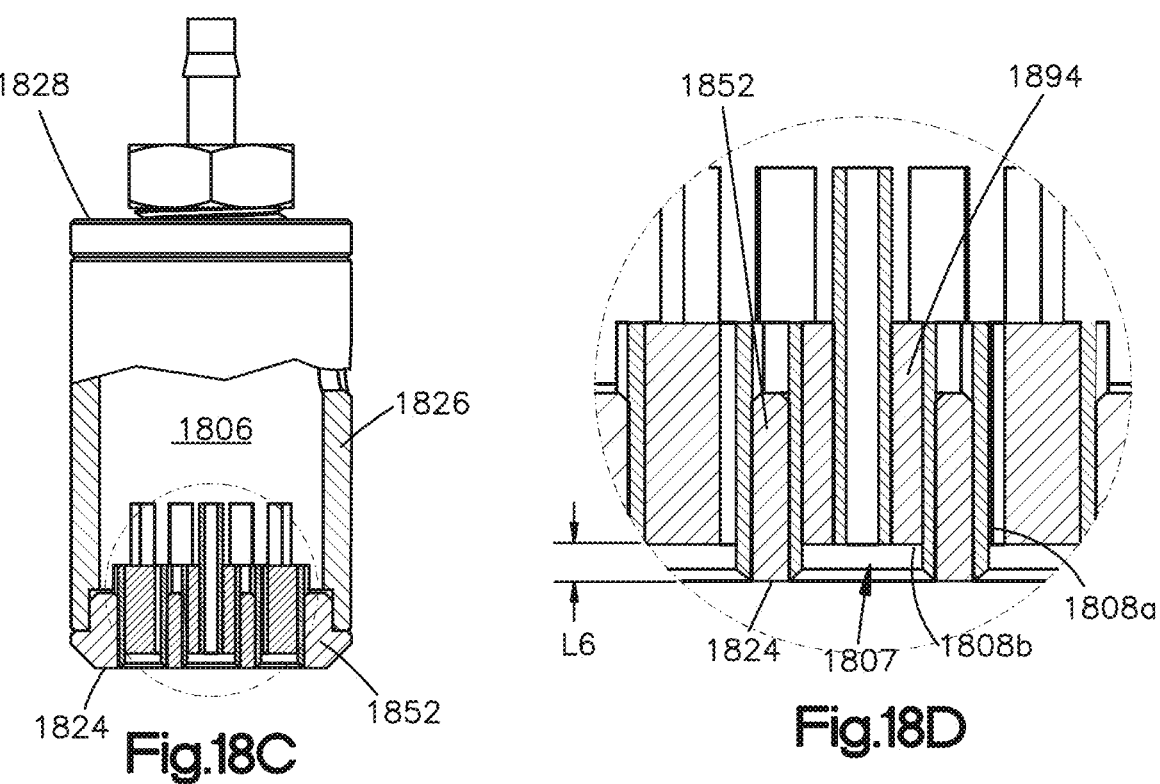
1828
1806
1826
1824          Fig.18C          1852
1852          1894
L6          1824          1807          1808b          1808a          Fig.18D
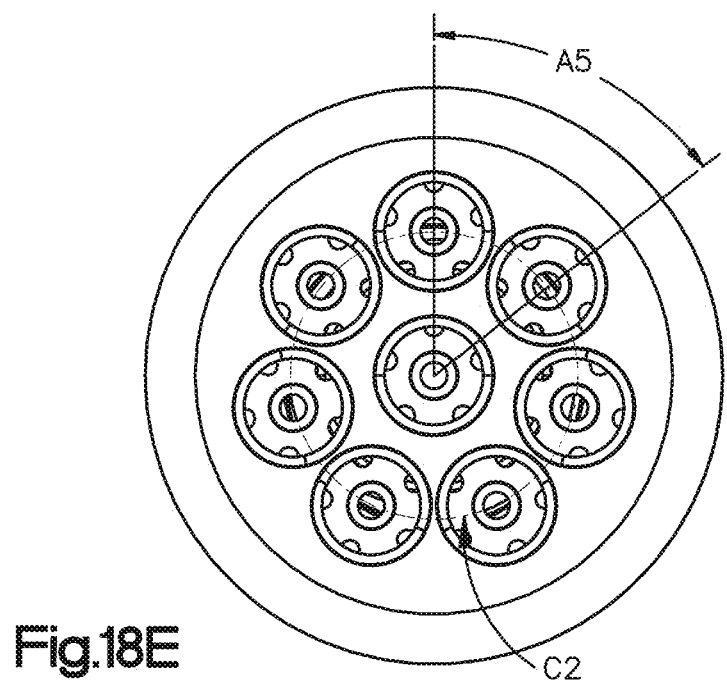
A5
Fig.18E          C2

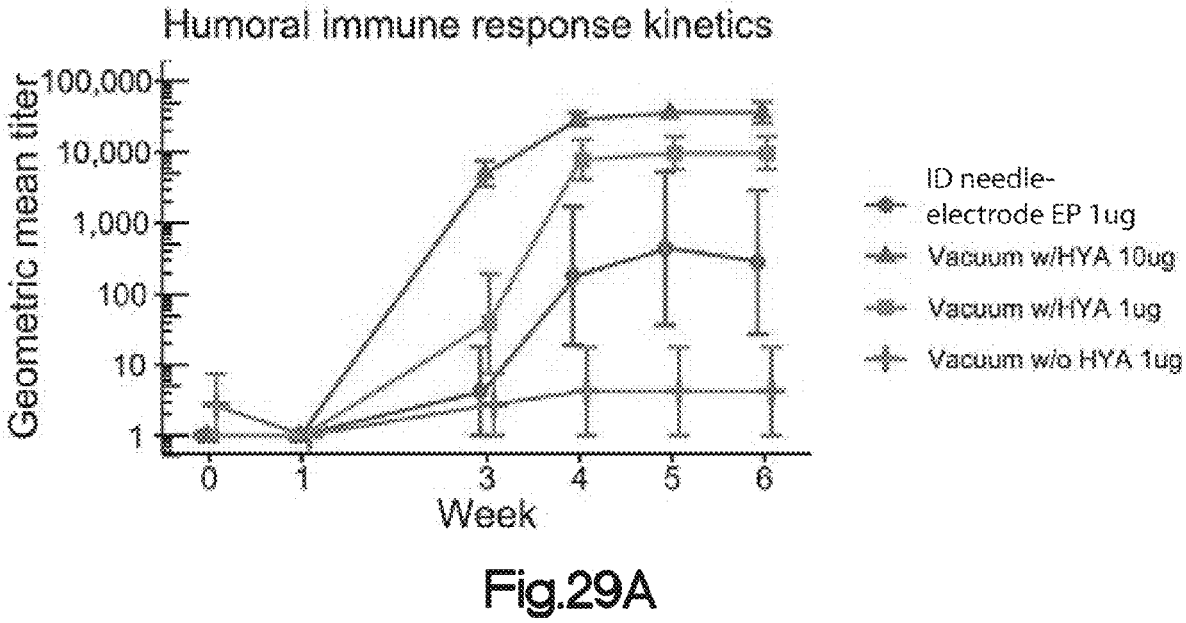
Fig.29A
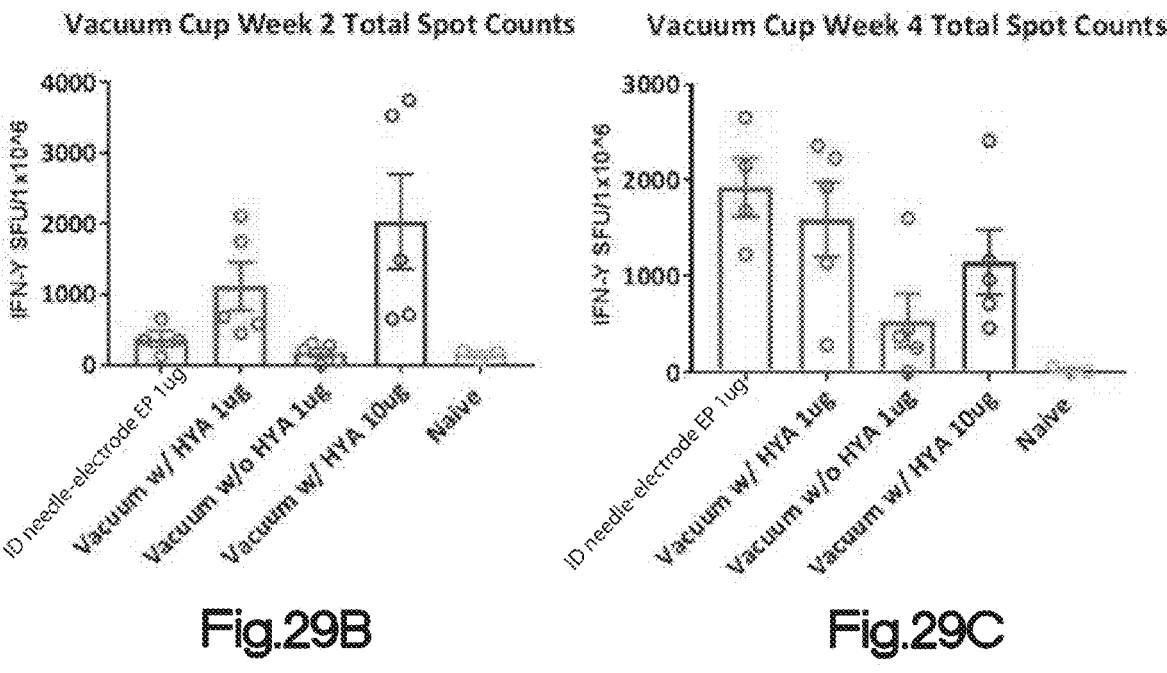
Fig.29B                    Fig.29C

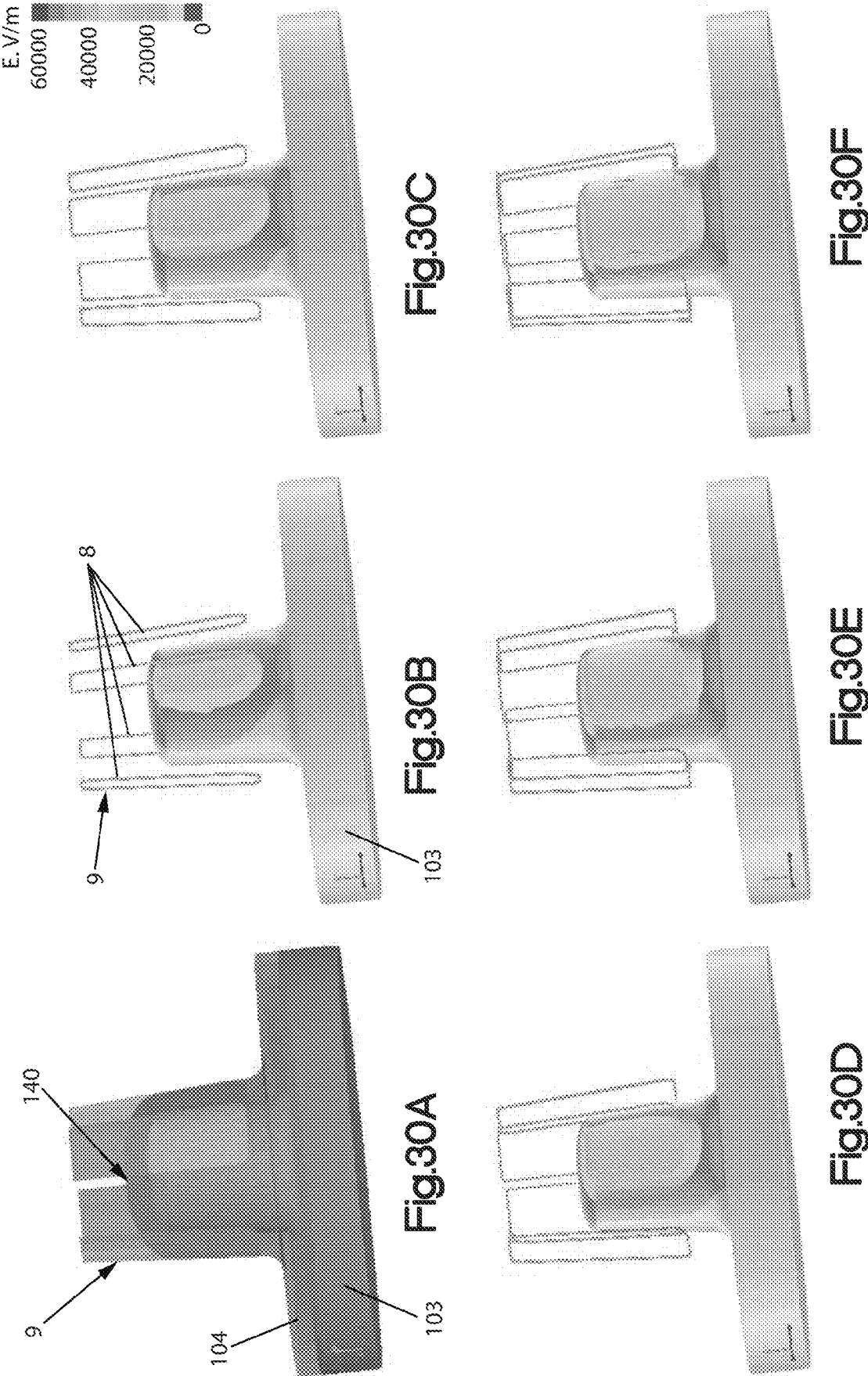

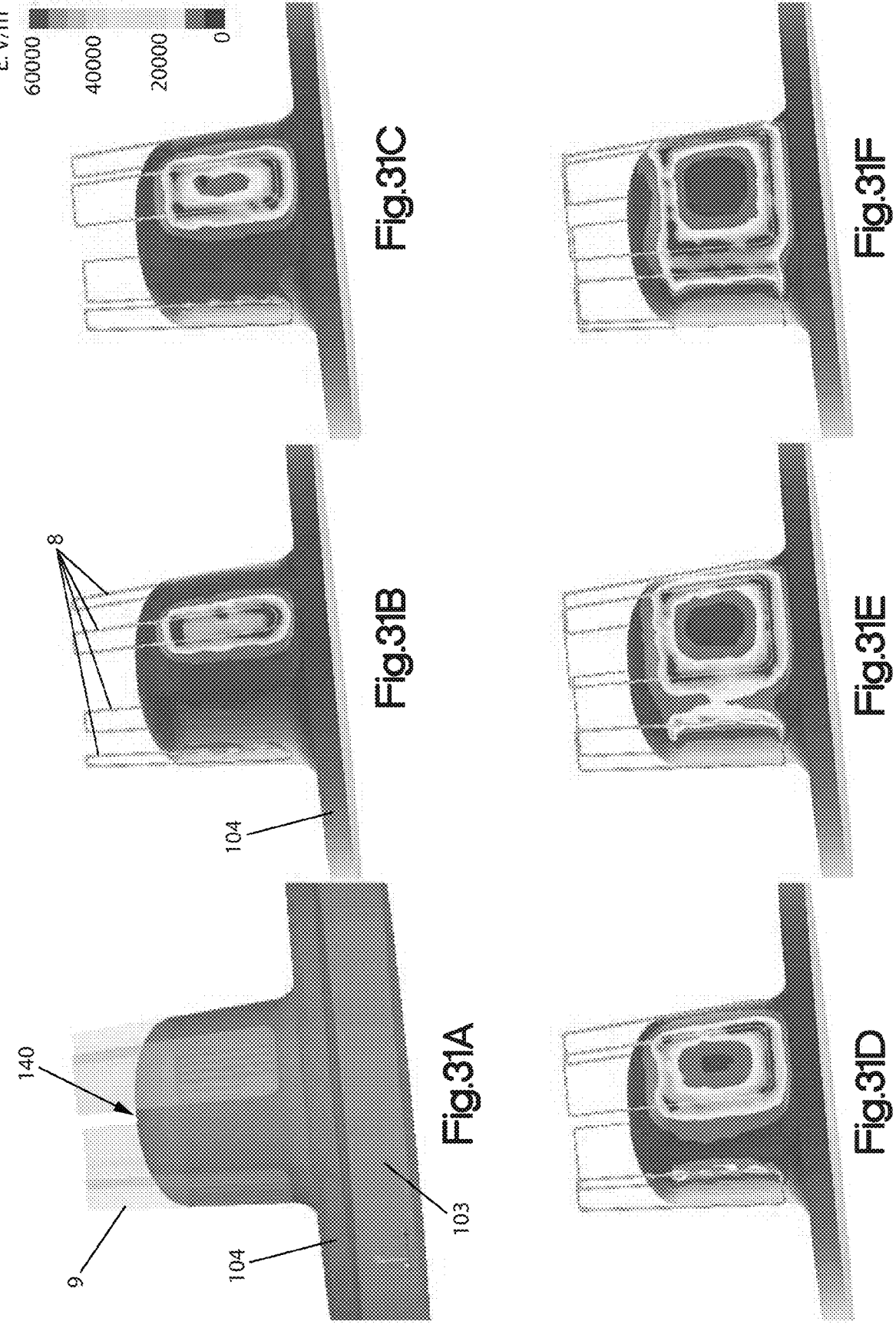

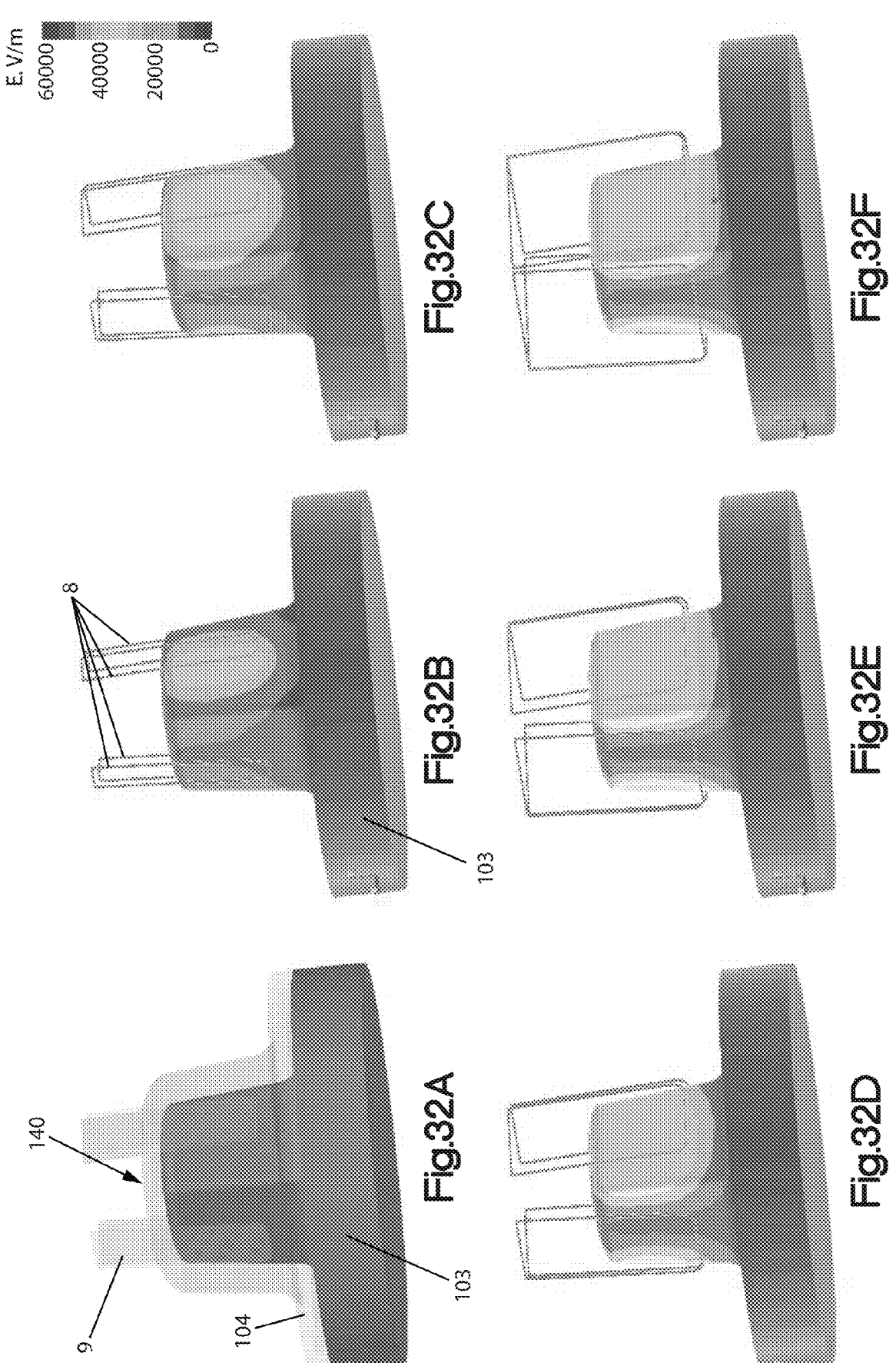

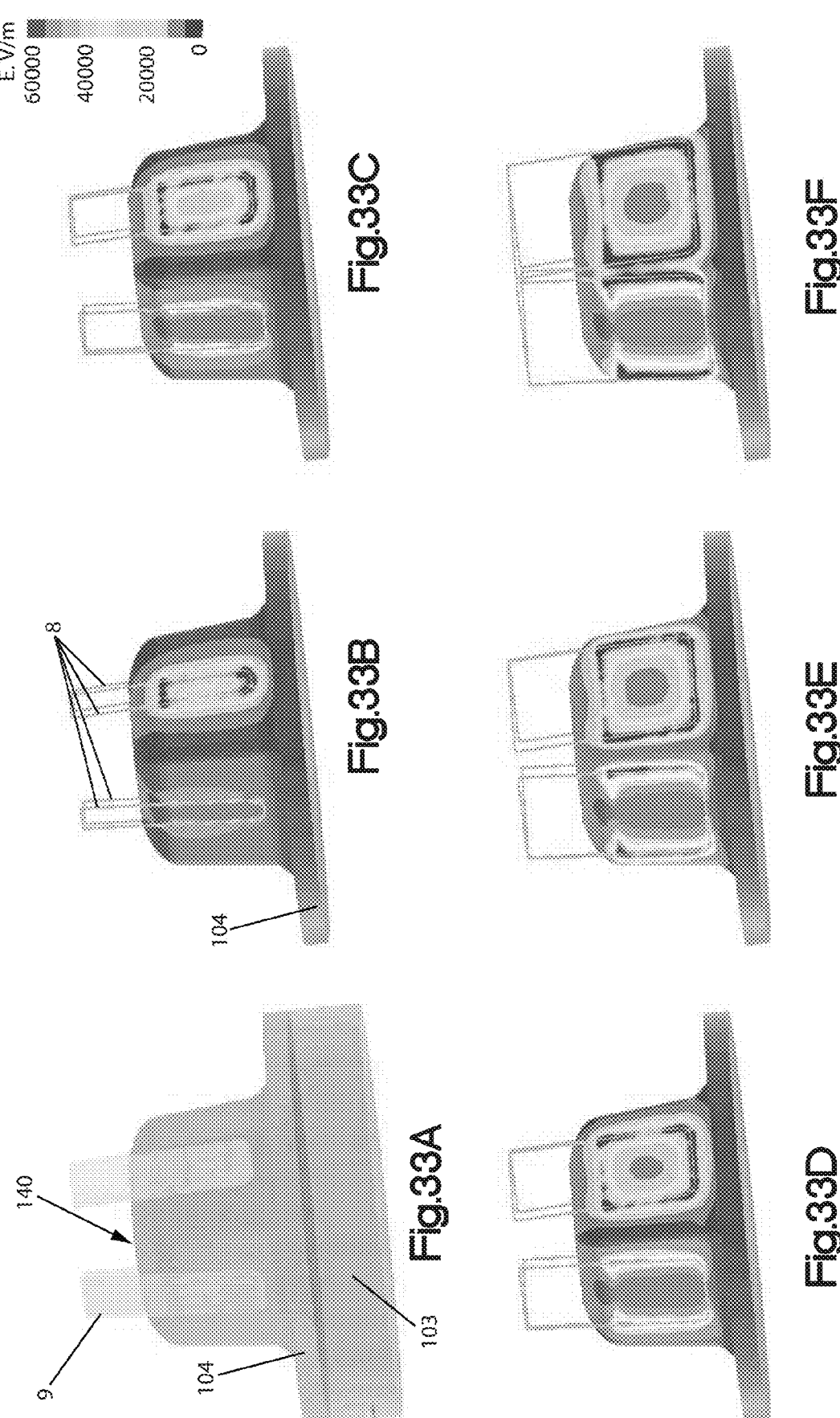

Vacuum Only

Vacuum + EP

A

B

MERS, 50ug

PRE

DURING

POST

VACUUM-ASSISTED ELECTROPORATION DEVICES, AND RELATED SYSTEMS AND METHODS

CROSS-REFERENCE TO RELATED APPLICATIONS

The present application claims the benefit of U.S. Provisional Application No. 62/992,513, filed Mar. 20, 2020, the entire contents of which are incorporated herein by this reference.

TECHNICAL FIELD

The present invention relates to devices for gripping and deforming tissue with vacuum pressure, injecting fluid into the tissue, and electroporating the tissue with electrodes, as well as to systems and methods related to injecting or otherwise delivering fluid into the tissue and electroporating tissue.

BACKGROUND

In the 1970s, it was discovered that electrical fields could be used to create pores in cells without causing permanent damage to the cell. This discovery, termed electroporation (EP) made it possible for large molecules, small molecules, ions, and water to be introduced into a cell's cytoplasm through the cell wall. In some instances, electroporation can be used in topical treatments, such as head and neck cancer, to introduce chemicals and other compounds into the tumor. During these procedures, the patient may or may not be under general anesthesia so pain and involuntary muscle movement must be minimized.

Skin is a popular target for EP because it is easily accessed and contains a rich variety of immune cells suitable for delivery of a DNA vaccine. The natural immune function of skin and its high rate of cellular turnover typically leads to rapid, strong humoral responses to EP-enhanced DNA vaccine delivery. Skin is also capable of generating cellular immune responses following EP-enhanced DNA vaccine delivery. Due to its superficial nature, skin is suitable for minimally invasive or noninvasive EP.

Skeletal muscle is also a well-characterized target for electroporation-mediated (EP) delivery of DNA in vivo. Myocytes are capable of producing and secreting proteins for long periods of time, and it has been repeatedly demonstrated that EP enhanced DNA vaccinations into muscle are able to generate an immune response. However, applications of muscle EP DNA delivery are complicated by the variable thickness of subcutaneous fat, preventing a "one size fits all" approach since different fat thicknesses result in different needle penetration depths into the muscle tissue. Skeletal muscle, particularly in larger animals and humans, is typically unsuitable for minimally invasive or noninvasive EP techniques because of the insulating subcutaneous fat layer and the depth required to generate electric fields. Therefore, penetrating needle electrodes are most commonly used to perform EP in muscle.

Historically, adipose tissue (fat) has been viewed as an inert tissue primarily used to store energy in the form of lipid droplets. As such, only recently have EP-enhanced DNA procedures been directed to the adipose layer of tissue. However, recent studies have shown that subcutaneous fat actually serves many dynamic roles. Adipose tissue contains many stem cells and immune cells, and acts as an endocrine organ by secreting numerous hormones, secretes many local signals, and contains an elaborate network of capillaries. Attempts to achieve in vivo transfection of adipose tissue have mainly been limited to surgical techniques that require the administrator to cut away and physically remove samples of the patient's skin to allow contact with the adipose tissue directly. These treatments are extremely invasive and are not suitable for clinical devices.

SUMMARY

According to an embodiment of the present disclosure, a device for vacuum-assisted in vivo electroporation of tissue includes a housing that defines a chamber and at least one opening into the chamber. A port extends through the housing and is remote from the at least one opening and is connectable to a vacuum source. The port is configured to communicate vacuum pressure from the vacuum source to the chamber. A plurality of electrodes are positioned within the chamber and are configured to delivery one or more electroporation pulses to a targeted portion of tissue extending through the opening and at least momentarily held in the chamber responsive to the vacuum pressure.

According to another embodiment of the present disclosure, a method of electroporating the tissue of a subject includes placing a chamber adjacent the tissue, applying vacuum pressure to the chamber, thereby drawing the tissue through an opening of the chamber and into contact with a plurality of electrodes extending along an interior surface of the chamber, and delivering one or more electroporating pulses through the plurality of electrodes to the tissue, thereby creating an electroporation field within the tissue.

According to a further embodiment of the present disclosure, a device for vacuum-assisted treatment of tissue includes a housing defining a chamber and at least one opening into the chamber. A first port extends through the housing and is remote from the at least one opening. The first port is connectable to a vacuum source, such that the first port is configured to communicate vacuum pressure from the vacuum source to the chamber. The device includes a jet-injection device that extends through a second port into the chamber. The second port is opposite the at least one opening. The jet-injection device is configured to deliver a jet injection of fluid to a targeted portion of tissue extending through the at least one opening and at least momentarily held in the chamber responsive to the vacuum pressure.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing summary, as well as the following detailed description of illustrative embodiments of the present application, will be better understood when read in conjunction with the appended drawings. For the purposes of illustrating the structures of the present application, there is shown in the drawings illustrative embodiments. It should be understood, however, that the application is not limited to the precise arrangements and instrumentalities shown. In the drawings;

FIGS. 4A-4E are sectional side views of the vacuum cup illustrated in FIG. 2A adjacent tissue, showing representative stages of employing the vacuum cup in a vacuum-assisted electroporation treatment;

FIG. 4F is a sectional side view of the vacuum cup illustrated in FIG. 2A, showing various extents to which the vacuum cup can draw tissue into the vacuum chamber;

FIG. 5A is a perspective view of a vacuum cup having flexible electrodes, according to an embodiment of the present disclosure;

FIG. 5B is a sectional side view of the vacuum cup illustrated in FIG. 5A, taken along a central axis of the cup;

FIG. 5C is an enlarged sectional view of region 5C-5C illustrated in FIG. 5B, showing the electrodes in a neutral state;

FIG. 5D is an enlarged sectional view of region 5D-5D illustrated in FIG. 5B, showing the electrodes in a flexed state;

FIG. 11A is a visual representation of methylene blue distribution in subcutaneous pig tissue without application of vacuum pressure (left) and with application of vacuum pressure (right) via a vacuum cup configured similarly to the cup illustrated in FIG. 2A;

FIGS. 11B and 11C show a side-by-side comparison of fluid distribution in guinea pig adipose tissue after injection of methylene blue; the injection in FIG. 11B was performed with a needle-free vacuum cup similar to that shown in FIG. 9A; the injection in FIG. 11C was performed with a subcutaneous needle technique;

FIG. 15A is a perspective view of a vacuum cup configured for vacuum-assisted electroporation of intradermal tissue, according to an embodiment of the present disclosure;

FIG. 15B is a sectional side view of the vacuum cup illustrated in FIG. 15A;

FIG. 15C is an enlarged sectional view of the vacuum chamber of the cup illustrated in FIG. 15A during use;

FIGS. 16A-16B are sectional side views of vacuum-electroporation assemblies, in which electrodes are disposed on an end surface within the respective vacuum chambers that are opposite respective distal openings of the vacuum chamber, according to embodiments of the present disclosure;

FIGS. 17A-17B are bottom plan views of electrode array patterns and vacuum port patterns defined on respective electrode support members for use with the assemblies illustrated in FIGS. 16A-16B, according to embodiments of the present disclosure;

FIG. 18C is a side sectional view of the vacuum-electroporation device illustrated in FIG. 18A;

FIG. 18D is an enlarged sectional view of region 18D-18D illustrated in FIG. 18C;

FIG. 18E is a bottom plan view of the vacuum-electroporation device illustrated in FIG. 18A;

FIG. 29A is a graph showing 6-week humoral immunogenicity data in terms of mean endpoint titers in guinea pigs after intradermal injections of a DNA vaccine against Influenza nucleoprotein (pGX 2013), particularly showing comparative humoral immune responses following respective electroporation treatments in skin using: a prior art needle-array electroporation device; and a version of the vacuum cup illustrated in FIG. 2A having a 15 mm chamber diameter;

FIGS. 29B and 29C are charts showing cellular immune responses in terms of spot forming units at Week 2 (FIG. 29B) and Week 4 (FIG. 29C) from the same study illustrated in FIG. 29A;

FIG. 30A illustrates a perspective view of a circular electrode array having four (4) electrodes spaced at 90-degree intervals about a central axis for use with a circular-opening vacuum cup of the present disclosure to electroporate adipose tissue: FIGS. 30B-30F illustrate various simulated electrical field strengths created in adipose tissue according to various electrode sizes:

FIG. 31A illustrates a perspective view of the circular electrode array shown in FIG. 30A for use electroporating skin tissue: FIGS. 31B-31F illustrate various simulated electrical field strengths created in skin tissue according to various electrode sizes;

FIG. 32A illustrates a perspective view of a rectangular electrode array having four (4) planar electrodes spaced at 90-degree intervals about a central axis for use with a rectangular-opening vacuum cup of the present disclosure to electroporate adipose tissue: FIGS. 32B-32F illustrate various simulated electrical field strengths created in adipose tissue according to various electrode sizes;

FIG. 33A illustrates a perspective view of the rectangular electrode array shown in FIG. 32A for use electroporating skin tissue: FIGS. 33B-33F illustrate various simulated electrical field strengths created in skin tissue according to various electrode sizes;

FIGS. 43A and 4B are fluoroscopic images showing an injectate disposed in guinea pig skin that is positioned beneath a vacuum cup having the electrode array shown in FIG. 40B; FIG. 43A shows the injectate before application of vacuum pressure in the chamber.

FIGS. 45A-47C are fluoroscopic images showing tissue deflection in guinea pigs during and after jet-injections performed with a jet-injection vacuum cup similar to that illustrated in FIG. 9A at various vacuum pressure settings and nozzle-to-skin offset distance settings.

DETAILED DESCRIPTION OF ILLUSTRATIVE EMBODIMENTS

Figure 1:
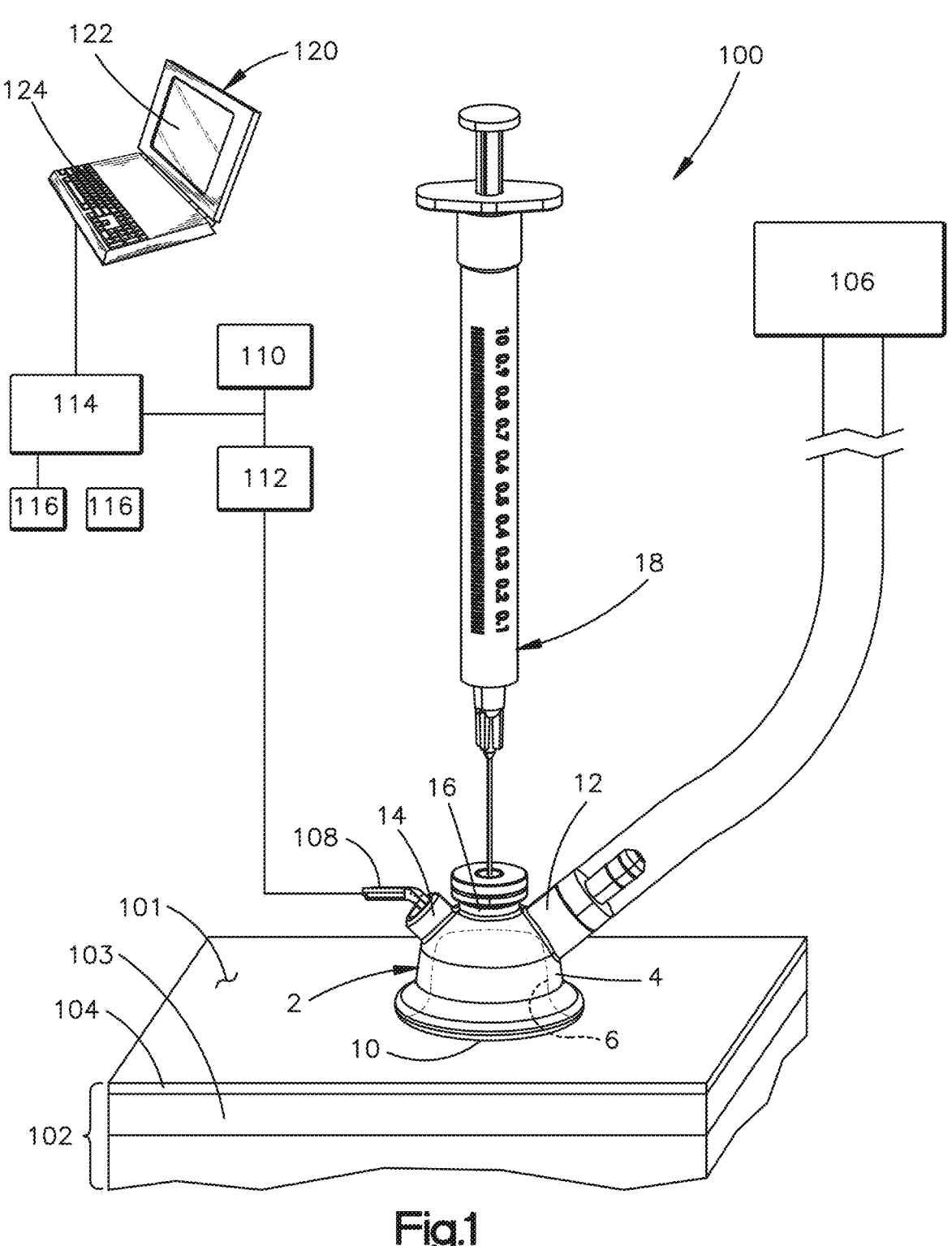
FIG. 1 is a diagrammatical view of an electroporation system that employs a vacuum-assisted electroporation cup (or "vacuum cup") in combination with a needle injection device, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a." "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

The term "agent", as used herein, means a polypeptide, a polynucleotide, a small molecule, or any combination thereof. The agent may be a recombinant nucleic acid sequence encoding an antibody, a fragment thereof, a variant thereof, or a combination thereof. The agent may be formulated in water or a buffer, such as saline-sodium citrate (SSC) or phosphate-buffered saline (PBS), by way of non-limiting examples.

The term "intradermal" as used herein, means within the layer of skin that includes the epidermis (i.e., the epidermal layer, from the stratum corneum to the stratum basale) and the dermis (i.e., the dermal layer).

The term "adipose", as used herein, means the layer containing adipocytes (i.e., fat cells) that reside in the subcutaneous layer.

The term "electroporation", as used herein, means employing an electrical field within tissue that temporarily and reversibly increases the permeability and/or porosity of the cell membranes of cells in the tissue, thereby allowing an agent, for example, to be introduced into the cells.

The term "electroporation field", as used herein, means an electric field capable of electroporating cells. In instances where an electric field includes a portion that is capable of electroporating cells and another portion that is incapable of electroporating cells, the "electroporation field" refers specifically to that portion of the electric field that is capable of electroporating cells. Thus, an electroporation field can be a subset of an electric field.

The term "zone", as used herein, means a volume of space, such as a volume of space within tissue.

The term "transfection zone", as used herein, means a volume of tissue in which transfection occurs, and can be used synonymously with the term "transfection volume."

The term "cellular infiltration", as used herein, means migration of cells into a volume of tissue.

The terms "intradermal needle-electrode electroporation device" and "ID needle-electrode EP", as used herein, each refer to a prior art electroporation device that employs an electrode array of three (3) needle electrodes arranged in a triangular pattern to electroporate intradermal tissue.

The embodiments described below pertain to systems and devices that perform vacuum-assisted electroporation of tissue, particularly a targeted layer of tissue, such as intradermal tissue or adipose tissue. These embodiments subject a targeted volume of the tissue (or "tissue volume") to vacuum pressure (i.e., negative pressure) to deform the tissue in a manner favorable for electroporating cells within a target zone in the tissue layer. In particular, an open end of a vacuum device, such as a vacuum cup, is placed in contact with an outer surface of the tissue (e.g., the "skin") overlying the tissue volume, and vacuum pressure is applied to an interior of the cup, thereby drawing the tissue volume into the vacuum cup, which positionally secures the tissue volume to the cup, allowing electrodes positioned within the vacuum cup to generate a predictable, substantially uniform electroporation field within the tissue volume, thereby resulting in a predictable, substantially uniform transfection zone within the tissue volume. The vacuum pressure provided by the embodiments described below has also been observed to provide favorable redistribution of fluid within the tissue volume, including favorable in vivo dispersion of an injectate within the tissue volume, and also favorable in vivo ingress and egress of fluid into and out of the target zone. Stated differently, the vacuum pressure enhances the dispersion of the injectate throughout the tissue to enlarge the transfection zone and also draws more in vivo fluids into the target zone, increasing the amount of cells that are exposed to transfected cells. The inventors have observed that the vacuum-assisted electroporation treatments described throughout this disclosure have resulted in subjects' increased responses to injectates.

The inventors have also observed, surprisingly and unexpectedly, that application of vacuum pressure can cause transfection within the tissue volume even without electroporation. While wishing not to be bound by any particular theory, the inventors believe that the vacuum pressure imparted by the vacuum cup imparts mechanical stresses on the cell membranes within the tissue volume that increases cell membrane permeability and thus the observed transfection within the tissue volume. The inventors also believe that the aforementioned fluid redistribution might also be at least partially responsible for the observed transfection without electroporation. The inventors further believe that the aforementioned fluid redistribution and mechanical stresses likely interact with one another to create a favorable environment within the tissue volume for transfection of external agents into the cells.

Furthermore, the embodiments described below can also be adaptable between uses and/or during use without mechanical reconfiguration. For example, during and/or between uses, electrical parameters of the electrodes can be adjusted as needed to manipulate the electroporation field in the tissue volume to achieve favorable treatment results. Additionally or alternatively, the vacuum pressure can be adjusted as needed during and/or between uses to physically manipulate the tissue volume to achieve favorable treatment results. For example, a higher vacuum pressure can be applied to draw a larger tissue volume into vacuum cup and a lower vacuum pressure can be applied to draw a lesser tissue volume into the vacuum cup. In this manner, the same vacuum cup can be employed to target different tissue layers for electroporative treatment by selectively exposing different tissue layers to the electroporation field. Additionally, the vacuum pressure can be pulsed during use to manipulate the mechanical behavior of the targeted tissue, such as to enhance fluid redistribution within the tissue.

Referring now to FIG. 1, an electroporation system 100 for treating a patient according to the present disclosure includes a vacuum-assisted electroporation device 2, which includes a housing 4 that defines an internal vacuum chamber 6 and a plurality of electrodes 8 (see, e.g., FIGS. 2A-2C) positioned within the chamber 6. The plurality of electrodes 8 are arranged into an array 9 of electrodes 8, which can also be referred to as an electrode array 9. The device 2 can also be referred to as a "vacuum cup" or simply a "cup." The housing 4 can be referred to as a "cup housing". The vacuum cup 2 is configured so that a physician can place a distal end 10 of the vacuum cup 2 onto an outer surface 101 of tissue 102 targeted for electroporation treatment and can apply vacuum pressure to the vacuum chamber 6 to draw; pull, or otherwise induct the tissue 102 into the vacuum chamber 6 and into contact with the electrodes 8 therein. The electrodes 8 are configured to deliver one or more electroporation pulses to the tissue 102 drawn into the chamber 6 and held therein by the vacuum pressure. The tissue 102 includes the layer targeted for treatment, such as adipose tissue 103 (also referred to herein as the "adipose layer" 103) or intradermal tissue 104 (also referred to herein as the "skin layer" 104).

The vacuum cup 2 includes one or more couplings, such as ports, for connection to one or more external components. For example, the vacuum cup 2 has a first port 12 for providing fluid communication between the vacuum chamber 6 and a vacuum source 106, such as a vacuum pump. The vacuum cup 2 can also have a second port 14 for providing access to circuitry 108 providing electrical communication between the electrodes 8 and an energy source 110, such as a power generator. The vacuum cup 2 can further include a third port 16 for providing an external tool, such as an injection device 18 carrying an injectate, particularly an injectate comprising an agent, with access to the vacuum chamber 6. As shown, the injection device 18 can be a hypodermic needle, although the vacuum cup 2 can be adapted for use with other types of injection devices 18, including jet injection devices, as described in more detail below: It should also be appreciated that the vacuum cup 2 can optionally be employed after the agent is injected into the tissue 102.

The energy source 110 can be in electrical communication with a signal generator 112, such as a waveform generator, for generating and transmitting an electric signal in the form of one or more electrical pulses having particular electrical parameters to the electrodes 8 for electroporating cells within the tissue 102 in the vacuum chamber 6. Such electrical parameters include electrical potential (voltage), electric current type (alternating current (AC) or direct current (DC)), electric current magnitude (amperage), pulse duration, pulse quantity (i.e., the number of pulses delivered), and time interval or "delay" between pulses (in multi-pulse deliveries). The signal generator 112 can include a waveform logger for recording the electrical parameters of the pulse(s) delivered. The signal generator 112 can be in electrical communication with a control unit 114 (also referred to herein as a "controller"), which can include a processor 116 configured to control operation of the electroporation system 100, including operation of the signal generator 112. The processor 116 can be in electronic communication with computer memory 118, and can be configured to execute software and/or firmware including one or more algorithms for controlling operation of the system 100. The processor 116 can be in electrical communication with a user interface 120, which can include a display 122 for presenting information relating to operation of the system 100 and a keypad 124 allowing an operator, such as physician, to input information, such as commands, relating to operation of the system 100. It should be appreciated that the display 122 can be a touchscreen display allowing the operator to input information directly at the display 122. It should also be appreciated that the interface 120 can be computer interface, such as a table-top computer or laptop computer, or a hand-held electronic device, such as a smart-phone or the like.

Figures 2A, 2B, 2C:
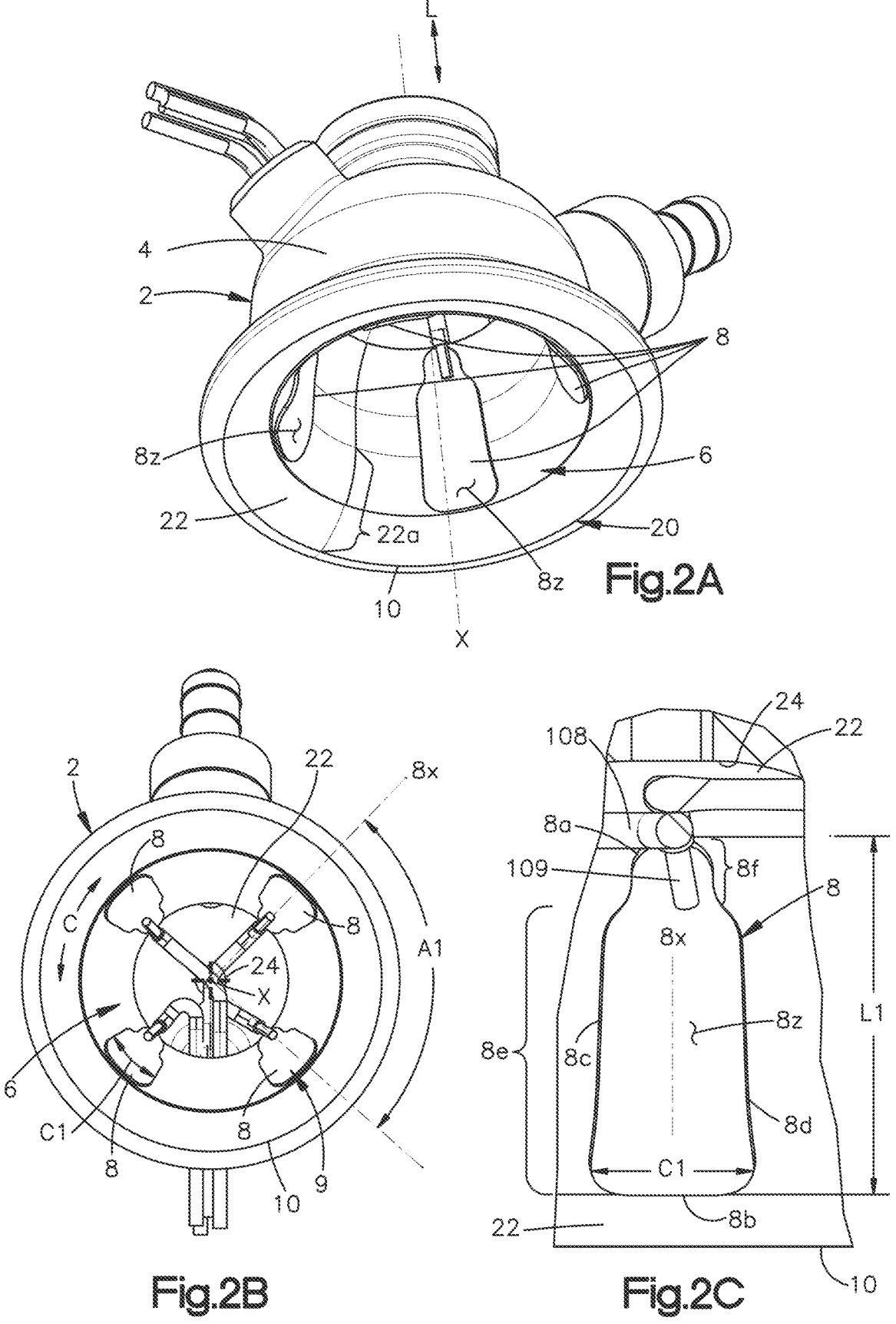
FIG. 2A is a perspective view of the vacuum cup illustrated in FIG. 1, showing a vacuum chamber of the cup and an array of electrodes located within the chamber, according to an embodiment of the present disclosure.
FIG. 2B is a bottom plan view of the vacuum cup illustrated in FIG. 2A, showing a pattern in which the electrodes are arrayed.
FIG. 2C is a plan elevation view of one of the electrodes illustrated in FIGS. 2A-2B

Referring now to FIGS. 2A-2B, the distal end 10 of the vacuum cup 2 defines at least one opening 20 leading into the vacuum chamber 6. The opening 20 can be circular as shown, although other opening shapes are within the scope of the present disclosure, as described in more detail below. The distal end 10 of the vacuum cup 2 (and thus also the opening 20) can be defined by the housing 4, which can define an interior surface 22 that extends from the distal end 10 of the housing to a proximal end 24 of the chamber 6. Accordingly, the chamber 6 also extends from the distal end 10 to the proximal end 24. The interior surface 22 at least partially defines the bounds of the vacuum chamber 6. The interior surface 22 preferably has a bell-shaped or "bell curve" geometry. A distal portion 22a of the interior surface 22 leading into the chamber 6 from the distal end 10 can have a tapered, radiused contour for reducing or otherwise mitigating damage, such as bruising, to the tissue at the periphery of the distal end 10 during use of the vacuum cup 2. The distal portion 22a can be referred to as a "lead-in" portion 22a of the interior surface 22. A proximal portion of the interior surface 22, such as at the proximal end 24 of the vacuum chamber 6, can be referred to as a "proximal end surface" or simply "end surface" of the vacuum chamber 6.

At least one and up to all of the electrodes 8 extend alongside the interior surface 22. As shown, the electrodes 8 can extend alongside the interior surface 22 between the distal end 10 and the proximal end 24 with respect to a longitudinal direction L oriented along a central axis X of the housing 4. The electrodes 8 of the present embodiment are preferably substantially rigid, although in other embodiments the electrodes 8 can have a measure of flexibility. The electrodes 8 can comprise thin layers of conductive material coupled to (e.g., via coating, deposition, bonding, and/or adhesion) associated substantially rigid, non-conductive support bodies, which can be constructed of plastics or other suitable non-conductive materials. The electrodes 8 can have surface geometries that are substantially conformal with the interior surface 22. The electrodes 8 can be elongate along a direction having a directional component along the longitudinal direction L. The electrodes 8 can also extend alongside the interior surface 22 along a circumferential direction C about the central axis X. As shown in FIGS. 2B-2C, the electrodes 8 can each define a circumferential dimension C1 (or "width" C1) measured along the circumferential direction C. The electrodes 8 can be positioned at regular angular intervals A1 about the central axis X. The angular intervals A1 can be measured from respective central axes 8x of the electrodes 8. As shown in FIG. 2B, the electrodes 8 can be positioned, for example, at ninety-degree angular intervals A1 about the central axis X. Thus, it can be said that the electrodes 8 are symmetrically spaced about the central axis X. It should be appreciated that other angular intervals A1 between electrodes 8 are within the scope of the present disclosure, as described in more detail below. Moreover, in some embodiments, the angular intervals A1 between electrodes 8 can vary along the interior surface 22. That is, the electrodes 8 can be spaced at irregular intervals about the central axis X. Furthermore, the electrodes 8 need not be symmetrically spaced about the central axis X.

As shown in FIG. 2C, each electrode 8 can define an electrode length L1 measured from a first end 8a to a second end 8b of the electrode 8 spaced from each other along the central electrode axis 8x. The electrodes 8 can also have first and second sides 8c, d spaced from each other to define an electrode width C1 along the circumferential direction C. Each electrode 8 can have an interior electrode surface 8z that is configured to contact the tissue surface 101 for delivering the one or more electroporation pulses. The interior electrode surface 8z can extend from the first end 8a to the second end 8b and from the first side 8c to the second side 8d of the electrode 8. Each electrode 8 can define a primary or "contact" portion 8e that extends from the second electrode end 8b towards the first electrode end 8a and also extends from the first to the second side 8a, b of the electrode 8. As shown, the electrode width C1 can be measured between the first and second electrode sides 8a, b, and need not be uniform along the contact portion 8e. The electrode length L1 and width C1 can each be in a range from about 1.0 mm to about 30 mm, more particularly in a range of about 2 mm to about 25 mm, and more particularly in a range of about 4 mm to about 20 mm. The electrodes 8 can define a thickness T1 (see FIG. 2F) in a range from about 0.0005 mm to about 2.000 mm. It should be appreciated that the electrode length L1 can be greater than, less than, or equivalent to the electrode width C1.

The portion of the internal electrode surface $8z$ within the contact portion $8e$ can be referred to as a "contact surface" $8z$ of the electrode. The contact surface $8z$ can extend arcuately and concentrically (i.e., can share the same centerpoint) with the interior surface 22 of the housing 4 in a reference plane orthogonal to the central axis X. The contact surface $8z$ can also have a curvilinear contour that is substantially conformal with the interior surface 22 in a direction along the central electrode axis $8x$. The contact surfaces $8z$ can be smooth, as shown, although in other embodiments the contact surfaces $8z$ can be textured to enhance grip against the tissue 102, such as with protrusions, dimples, knurls, microneedles, and/or a roughened surface, by way of non-limiting examples. In additional embodiments, a coating or adhesive can be applied to the contact surfaces $8z$, to improve the grip and/or conductivity between the electrode 8 and the tissue 102. The electrodes 8 can also define a secondary portion $8f$ that extends from the contact portion $8e$ to the first end $8a$ and can be configured to connect with a respective lead of the circuitry 108 for transmitting the electroporation pulse(s) to the electrodes 8.

Figures 2D, 2E, 2F:
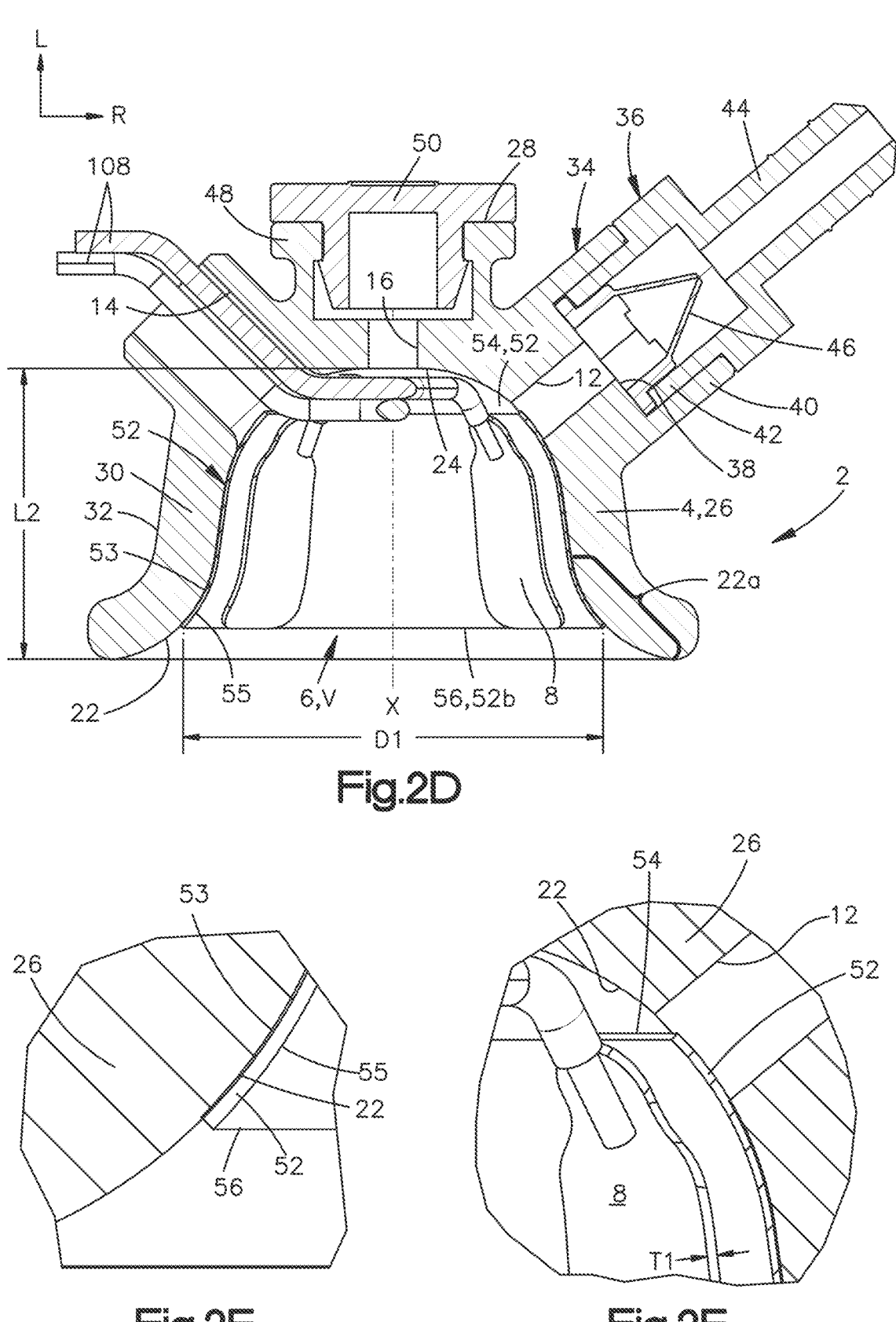
FIG. 2D is a sectional side view of the vacuum cup illustrated in FIG. 2A, taken along a central axis of the cup.
FIG. 2E is an enlarged sectional view of region 2E-2E illustrated in FIG. 2D.
FIG. 2F is an enlarged sectional view of region 2F-2F illustrated in FIG. 2D.

Referring now to FIG. 2D, the housing 4 can be include a housing body 26, which can be formed of a material that preferably has a measure of flexibility, such as a polymeric material, including polyetheretherketones (PEEK), polyphthalamides (PPA), polyethylenes, polycarbonates, polyetherimides (PEI), polyvinyl chlorides (PVC), polytetrafluoroethylenes (PTFE), polyamides, polyimides, polysiloxanes (silicone), polyethylene terephthalates, polyurethanes, crosslinked or non-crosslinked rubbers (elastomers), polyesters, by way of non-limiting examples. It should be appreciated that other bio-compatible and/or medical-grade materials can be employed for the housing body 26. The housing body 26 can optionally be a monolithic structure that defines the housing 4, although the housing body 26 need not be a monolithic structure and can instead include two or more body components coupled together to define the housing 4. The housing body 26 extends from a proximal end 28 to the distal end 10 along the longitudinal direction L. The housing body 26 also defines a wall 30 that extends from the internal surface 22 to an external surface 32 of the housing 4. The wall 30 extends circumferentially around an entire perimeter of the vacuum chamber 6.

The housing body 26 defines the ports 12, 14, 16. As shown, each of the first, second, and third ports 12, 14, 16 can be adjacent the proximal end 28 of the housing body 26 and remote from the distal end 10. Stated differently, the ports 12, 14, 16 can be located closer to the proximal end 28 than to the distal end 10 of the housing 4. The first port 12, which can also be referred to as a "vacuum port." extends from the vacuum chamber 6, through the housing body 26, and to a port coupling 34 for connection with a fitting member 36 that interconnects the vacuum port 12 with the vacuum source 106. The port coupling 34 can include a seat 38 and a tubular extension 40 that extends outwardly from the seat 38 and defines a receptacle, such that the seat 38 defines an inner end of the receptacle. The fitting member 36 can include a fitting member coupling 42 and a cannulated stem 44 extending therefrom. The fitting member coupling 42 can be a tubular extension that interconnects with the tubular extension 40 of the port coupling 34, such as by extending within the receptacle defined by the tubular extension 40) in mating fashion. A one-way valve member 46 can be positioned on the seat 38 (which can be referred to as a "valve seat"). The valve member 46 can extend from the valve seat 38 and within an interior space of the fitting member coupling 42, thereby being interposed in the fluid pathway between the vacuum port 12 and the cannulated stem 44 of the fitting member 36. The valve member 46 can be a duckbill valve, as shown, although in other embodiments the valve 46 can be ball valve or an umbrella valve, by way of non-limiting examples.

The second port 14 can extend opposite the first port 12 and can be configured to allow passage for the circuitry 108, such as wires, through the housing 4 and into contact with the electrodes 8 in the vacuum chamber 6. The second port 14 can also be configured to allow passage for one or more additional components, such as one or more tools and/or one or more sensors, through the housing 4 and into the vacuum chamber 6. While positioned inside the vacuum chamber 6, such tools and/or sensors can be positionally secured with respect to the tissue via vacuum pressure supplied to the chamber 6. The third port 16 can extend from the proximal end 24 of the chamber 6 and along the central axis X. The housing 4 can define a mounting formation 48 at an external end of the third port 16. The mounting formation 48 can be configured to mount a cap 50, such as a puncture stopper, over the third port 16. The mounting formation 48 and the puncture stopper 50 can have complimentary, mating geometries that provide an air-tight seal between the puncture stopper 50 and the third port 16. The puncture stopper 50 can be formed of a material that can be pierced by the hypodermic needle 18 allowing the needle 18 to inject the agent into the tissue 102 drawn into the vacuum chamber 6.

With continued reference to FIG. 2D, the electrode array 9 can be disposed on an insert 52, such as a sleeve, located in the chamber 6 and extending along the interior surface 22 of the housing 4. The sleeve 52, or at least an exterior surface 53 thereof, can have substantially the same profile geometry as the interior surface 22 of the housing 4. The sleeve 52 can be constructed of a flexible material, such as rubber, silicone, and thermoplastic elastomers, by way of non-limiting examples. As shown in FIG. 2E, the exterior surface 53 of the sleeve 52 can adhere directly to the interior surface 22 of the housing 4 via a friction fit, although one or more adhesives can optionally be employed to attach the sleeve 52 to the interior surface 22. The sleeve 52 can extend from a first or proximal end 54 adjacent the proximal end 24 of the vacuum chamber 6 to a second or distal end 56 adjacent the distal end 10 of the housing 4. The distal end 56 of the sleeve 52 can extend within the lead-in portion $22a$ of the interior surface 22 of the housing 4. The first end 54 can define a proximal opening $52a$ of the sleeve 52, which can be concentric with the central axis X and a distal opening $52b$ of the sleeve 52. As shown more clearly in FIG. 2F, the first end 54 of the sleeve 52 can partially occlude the first port 12, and can also partially occlude the third port 16 while allowing passage for the circuitry 206 into the vacuum chamber 6. Thus, the sleeve 52 can be employed as a mechanism for controlling or at least affecting vacuum pressure within the chamber 6.

The vacuum chamber 6 defines a chamber volume V, which is defined between the proximal end 24 of the chamber 6 to the opening 10 along the longitudinal direction L, and can also be at least partially defined by the interior surface 22 of the housing body 26, such as along a direction substantially perpendicular to the longitudinal direction L. In the illustrated example, the direction perpendicular to the longitudinal direction L is a radial direction R that intersects the central axis X. The chamber volume V can also be at least partially defined by the sleeve 52, such as along the radial direction R. The chamber 6 can have a depth L2 measured from the proximal end 24 of the chamber 6 to a reference plane circumscribing the distal end 10 of the housing 4. The chamber depth L2 can be in a range from about 1.0 mm to about 50.0 mm, more particularly in a range of about 3 mm to about 20 mm, and more particularly in a range from about 5 mm to about 17 mm. The chamber 6 also has a base width, such as a base diameter D1, which can be measured along the radial direction R at the distal end 56 of the sleeve 52. The chamber diameter D1 can be in a range from about 1.0 mm to about 50.0 mm, particularly in a range of about 3.0 mm to about 20.0 mm, and more particularly in a range from about 6.0 mm to about 17.0 mm. In the present embodiment, the chamber diameter D1 can be measured between opposed portions of an interior surface 55 of the sleeve 52 at the distal end 56 thereof. In other embodiments, the sleeve 52 can be omitted and the electrodes 8 can be attached directly to the interior surface 22 of the housing 4, for example, by being embedded or at least partially embedded within the housing wall 30. In such embodiments, the vacuum chamber 6, and thus the chamber volume V, can be at least partially defined by the interior surface 22 of the housing 4 and the interior surfaces 8z of the electrodes 8. Accordingly, in such embodiments, the chamber diameter D1 can be measured between opposed portions of the interior surface 22 of the housing 4 at the distal ends 8b of the electrodes 8.

Figures 3A, 3B, 3C, 3D, 3E, 3F, 3G, 3H, 3I, 3J, 3K, 3L:
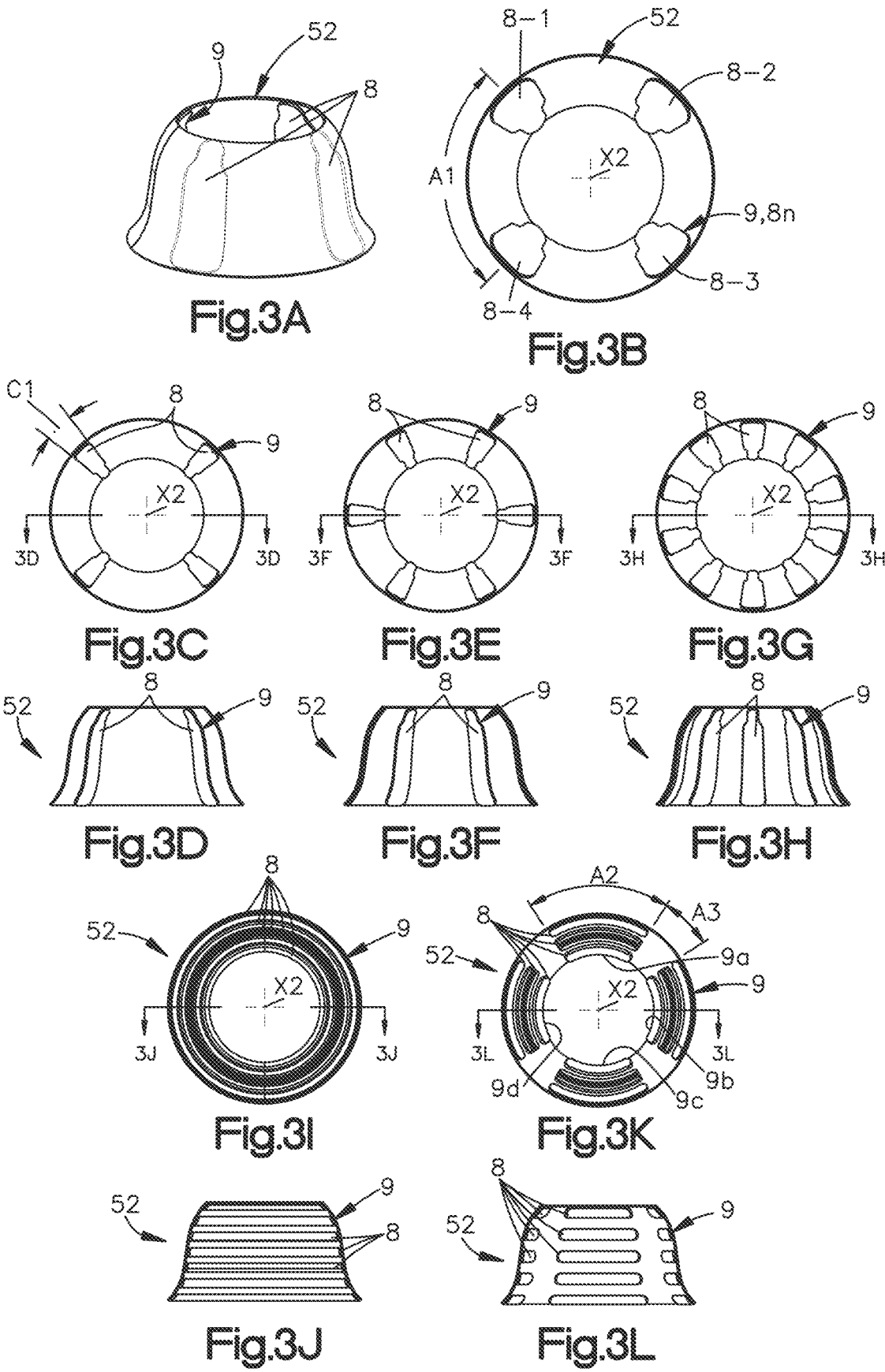
FIG. 3A is a perspective view of a sleeve that carries the electrodes and is insertable within the vacuum chamber illustrated in FIG. 2A.
FIG. 3B is a bottom plan view of the sleeve illustrated in FIG. 3A.
FIGS. 3C-3D, 3E-3F, 3G-3H, 3I-3J, and 3L are respective bottom plan and sectional side views of sleeves having alternative electrode array patterns, according to additional embodiments of the present disclosure.

Referring now to FIGS. 3A-3B, the sleeve 52 can carry each of the electrodes 8 and thus the electrode array 9. Accordingly, the sleeve 52 can also be referred to as an electrode array base, support, or substrate. In the illustrated embodiment, the electrode array 9 defines an electrode pattern that includes a first electrode 8-1, a second electrode 8-2, a third electrode 8-3, and a fourth electrode 8-4, such that the first through fourth electrodes 8-1, 8-2, 8-3, 8-4 are positioned at ninety-degree intervals A1 about a central axis X2 of the sleeve 52 (which is substantially coextensive with the central axis X of the cup housing 4 when the sleeve 52 is inserted therein). The electrode array 9 of the present embodiment can be characterized as having a total number of electrodes 8n that is four (4) electrodes 8. The total number of electrodes 8n can also be referred to herein as the "total number" 8n or simply "total" 8n. The sleeve 52 can also be interchangeable with other sleeves 52 having different electrode array 9 patterns and configurations, such as for producing electrical fields having different characteristics within the tissue 102 drawn into the vacuum chamber 6. For example, as shown in FIGS. 3C-3D, a sleeve 52 can have an electrode array 9 that includes four electrodes 8 spaced at ninety-degree intervals about a central axis X2 of the sleeve 52, as above; however the electrodes 8 can each have a narrower circumferential dimension C1, and thus also a lesser cumulative surface area, than the electrodes 8 in the embodiment described above. As shown in FIGS. 3E-3F, a sleeve 52 can have an electrode array 9 that includes six (6) electrodes 8 spaced at sixty-degree intervals about the central axis X2. As shown in FIGS. 3G-3H, the electrode array 9 can include ten (10) electrodes 8 spaced at thirty-six-degree intervals about the central axis X2.

As shown in FIGS. 3I-3J, the electrode array 9 can include seven (7) electrodes 8 spaced from each other along the longitudinal direction L and each extending around an entire circumference of sleeve 52. Such an array 9 design can allow the electrodes 8 to be pulsed or "fired" in sequence(s) that drive the resulting electroporation field "upward" and/or "downward" through the tissue volume gripped by the vacuum cup 2.

As shown in FIGS. 3K-3L, the electrode array 9 can include a plurality of circumferentially elongate electrodes 8, including four (4) subsets 9a-d of circumferentially elongate electrodes 8. The electrodes 8 within each subset 9a-d can be substantially longitudinally aligned with each other, and each subset 9a-d can be circumferentially spaced from each adjacent subset 9a-d of electrodes 8. In the present example, each subset 9a-d of electrodes 8 can include five (5) longitudinally spaced electrodes 8. Accordingly, the sleeve 52 can include a total of twenty (20) circumferentially elongate electrodes 8. In the present embodiment, the electrodes 8 within each subset 9a-d can have an angular span A2 in a range of about 1 degree to about 90 degrees about the central axis X2, with an inter-electrode span A3 in a range of about 1 degrees to about 90 degrees between adjacent subsets 8a-d. Spacing the subsets 9a-d circumferentially from each other allows, among other things, the subsets 9a-d to be fired (or otherwise driven by a current source or voltage source) independently of each other. This can help ensure that each of the regions within the tissue volume adjacent to and associated with the subsets 9a-d (in this embodiment, such tissue regions can be characterized as "quadrants" of the tissue volume) receives electroporation field coverage, which results in a more symmetrical electroporation field and can avoid an instance where localized differences in tissue conductivity within the tissue volume biases the electroporation field away from one or more of the regions within the tissue volume.

Moreover, the circumferentially spaced subsets 9a-d shown in FIGS. 3K-3L can also allow the generation of unique directional electroporation fields within the tissue volume, such as for electro-pulsing the cells from multiple angles (i.e., exposing the cells to electroporation field gradients along different directions) in subsequent pulses, which can electropermeabilized the cells more efficiently than electro-pulsing the cells from a single direction. It should be appreciated that such multi-directional electroporation fields can also be generated by the various array designs of FIGS. 3A-3H. However, the circumferentially spaced subsets 9a-d of FIGS. 3K-3L also allow the electrodes 8 to fire not only laterally and/or circumferentially across the tissue volume but also "upward" and/or "downward" through the tissue volume. By increasing the amount of electrodes 8 in the array 9, the amount of possible unique pulse patterns can also be increased, also allowing more homogeneous electroporation field coverage considering that the electroporation fields are concentrated at the contact surfaces 8z of the electrodes 8.

It should be appreciated that the various electrode array 9 patterns described above are provided by way of non-limiting examples, and that other electrode array 9 configurations are within the scope of the present disclosure. For example, one or more of the parameters of the electrode arrays 9 described above can be tailored as needed, including but not limited to: the quantity of electrodes 8 in each array 9; electrode length L1 and width C1; and inter-electrode spacing. These parameters can affect the three-dimensional (3D) shape of the electrical field (and thus also the 3D shape of the electroporation field). Stated differently, the size, shape, and arrangement of the electrodes 8 can be tailored as needed to focus the distribution of the electric field within the tissue 102 in a manner providing an enhanced electroporation treatment.

With reference to FIGS. 4A-4F, an example method of using the vacuum cup 2 to provide electroporative treatment to adipose tissue 103 will now be described.

As shown in FIG. 4A, a physician can place the distal end 10 of the vacuum cup 2 onto the outer surface 101 of the patient's skin 104 at a location overlaying a target zone 105 of the adipose tissue 103. The target zone 105 can be pre-selected or can be a result of the vacuum cup 2 placement. Preferably, the physician places an entire circumference of the distal end 10 in contact with the skin 104.

As shown in FIG. 4B, the physician can apply a pulse of vacuum pressure (also referred to herein as a "vacuum pulse") to the vacuum chamber 6, particularly by activating the vacuum source to create vacuum pressure in a range of about −0.1 psi to about −14.7 psi, and more preferably in a range of about −3 psi to about −14.7 psi, within the vacuum chamber 6 sufficient to draw a volume or "mound" 140 of the tissue 102 into the chamber 6 and into contact with the contact surfaces 8z of the electrodes 8. It should be appreciated that the vacuum pressure magnitudes included throughout this disclosure refer to such pressures relative to atmospheric pressure as measured at sea level. The contact pressure between the tissue mound 140 (particularly the skin layer 104 thereof) and the interior surface 22 of the cup 2 can be in a range from about 0.1 psi to about 200 psi. In this manner, the vacuum cup 2 draws at least a portion of the target zone 105 into a treatment zone 107 defined by the cup 2. In the present example, the tissue mound 140 includes the skin 104 and adipose tissue 103. For purposes of the present disclosure, the treatment zone 107 is defined as the portion of the tissue volume (such as the tissue mound 140) that extends between the electrodes 8. As shown, a bottom boundary 107a of the treatment zone 107 can be defined by an imaginary path extending along and between the second ends 8b of the electrodes 8. As such, after the tissue mound 140 is drawn into the vacuum chamber 6, the treatment zone 107 of the present embodiment will contain at least a portion of the tissue mount 140 and at least a portion of an injection site 109 (see FIG. 4C) therein. In the illustrated embodiment, the tissue positioned within the treatment zone 107 during treatment is limited to the skin layer 104, and the adipose layer 103. In other embodiments, the treatment zone 107 can include a smooth muscle layer 111. Preferably, the treatment zone 107 does not include any skeletal muscle therein. As described above, the vacuum pressure is preferably sufficient to provide the vacuum cup 2 with a sturdy grip on the tissue mound 140, thereby retaining the relative position between the vacuum cup 2 and the tissue mound 140. Although the illustrated embodiment illustrates the skin 104 of the tissue mound 140 being placed in direct contact with the contact surfaces 8z of the electrodes 8, it should be appreciated that additional substances, such as conductive gel, can be utilized to improve electrical communication between the electrodes 8 and the skin 104.

As shown in FIG. 4C, the physician can inject an agent into the adipose tissue 103 of the mound 140. To perform the injection, the physician can penetrate the hypodermic needle 18 through the puncture stopper 50, along the third port 16, through the skin 104, and into the adipose tissue 103 within the chamber volume V. The physician can then inject the agent into an injection site within the adipose tissue 103 and subsequently withdraw the hypodermic needle 18 from the vacuum cup 2. The inventors have observed, surprisingly and unexpectedly, that the injectate 142 expelled from the hypodermic needle 18 into the adipose tissue 103 disperses toward the skin 104 responsive to the vacuum pressure, as opposed to remaining in a pooled bolus 142a in the adipose tissue 103. Accordingly, the physician can inject the injectate 142 near or at the bottom of the treatment zone 107, or even slightly below the treatment zone 107, and allow the vacuum pressure to effectively pull the injectate 142 upwardly into the treatment zone 107, even allowing the injectate 142 to become concentrated in the treatment zone 107. The inventors also believe, based on observations during testing, that the vacuum pressure can be manipulated to help mix the injectate 142 with in vivo fluids, extracellular components, and cells, and to retain the injectate 142 in the treatment zone 107 in a manner enhancing the injectate 142 latency therein, thereby increasing the transfection.

It should be appreciated that, in some embodiments, the needle 18 can remain inserted in the tissue 102 after the injection and at least a portion of the needle 18 can comprise a sensor 152 for detecting a parameter of the tissue 102, such as an electrical parameter, during or after electroporation, as described in more detail below.

As shown in FIG. 4D, the physician can deliver one or more electroporation pulses to the tissue mound 140. In particular, the physician can cause the signal generator 112 to deliver an electroporation signal in the form of one or more electroporation pulses to the electrodes 8, which in turn deliver the one or more electroporation pulses to the tissue 102 in contact with the electrodes 8, thereby creating, in the illustrated embodiment, an electroporation field 144 within the adipose tissue 103 in the treatment zone 107. The electroporation field 144 substantially causes reversible portion in the cellular membranes of cells (e.g., adipose cells) in the treatment zone 107, causing transfection of the injectate into the temporarily porated cells. In this manner, the electroporation field 144 creates a transfection zone within the treatment zone 107. The electroporation field 144 produced by the electrodes 8 of the present embodiment has a substantially spherical shape. It should be appreciated that the electroporation field 144 is a sub-region of an electric field 145 produced by the electrodes 8 during pulse delivery.

The one or more electroporation pulses delivered by the electrodes 8 can have an electric potential (voltage) in a range of about 5 V to about 1000 V (1 kV).

The one or more electroporation pulses can have an electric current (amperage) in a range of about 0.01 Amp to about 2.0 Amps.

The one or more electroporation pulses can each have a duration in a range of about 100 microseconds to about 500 milliseconds.

The quantity of electroporation pulses can be in a range of 1 pulse to about 10 pulses.

For multi-pulse deliveries, each electroporation pulse can be separated in time from adjacent pulses by a pulse delay in a range of about 1 millisecond to about 1 second.

In some embodiments, the electroporation signal can include 3 pulses at approximately 200 V of approximately 100 milliseconds in duration with 200 milliseconds of delay between pulses. In other embodiments, the electroporation signal can include 3 pulses at approximately 50 V of approximately 100 milliseconds in duration with 200 millisecond delay between pulses. In still other embodiments, the electroporation signal can include 10 pulses at approximately 50 V of 100 milliseconds in duration with 1 second delay between pulses. In still other embodiments, the electroporation signal can include 8 pulses of 75 V of approximately 100 milliseconds of duration with approximately 100 milliseconds of delay between pulses. In still other embodiments, the electroporation signal can include 3 pulses of between approximately 500 V and approximately 1000 V of approximately 10 microseconds and approximately 100 microseconds duration with approximately 100 milliseconds to approximately 1 second delay between pulses. It should be appreciated that the foregoing electroporation signals are provided as non-limiting examples, particularly for reversible pore formation for DNA delivery into cells. It should also be appreciated that the embodiments disclosed herein can be adapted for providing other types of treatment, including delivering other types of agents into cells, such as for delivering small molecules into cells, electrochemotherapy, and irreversible electroporation, by way of non-limiting examples.

In treatments involving a plurality of electroporation pulses, the pulses can be delivered by the electrodes 8 in a pulse sequence or pattern, in which: a first electroporation pulse is delivered by a first positive subset of the electrodes 8 through the tissue 102 to a first negative subset of the electrodes 8: a second electroporation pulse is delivered by a second positive subset of the electrodes 8 through the tissue 102 to a second negative subset of the electrodes 8; and so forth, up to and including the final electroporation pulse of the treatment. During each electroporation pulse, each positive and negative subset of electrodes 8 can range from a single electrode 8 to any combination of electrodes 8 that is at least one less (i.e., 8n-1) than the total number of electrodes 8n of the array 9. The electroporation pulse pattern can be delivered according to a programmed sequence, which can be input by a user to the controller 114 (such as via the user interface 120). Moreover, the sequence of electroporation pulses can optionally be delivered in a decentralized pattern. In such decentralized pattern sequences, each pulse of the plurality of electroporation pulses can be delivered between a set of at least two of the electrodes 8, and each subsequent pulse of the plurality of electroporation pulses is delivered by a different set of at least two electrodes 8. Decentralized electroporation pulse patterns can minimize, or preferably eliminate, the occurrence of electroporation-related heat stress on the tissue 102 being electroporated, and can enhance the homogeneity of the electric field generated within tissue 102.

The vacuum cup 2 can be configured to sense, measure, or otherwise detect one or more electrical parameters of the tissue 102 during electroporation pulse delivery and relay the detected information back to the controller 114 for diagnostics and feedback. The electrical parameters detected in the tissue 102 can include voltage, current, impedance, and/or resistance, by way of non-limiting examples. One technique for detecting such parameters during electroporation pulse delivery is to cause at least one of the electrodes 8 to measure the desired electrical parameter during the pulse. Such an electrode 8 can be characterized as a sensing electrode 8 or simply a "sensor." The sensing electrode 8 can be neutral during the pulse. By way of a non-limiting example of a decentralized electroporation pulse pattern sequence, each pulse of the plurality of electroporation pulses can be delivered between a set of at least two of the electrodes 8 while at least one other electrode 8 is a sensing electrode 8 that is neutral and measures the electrical parameter of the tissue 102, such as impedance, and wherein each subsequent pulse of the plurality of electroporation pulses is delivered by a different set at least two electrodes 8 while at least one electrode 8 is a sensing electrode 8 that is neutral and measures the electrical parameter. The at least one neutral electrode 8 can alternative from pulse to pulse, although the same electrode 8 (or set of electrodes 8) can remain neutral in consecutive pulses. Alternatively, during an electroporation pulse, at least one electrode 8 of the array 9 can actively deliver the pulse while also measuring an electrical parameter of the tissue 102.

Another optional technique for detecting electrical parameters during electroporation pulse delivery is to employ at least one separate sensor for detecting the parameter. The separate sensor can be a non-invasive sensor 150, such as a contact sensor 150, for example, as shown in FIG. 4D. The contact sensor 150 is configured to measure the parameter and communicate information about the measured parameter to the controller 114. The contact sensor 150 can be inserted into the vacuum chamber 6 through a port, such as the second port 14. The physician can place the contact sensor 150 into contact with the tissue 102, such as at the skin 104, where the contact sensor 150 can measure the parameter. In other embodiments, the separate sensor can be an invasive sensor 152, such as a probe-type sensor 152. In one such example of a probe-type sensor 152, the sensor 152 can be a portion of the injection needle 18, such as a distal tip region thereof (see FIG. 4C), which can be in electrical communication with the controller 114 for relating information about the measured parameter to the controller 114. It should be appreciated that multiple sensors, including one or more non-invasive sensors 150 and one or more probe-type sensors 152 can be employed during a treatment to relay information regarding a single electrical parameter or multiples electrical parameters of the tissue 102 to the controller 114.

The electrical parameter information received by the controller 114 can be employed for performance diagnostic purposes and/or for active feedback control of the electroporation signal delivered to the electrodes 8, and thus delivered to the tissue 102. For example, to provide active feedback control, the one or more sensors 8, 150, 152 can measure one or more respective electrical parameters in the tissue 102 and communicate information about the parameter(s) to the controller 114. The processor 116 can run software incorporating the parameter information, such as by executing one or more algorithms that incorporate the parameter information to process or otherwise derive outputs, such as control commands for controlling the electroporation pulse. The algorithm(s) can also employ parameter data retrieved from the computer memory 118. It should be appreciated that the control commands derived from the algorithm(s) can adjust the electroporation pulse in real time, such as substantially instantaneously for electroporation purposes, based on the parameter information from the sensor(s) 8, 150, 152. In this manner, the electroporation system 100 can employ the sensor(s) 8, 150, 152 in an active feedback loop for constant control and adjustment of the electroporation pulse as needed to achieve a desired electroporative treatment result in the targeted tissue 102. The techniques and/or electronic components for performing such feedback control can be employed as more fully disclosed in U.S. Pat. No. 9,452,285, issued Sep. 27, 2016, entitled "Electroporation Devices and Methods of Using Same for Electroporation of Cells in Mammals" (the '285 Reference) and U.S. Patent Publication No. 2011/0009807 A1, published Jan. 13, 2011, entitled "Variable Current Density Single Needle Electroporation System and Method" (the '807 Reference), the entire disclosure of each of which is hereby incorporated by reference herein.

As shown in FIG. 4E, subsequent to the one or more electroporation pulses, the physician can return the pressure within the vacuum chamber 6 to atmospheric pressure, allowing the vacuum cup 2 to release the tissue 102, which can return to its anatomical shape. The transfected adipose cells can define a transfection zone 105z in the adipose layer 103.

Referring now to FIG. 4F, one of the significant benefits of the vacuum cup 2 disclosed herein is that it, in connection with the vacuum source 106, allows the physician to control the volume of tissue 102 (i.e., the size of the mound 140) drawn into the treatment zone 107 for electroporative treatment. Accordingly, if the target zone 105 resides solely in the skin layer 104, the physician can apply a vacuum pressure to the vacuum chamber 6 necessary to draw the skin layer 104 into the chamber volume V and into contact with the electrodes 8, such as at the distal ends 8b thereof. If the target zone 105 resides in the adipose layer 103, the physician can apply an increased vacuum pressure necessary to draw the adipose layer 103 into the treatment zone 107. If the target zone 105 resides in a muscle layer, such as a smooth muscle layer, the physician can apply a further increased vacuum pressure, and an even further increased vacuum pressure if the target zone 105 resides in a skeletal muscle layer. It should be appreciated that the target zone 105 can reside in a single layer of tissue (e.g., the skin layer 104 or adipose layer 103) or can reside in multiple tissue layers, including the skin layer 104, adipose layer 103, and optionally a smooth muscle layer. The vacuum pressure can be controlled as needed according to the depth of the target zone 105.

Another significant benefit of the vacuum cup 2 of the present disclosure is that the vacuum cup 2, in connection with the vacuum source 106, allows the physician to apply a plurality of vacuum pulses to the tissue 102 to enhance interaction between the tissue and the injectate, including the favorable in vivo fluid dispersion mechanisms described above. Vacuum pulses can be applied before, during, and/or after injection, and can also be applied before, during, and/or after electroporation. The vacuum pulses can be imparted in a quantity in a range of 1 pulse to 20 pulses, and each pulse can have a duration in a range of about 0.1 seconds to about 30 seconds. The vacuum pulses can also be applied in varying vacuum pressures and/or durations (and/or varying time between pulses) to achieve a desired result.

The inventors have made a number of surprising and unexpected observations in connection with the vacuum cups 2 of the present disclosure. For example, the inventors observed an unexpected and surprising increase in immune response in test subjects treated with vacuum-assisted electroporation using the vacuum cup 2. This result was surprising and unexpected because the inventors' initial aim was to employ the vacuum cup 2 for the primary purpose of achieving a more secure grip on the subject tissue relative to the grip provided by prior art caliper-type electroporation devices. The inventors were not able to explain the increased immune responses they had measured in test subjects treated with the vacuum cup 2 as a mere result of enhanced positional stability between the vacuum cup electrodes 8 and the tissue. Of note, the inventors also observed an unexpected and surprising amount of cellular infiltration at treatment sites treated with the vacuum cup 2. After some treatments utilizing the vacuum cup 2, the inventors observed bruising and discoloration on the skin characteristic of erythermas and/or hematomas, the latter involving blood dispersion through burst capillaries.

While not wanting to be bound by any particular theory, the inventors believe that the surprising increases in immune response and cellular infiltration are likely related. Moreover, the inventors believe that the increased cellular infiltration is at least partially driven by the natural secretion of chemical signals from burst capillaries and nearby leukocytes in the treatment zone that attract additional cells, such as additional leukocytes, to responsively migrate to the treatment zone. The inventors also believe that the observed cellular infiltration might be at least partially driven by an inflammatory response. The inventors further believe, based on the observed dispersion of the injectate through the tissue responsive to vacuum pressure, that in vivo fluids outside the treatment zone 107 are mechanically pulled into the treatment zone 107 responsive to the vacuum pressure.

Referring now to FIGS. 5A-5D, an embodiment of a vacuum cup 502 employing flexible electrodes 508 will now be described. The vacuum cup 502 of the present embodiment is similar the vacuum cups 2 described above. Accordingly, like references numbers as used above denote common features in the present embodiment. For the sake of brevity, the following description focuses on differences between the vacuum cup 502 of the present embodiment and the vacuum cups 2 described above.

As shown in FIGS. 5A-5B, the vacuum cup 502 has a housing body 526 that defines an interior surface 522 that partially defines a vacuum chamber 506. The housing body 526 also defines a plurality of relief ports 560 that extend from an external surface 532 of the housing body 526 to a plurality of channels 562 defined in the interior surface 522 of the housing body 526. The channels 562 can include a proximal channel 562 and a distal channel 562 spaced from each other along the longitudinal direction L. The channels 562 can each extend annularly along an entire revolution about the central axis X, although in other embodiments one or more of the channels 562 can extend annularly less than a full revolution about the central axis X.

The vacuum cup 502 includes a flexible sleeve 552 that resides within the vacuum chamber 506 and carries a plurality of electrodes 508 arranged in an electrode array 509. The flexible sleeve 552 has an exterior surface 553 that is attached to the interior surface 522 of the housing body 526. The flexible sleeve 552 overlies the channels 562 in a manner providing a flexible barrier or membrane between the channels 562 and the vacuum chamber 6. The electrodes 508 are disposed on an interior surface 555 of the sleeve 552. The sleeve 552 can also carry circuitry, such as wired circuitry or printed circuitry, for example, for providing electrical communication between the electrodes 508 and the controller 114. The electrodes 508 of the present embodiment can be circumferentially elongate, similar to the electrodes 8 described above with reference to FIGS. 3K-3L. One or more and up to each of the electrodes 508 overlies at least one of the channels 562 and is constructed of a flexible material. The electrode material can be a metal, such as copper, stainless steel, and gold, by way of non-limiting examples. Alternatively or additionally, the electrode material can include a conductive polymer or a carbon allotrope, such as graphene, which can include carbon nanotubes, by way of non-limiting examples. In other embodiments, the electrodes 508 can have non-conductive cores coated with a conductive material, such as those described above.

The electrode array 509 can including four (4) subsets 509a-d of electrodes 508. The electrodes 508 within each subset 509a-d can be substantially aligned along the longitudinal direction L, and each subset 509a-d can be spaced from each adjacent subset 509a-d along the circumferential direction C. The subsets 509a-d can be regularly spaced from each other, such as at ninety-degree intervals about the central axis X. In the illustrated example, each subset 9a-d includes a proximal electrode 508 and a distal electrode 508 longitudinally spaced from each other, providing the array 509 with a total of eight (8) electrodes 508. The electrodes 508 of the array 509 can also be characterized as being arranged in a proximal annular row of electrodes 508 that overlies the proximal channel 562 and a distal annular row of electrodes 508 that overlies the distal channel 562. As described above, the electrodes 508 are connected to circuitry that provides electrical communication between the electrodes 508 and the controller 114. It should be appreciated that the circuitry of the electrode array 509 can be configured so that the controller 114 can control parameters of the electroporation pulse(s) to each subset 509*a-d* of electrodes 508 individually, and can further control parameters of the electroporation pulse(s) to each electrode 508 individually within each subset 509*a-d*.

Referring now to FIGS. 5C-5D, the flexible sleeve 552 and the electrodes 508 are configured to flex inwardly into the vacuum chamber 6 (toward the central axis X) upon the application of vacuum pressure within the chamber 6, increasing contact between contact surfaces 508*z* of the electrodes 508 and tissue drawn into the chamber 6. The relief ports 560 provide fluid communication between the channels 562 and the exterior of the vacuum cup 502, thereby allowing the pressure within the channels 562 to remain substantially at atmospheric pressure. In this manner, vacuum pressure within the chamber provides a pressure gradient in the sleeve 552 wall between the chamber 6 and the channel 562 allowing the sleeve 552, and the electrodes 508 thereon, to flex inwardly into the chamber 6.

Referring now to FIG. 6A-6D, electrodes 608 for positioning within the vacuum chamber 6 of a vacuum cup 2, 502 can include a plurality of protrusions 664, which can be defined by a contact surface 608*z* of the electrode 608. Similar to the manner described above, the electrodes 608 extend from a first end 608*a* to a second end 608 along a central axis 608*x* of the electrode 608. The electrodes 608 can be elongate along a direction oriented along the central axis 608*x*. The electrodes 608 can also extend from a first side 608*c* to a second side 608*d* along a transverse axis 608*y* of the electrode 608. The contact surface 608*z* can include a base portion 665 that is substantially smooth, and the protrusions 664 can extend outwardly from the base portion 665 (i.e., inwardly into the chamber 6). The base portion 665 can be substantially planar, as shown, although in other embodiments the base portion 665 can have a curvilinear contour that is substantially conformal with the interior surface 22 of the cup housing 4. By extending outwardly from the base portion 665, the protrusions 664 can increase the contact area between the contact surface 608*z* of the electrode 608 and the tissue drawn into the chamber 6. During use, the protrusions 664 can press into the tissue 102 in a manner disrupting and altering the top layer of the skin 104, improving the electric field distribution within the target tissue. More specifically, the protrusions 664 increase the magnitude of the electric field formed within the tissue 102 for a given input voltage, as described more fully in International (PCT) Patent Publication No. WO 2018/ 057900 A1, published Mar. 29, 2018, entitled "Method and Device for Minimally Invasive In Vivo Transfection of Adipose Tissue Using Electroporation" (the '900 Reference), the entire disclosure of which is hereby incorporated by reference herein.

Figures 6A, 6B, 6C, 6D:
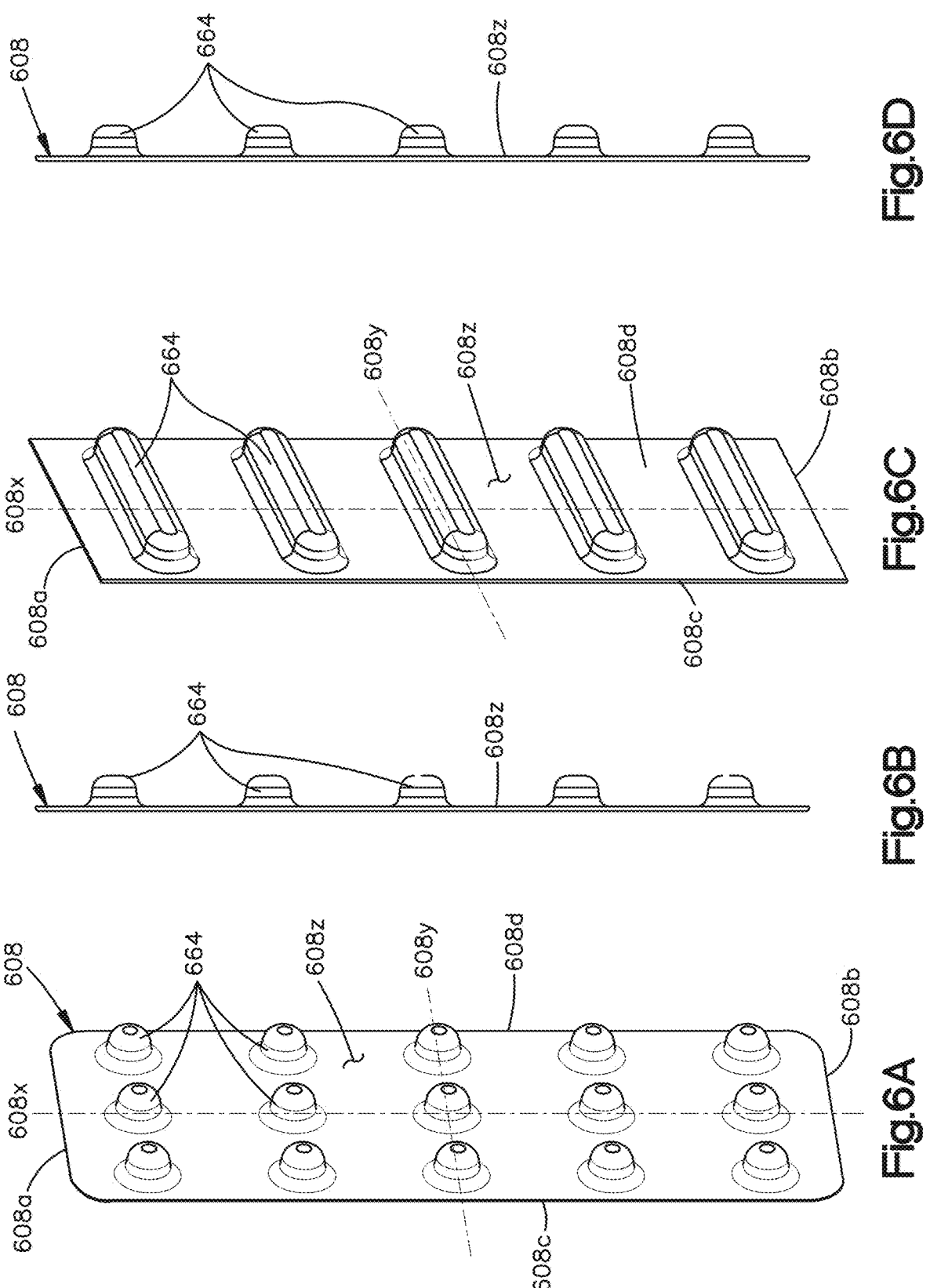
FIGS. 6A and 6B are respective perspective and side elevation views of an electrode having a contact surface that defines protrusions, according to an embodiment of the present disclosure.
FIGS. 6C and 6D are respective perspective and side elevation views of an electrode having a contact surface that defines laterally-elongate protrusions, according to another embodiment of the present disclosure.

As shown in FIGS. 6A-6B, the protrusions 664 can have convex, arcuate, dome-like geometries. The protrusions 664 can be arranged in columns and rows of protrusions 664. As shown in FIG. 6C, the protrusions can be elongated along a direction oriented along the transverse axis 608*y*. As shown in FIGS. 6B and 6D, the protrusions 608 shown in FIGS. 6A and 6C can have similar side profiles. It should be appreciated that other protrusion geometries, including pointed, conical, frusto-conical, pyramidal, and the like, are within the scope of the present disclosure. It should also be appreciated that the electrode 608 can be configured for positioning with the chamber 6 so as to be elongate along the longitudinal direction L of the vacuum cup 2, elongate along the circumferential direction C of the vacuum cup 2, or elongate along a direction oblique to the longitudinal and circumferential directions L, C.

Various parameters of the vacuum cups 2, 502 described herein, such as chamber depth L2, chamber diameter D1, and cup geometry, such as cross-sectional shape in a reference plane orthogonal to the central axis X, and/or the shape of the opening 20, can be tailored as needed to achieve a desirable electroporation treatments, such as across a broad spectrum of mammals and skin anatomies. For example, vacuum cups of the present disclosure can have non-circular openings and/or chamber geometries, such as polygonal openings and/or chamber geometries, by way of non-limiting examples. With reference to FIGS. 7A-7E, a vacuum cup 702 having a triangular opening and chamber geometry will be described. With reference to FIGS. 8A-8C, a vacuum cup 802 having a rectangular opening and chamber geometry will be described. In such embodiments, chamber dimension D1 can be referred to as the "chamber width" D1.

Figures 7A, 7B, 7C:
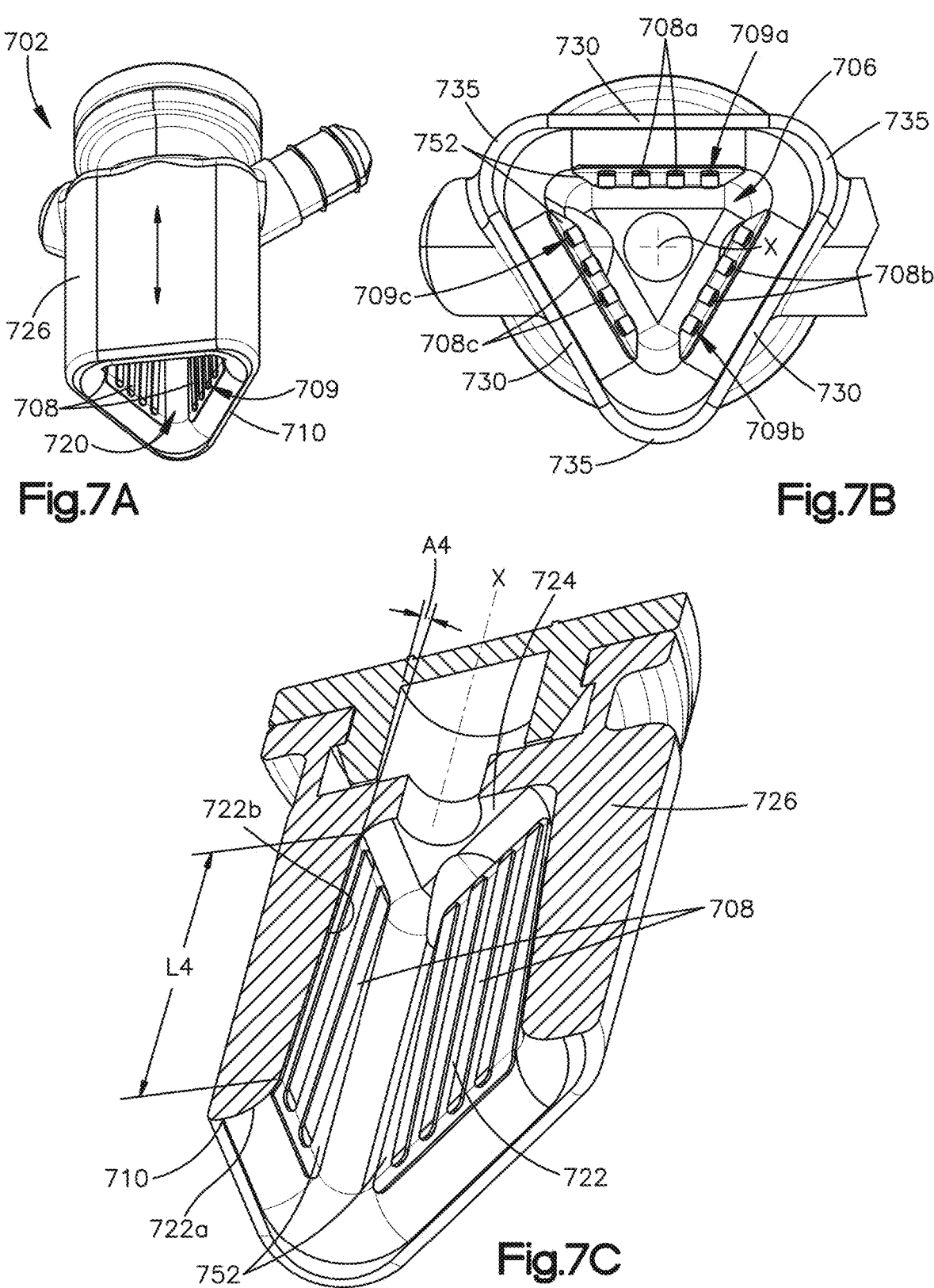
FIG. 7A is a perspective view of a vacuum cup having a triangular distal opening and vacuum chamber geometry, according to an embodiment of the present disclosure.
FIG. 7B is a bottom plan view of the vacuum cup illustrated in FIG. 7A.
FIG. 7C is a sectional perspective view of the vacuum cup illustrated in FIG. 7A, taken along a central axis of the cup.
Figures 8A, 8B, 8C:
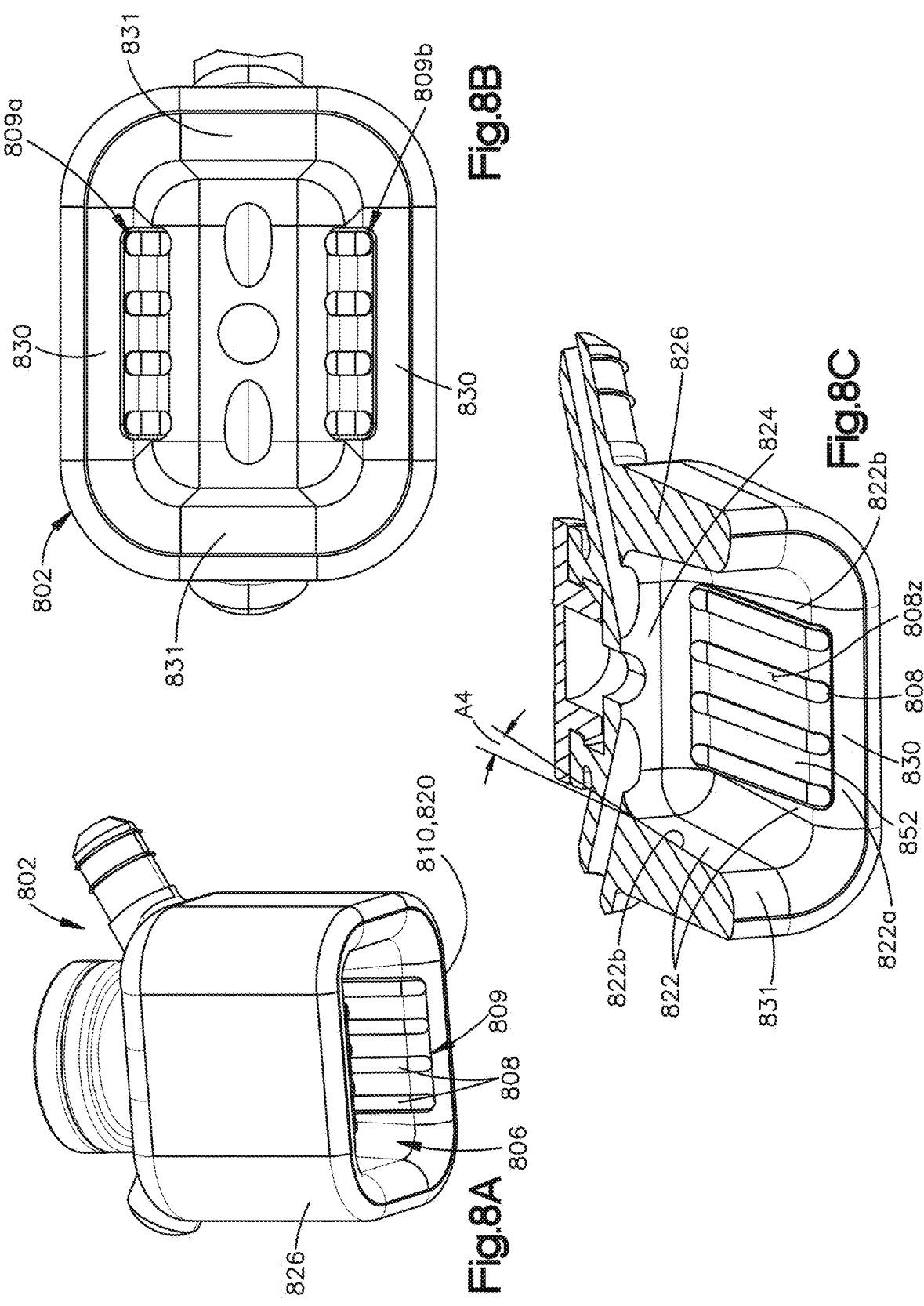
FIG. 8A is a perspective view of a vacuum cup having a rectangular distal opening and vacuum chamber geometry, according to an embodiment of the present disclosure.
FIG. 8B is a bottom plan view of the vacuum cup illustrated in FIG. 8A.
FIG. 8C is a sectional perspective view of the vacuum cup illustrated in FIG. 8A, taken along a central axis of the cup.

Referring now to FIGS. 7A-7C, a vacuum cup 702 having a distal end 710 that defines a triangular opening 720 is shown. The vacuum cup 702 of the present embodiment is similar to the vacuum cups 2, 502 described above. Accordingly, like references numbers as used above denote common features in the present embodiment. For the sake of brevity, the following description focuses on differences between the vacuum cup 702 of the present embodiment and the vacuum cups 2, 502 described above.

The vacuum cup 702 includes a housing body 726 that defines three (3) sidewalls 730 arranged in a triangular pattern, as viewed in a reference plane orthogonal to a central axis X of the vacuum cup 702. Accordingly, the housing body 726 defines a vacuum chamber 706 that also has a triangular shape in the orthogonal reference plane. The sidewalls 730 intersect one another at three (3) corners 735 of the housing body 726, which corners 735 are preferably radiused. The triangular pattern can be equilateral, as shown, although other triangular patterns are within the scope of the present embodiment, including right, isosceles, and scalene.

Interior surfaces 722 of the sidewalls 730 can define a main portion 722*b* extending from a distal lead-in portion 722*a* toward a proximal end 724 of the chamber 706. The main portion 722*b* can planar, thereby defining a linear surface profile, and can define a length L4 in a range of about 1 mm to about 20 mm, as measured along the linear surface profile. It should be appreciated that the main portion 722*b* can alternatively be non-planar and can have non-linear profiles. The main portion 722*b* preferably tapers inwardly toward the central axis X toward the proximal end 724 of the chamber 706. The main portion 722*b* can define a taper angle A4, measured with respect to an axis parallel with the central axis X, in a range of about 10 degrees to about 80 degrees, more particularly in a range of about 0.25 degrees to about 10 degrees, and more particularly in a range of about 0.5 degrees to about 5 degrees.

The vacuum cup 702 includes a plurality of electrodes 708 arranged in an electrode array 709, which can include three (3) subsets 709*a-c* of electrodes 708. A first subset 709*a* of electrodes 708 can be disposed on an interior surface 722 of a first sidewall 730, a second subset 709*b* of electrodes 708 can be disposed on an interior surface 722 of a second sidewall 730, and a third subset 709*c* of electrodes 708 can be disposed on an interior surface 722 of a third sidewall 730. The subsets 709*a-c* of electrodes 708 can be carried by respective substrates or "pads" 752, which can be constructed of an electrically insulative material, such as silicon, polyetheretherketone (PEEK), polyphthalamide (PPA), polyethylene: polycarbonate; and polytherimide (PEI), by way of non-limiting examples. The substrates 752 can be flexible or rigid. The substrates 752 can also carry circuitry, such as wired circuitry or printed circuitry, for example, for providing electrical communication between the electrodes 708 and the controller 114. Accordingly, the substrates 752 can be circuit boards, such as printed circuit boards (PCBs). As described above, the circuitry can be configured so that the controller 114 can control parameters of the electroporation pulse(s) to each subset 709*a-d* of electrodes 708 individually and also to control the pulse parameters of each electrode 708 in each subset 709*a-c* individually. An exterior surface 753 of the substrate 752 can be attached to the interior surface 722 of the respective sidewall 730 via an adhesive, although other fastening techniques are within the scope of the present disclosure.

Each subset 709*a-c* of electrodes 708 can include a single electrode 708 or preferably multiple electrodes 708. In the illustrated embodiment, each subset 709*a-c* has four (4) electrodes 708. It should be appreciated that each subset 709*a-c* can have fewer or more than four (4) electrodes 708, such as a single (1), electrode, two (2), three (3), five (5), six (6), seven (7), eight (8), nine (9), ten (10), eleven (11), twelve (12), or more than twelve electrodes 708, such as one hundred (100) electrodes 708 or more. Due to advances in microelectromechanical systems (MEMS) technologies and nano-technologies, the size of each discrete electrode 708 can be reduced to such an extent that each subset 709*a-c* can have virtually a limitless quantity of discrete electrodes 708.

The electrodes 708 define contact surfaces 708*z*, which can be smooth, as shown. Major portions of the contact surfaces 708*z* can be planar, such as the respective portions overlying the main portion 722*b* of the interior surface 722. It should be appreciated, however, that the contact surface 708*z* of at least one and up to all of the electrodes 708 can be textured and/or define protrusions, similar to the manner described above. Moreover, the substrates 752 and electrodes 708 can be flexible and can overly channels and relief ports defined in the housing body 726 for allowing the electrodes 708 to flex inwardly when vacuum pressure is applied to the chamber 706, similar to the manner described above with reference to FIGS. 5A-5D.

Figures 7D, 7E:
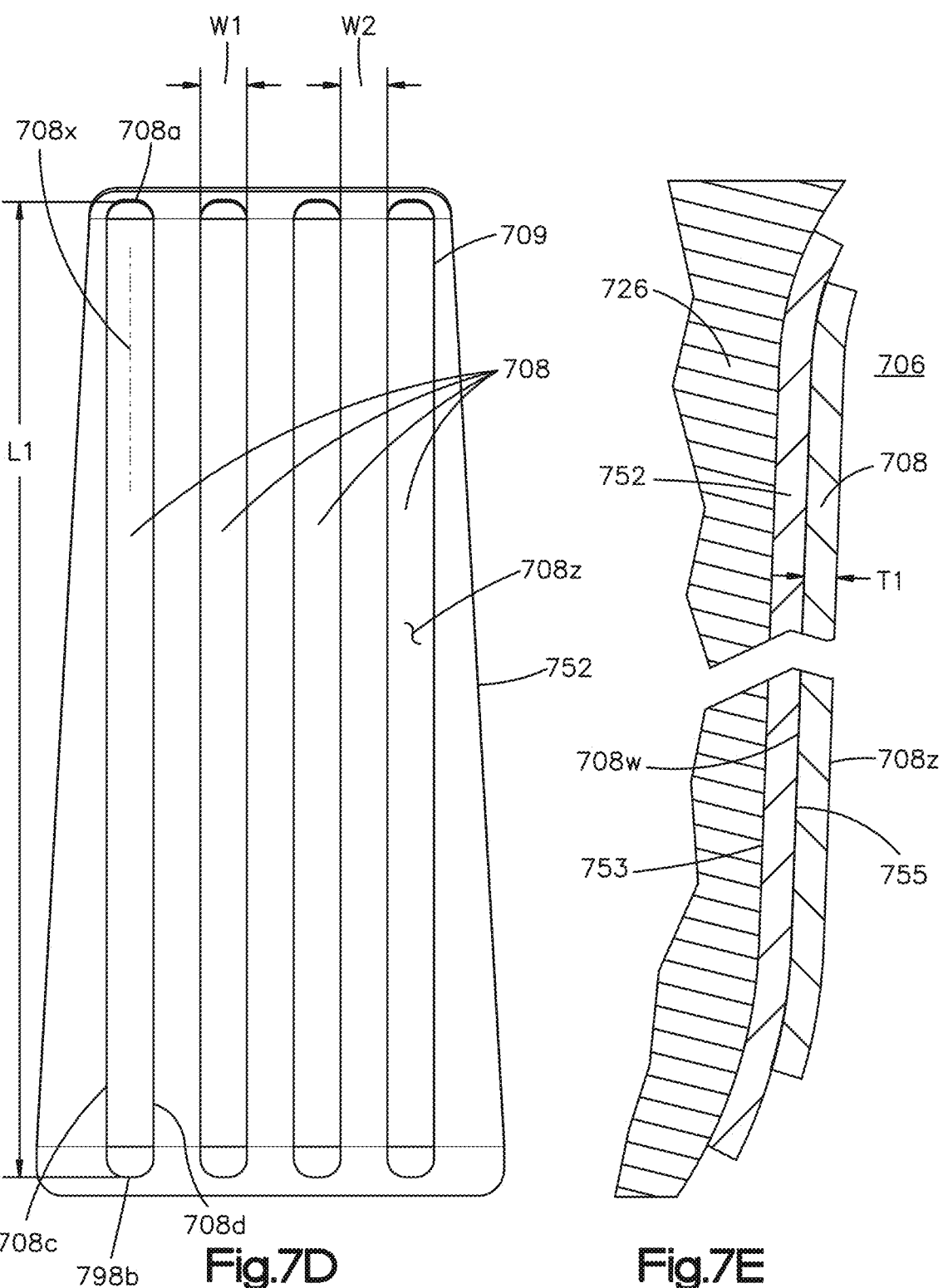
FIG. 7D is an elevation plan view of an electrode array positioned within the vacuum cup illustrated in FIG. 7A.
FIG. 7E is a side view of the electrode array illustrated in FIG. 7D.

Referring now to FIG. 7D, the electrodes 708 in each subset 709*a-c* can be parallel with each other. The electrodes 708 can define an electrode length L1, as measured between first and second ends 708*a,b* of the electrode 708 along a central axis 708*x* thereof. The electrode length L1 can be in the ranges described above. The electrodes 708 can also define an electrode width W1, as measured between first and second sides 708*c,d* of the electrode 708. The electrode width W1 can be in a ranges for C1 described above. The electrodes 708 of each subset 709*a-c* can also define an inter-electrode spacing gap W2, which can be in a range of about 1.0 mm to about 30 mm.

Referring now to FIG. 7E, the electrodes 708 can extend inwardly (into the vacuum chamber 706) from the substrate 752. The electrodes 708 can define an electrode thickness T1, measured from an interior surface 755 of the substrate 752 to the contact surface 708*z*. The electrode thickness T1 can be in a range of about 0.001 mm to about 2.000 mm. As shown, an exterior surface 708*w* of the electrode 708 can be affixed to the interior surface 755 of the substrate 752. In other embodiments, the exterior surface 708*w* of the electrode 708 can be partially embedded in the substrate 752. That is to say, the exterior surface 708*w* of the electrode 708 can reside at a depth between the exterior and interior surfaces 753, 755 of the substrate 752. In further embodiments, the exterior surface 708*w* of the electrode 708 can be entirely embedded in the substrate 752. That is to say, the exterior surface 708*w* of the electrode 708 can be coextensive with the exterior surface 753 of the substrate 752.

The electrode arrays 709*a-c* of the present embodiment are configured such that, when vacuum pressure draws tissue 102 into the vacuum chamber, the tissue 102 is pulled into contact with the contact surfaces 708*z* and also into the inter-electrode gaps W2, thereby also contacting the sides 708*c,d* of the electrodes, thereby increasing the overall contact interface area between the tissue 102 and the electrodes 708.

The geometry of the vacuum chamber 706 and the configuration of the electrode arrays 709*a-c* of the present embodiment allow substantially planar electrodes 708 along the sidewalls 730 of the vacuum cup 702, which provides a more columnar electroporation field (i.e., more elongated along the central axis X) in the tissue 102 relative to that of the vacuum cups 2, 502 described above. The triangular shape of the present embodiment can also beneficially constrain the tissue within the boundaries of an electroporation field defined by a triangular pulse pattern to a greater extent than prior art electroporation devices. Additionally, a polygonal array geometry, including the triangular array of the present embodiment, can create a more heterogeneous electroporation field due to the acute or "sharp" angles between adjacent electrodes on opposite sides of the corners 735 compared to other array designs, including circular designs. It can be desirable, for example, to create regions of increased electrical field magnitude (resulting in an increased electrical current) within the target tissue, and having "sharp" or acutely angled adjacent electrode edges is one way to create such increased electrical field/current regions in the tissue.

Referring now to FIGS. 8A-8C, a vacuum cup 802 having a distal end 810 that defines a rectangular opening 820 is shown. The vacuum cup 802 of the present embodiment is similar to the vacuum cups 2, 502, 702 described above. Accordingly, like references numbers as used above denote common features in the present embodiment. For the sake of brevity, the following description focuses on differences between the vacuum cup 802 of the present embodiment and the vacuum cups 2, 502, 708 described above, particularly differences from the vacuum cup 702 described above with reference to FIGS. 7A-7E.

The vacuum cup 802 includes a housing body 826 that defines four (4) walls, particularly a pair of opposed sidewalls 830 extending between a pair of opposed end walls 831, arranged in a rectangular pattern, thereby providing a vacuum chamber 806 that also has a rectangular shape in the orthogonal reference plane. In the illustrated embodiment, the sidewalls 830 are longer than the endwalls 831, although in other embodiments the sidewalls 830 and endwalls 831 can be the same length, such that the rectangle is a square. It should also be appreciated that the walls of the housing body 826 can define other quadrilateral geometries (i.e., non-rectangular).

Interior surfaces 822 of the walls 830, 321 can define a main portion 822*b* extending from a distal lead-in portion 822*a* toward a proximal end 824 of the chamber 806. The main portion 822*bs* of the sidewalls 830 and/or the endwalls 831 can taper inwardly and proximally at a taper angle A4, which can be in the ranges described above. The vacuum cup 802 includes a plurality of electrodes 808 arranged in an electrode array 809, which can include two (2) opposed subsets 809*a,b* of electrodes 808 disposed on the interior surfaces 822 of the sidewalls 830. The endwalls 831 can be devoid of electrodes 808, as shown, although in other embodiments, one or both of the endwalls 831 can have an additional subset of electrodes 808. In yet other embodiments, the endwalls 831 can have electrodes and the sidewalls 839 can be devoid of electrodes. In yet additional embodiments, one or more and up to each of the walls 830, 831 can have a single electrode, which can be configured according to various sizes and shapes.

As above, the subsets 809*a,b* of electrodes 808 can be carried by respective non-conductive substrates 852 attached to the interior surfaces 822. Each subset 809*a,b* can have four (4) electrodes 808, although each subset 809*a,b* can have more or fewer than four (4) electrodes 808. As described above, the electrode array 809 can include circuitry configured so that the controller 114 can control parameters of the electroporation pulse(s) to each subset 809*a,b* of electrodes 808 individually and also to control the pulse parameters of each electrode 808 within each subset 809*a, b* individually.

As shown, contact surfaces 808*z* of the electrodes 808 can be smooth, and major portions thereof can be planar. However, in other embodiments, the contact surfaces 808*z* can be textured and/or define protrusions, as described above. The housing body 826, substrates 852, and electrodes 808 can also be cooperatively configured to allow the electrodes 808 to flex inwardly responsive to vacuum pressure, similar to the manner described above with reference to FIGS. 5A-5D. The electrodes 808 can have lengths L1, widths W1, and thicknesses T1 similar to those described above with reference to FIGS. 7D-7E, and can operate similarly as described above.

The rectangular geometry of the vacuum chamber 806 and the configuration of the electrode arrays 809*a,b* of the present embodiment provide a spheroidal electroporation field that is more elongated along a direction transverse to the central axis X (particularly along a direction orthogonal to the endwalls 831) relative to that of the vacuum cups 2, 502, 702 described above. Furthermore, the rectangular array of the present embodiment allows substantially planar electrodes directly opposite each other and capable of firing directly opposing electrical pulses. In this regard, the array of the present embodiment can be employed in a manner similar to opposed-plate or caliper-type electroporation devices known in the art. For example, the rectangular array design of the present embodiment can allow the physician to "pinch" an elongated section of tissue similar to the caliper-type electrode configurations. It can be advantageous to "grab" tissue primarily along one axis and pinch it to create an elongated treatment zone in the tissue. For example, with increasing aspect ratio, the rectangular cup 802 can treat a larger overall tissue area without increasing the gap between electrodes. This can allow, for example, the use of lower voltages and treating a larger tissue area than a circular array design operating at the same voltage.

Additionally, similarly as described above, a polygonal array geometry, including the array of the present embodiment, can create a more heterogeneous electroporation field due to the sharp angles between adjacent electrodes (in this embodiment, nearly parallel) on opposite sidewalls 830 of the cup 802. Moreover, as described above, the array can be employed to create regions of increased electrical field magnitude within the tissue, as described above.

It should be appreciated that vacuum cups of other embodiments can have openings and/or chamber geometries of other polygonal shapes, such as pentagonal, hexagonal, heptagonal, octagonal, and so forth up to circular geometries. Furthermore, such polygonal shapes need not have equilateral configurations. In yet other embodiments, the vacuum cups can have openings and/or chamber geometries of other shapes, such as elliptical, oblong, or irregular shapes, by way of non-limiting examples. It should be appreciated that elliptical cup shapes can provide advantages similar to the rectangular cup 802 described above, including the ability to "grab" tissue primarily along one axis and pinch it to create an elongated treatment zone in the tissue, thereby allowing lower voltages for treating a larger tissue area.

Referring now to FIGS. 30A-33F, simulated test results of various four-electrode arrays 9 on adipose tissue 103 and skin 104 will now be described. In each of FIGS. 30A-33F, opposed electrodes 8 are spaced from each other at a distance of 15 mm (which distance is analogous to chamber diameter D1), and the applied voltage across the electrodes is the same. Thus. FIGS. 30A-33F demonstrate the effects of electrode shape, size, and spacing on electric field creation.

FIGS. 30A-31F show circular arrays 9 in which the contact surfaces of the electrodes extend along a generally circular perimeter. The widths of the electrodes shown in FIGS. 30A-31F are defined by a fraction of the chamber diameter: thus, a chamber that tapers inwardly towards the top will have thinner electrode widths near the top and thicker electrode widths near the bottom, while always occupying the same percentage of the circumference of the chamber at any location along the interior surface of the chamber. The electrodes in FIGS. 30B and 31B each have an angular span A2 of 15 degrees; the electrodes in FIGS. 30C and 31C each have an angular span A2 of 30 degrees; the electrodes in FIGS. 30D and 31D each have an angular span A2 of 45 degrees; the electrodes in FIGS. 30E and 31E each have an angular span A2 of 60 degrees; and the electrodes in FIGS. 30F and 31F each have an angular span A2 of 75 degrees.

FIGS. 32A-33F shown rectangular (specifically, square) arrays 9 in which the contact surfaces of the electrodes define sides of a rectangle. The electrodes in FIGS. 32B and 33B each have a width of 2.5 mm; the electrodes in FIGS. 32C and 33C each have a width of 5.0 mm; the electrodes in FIGS. 32D and 33D each have a width of 7.5 mm; the electrodes in FIGS. 32E and 33E each have a width of 10.0 mm; and the electrodes in FIGS. 32F and 33F each have a width of 12.5 mm. The widths of the electrodes shown in FIGS. 32A-33F are constant from top to bottom. Thus, a chamber that tapers inwardly towards the top will cause adjacent electrodes constructed in this manner to be closer to one another at the top than at the bottom. Depending on the cup dimensions and taper angle of the wall, this could cause adjacent electrodes to come very close to each other or even touch each other at the top of the chamber, which is not preferred.

From these Figures, it can be seen that the square arrays (FIGS. 32A-33F) create more heterogeneous electric fields in both adipose tissue 103 and skin 104 than their circular array counterparts (FIGS. 30A-31F). Thus, it can also be said that the circular arrays create more homogeneous electric fields in both adipose tissue 103 and skin 104 than their rectangular array counterparts. These differences in field heterogeneity/homogeneity produced by the circular and rectangular arrays can be employed beneficially as needed depending on the desired treatment. For example, when a particular electroporation treatment benefits from a more homogeneous electric field, the physician can select a circular vacuum cup (and electrode array). When a particular electroporation treatment benefits from a more heterogeneous electric field, the physician can select a polygonal vacuum cup (and electrode array). It should be appreciated that, with respect to electrode design, it is preferable to maintain adequate spacing between adjacent electrodes, particularly when the vacuum chamber tapers inwardly at the top, as demonstrated by the designs shown in FIGS. 30A-31F.

Figure 9A:
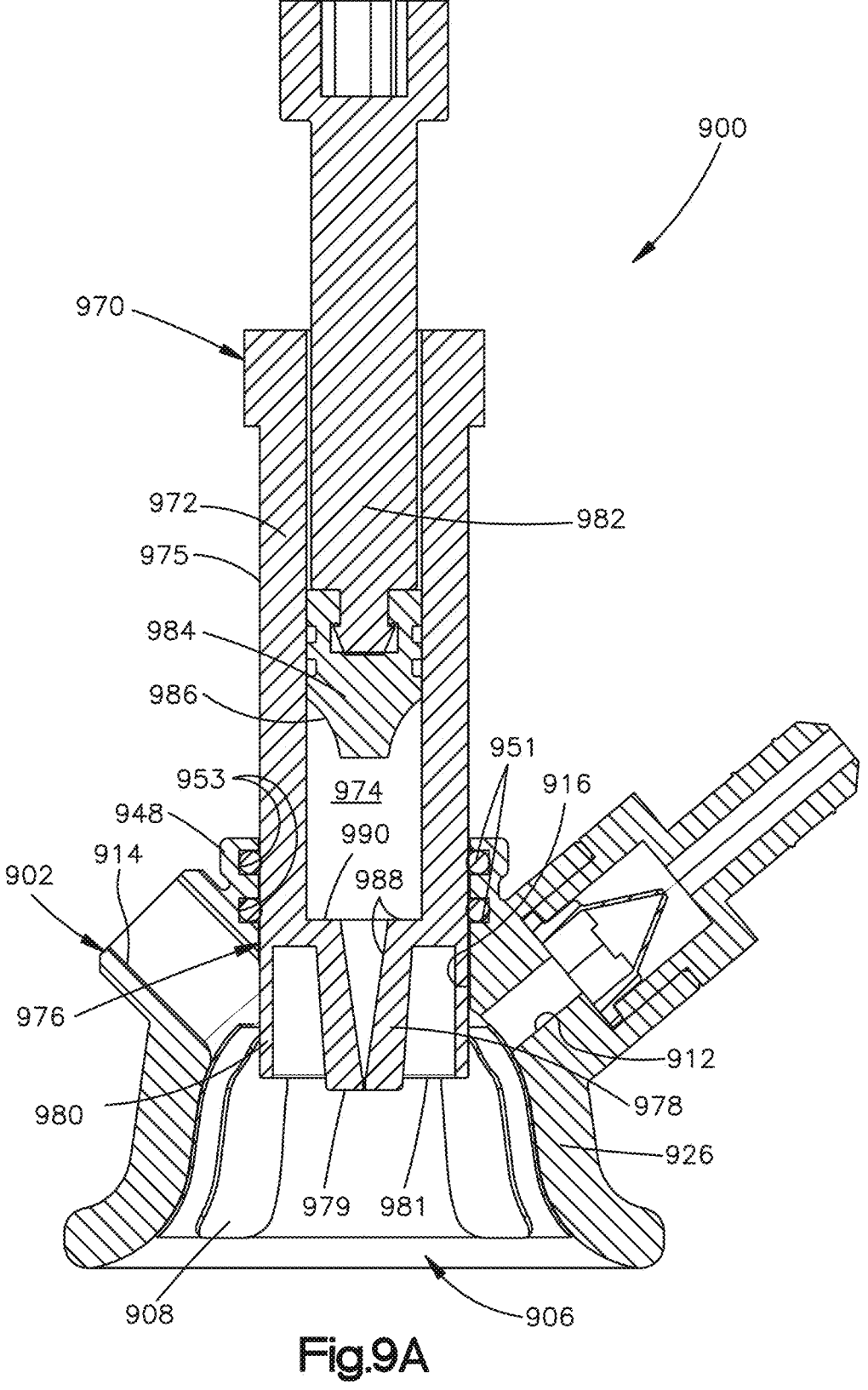
FIG. 9A is a sectional side view of an electroporation assembly that includes a vacuum cup having a receptacle in which a needle-free injection device is received, according to an embodiment of the present disclosure.

Referring now to FIG. 9A, an example vacuum-electroporation assembly 900 is shown that includes a vacuum cup 902 configured for needle-free injection of an agent, particularly via jet injection. Accordingly, the vacuum cup 902 can be referred to as a "needle-free" vacuum cup 902 or a "jet-injection" vacuum cup 902. The vacuum cup 902 of the present embodiment is similar to the vacuum cups 2, 502, 702, 802 described above, particularly the vacuum cup 2 described above with reference to FIGS. 1-4F. Accordingly, like references numbers as used above denote common features in the present embodiment. For the sake of brevity, the following description focuses on differences between the vacuum cup 902 of the present embodiment and the vacuum cup 2 described above with reference to FIGS. 1-4F.

As above, the vacuum cup 902 has a housing body 926 that defines vacuum chamber 906 having electrodes 908 disposed therein and a first port 912, a second port 914, and a third port 916 each in communication with the vacuum chamber 906. As above, the first port 912 is configured for connection to the vacuum source 106, the second port 914 is configured for passage of circuitry, among other things, into the vacuum chamber 906. However, the third port 916 of the present embodiment is configured to receive a jet injection device 970 for injecting a small stream or "jet" of an injectate 142 into tissue 902 drawn into the vacuum chamber 906. Additionally, the housing body 926 defines a mounting formation 948 at an external end of the third port 916 configured to provide a sealed coupling with the injection device 970. The mounting formation 948 can carry one or more sealing members, such as sealing O-rings 951, which can reside in receptacles 953 defined in the mounting formation 948 and are configured to provide sealing engagement with an exterior of the injection device 970.

The jet injection 970 device includes an injection housing 972 that defines a fluid chamber or reservoir 974 in which the injectate 142, which includes an agent, is stored. An outer surface 975 of the injection housing 972 is cooperatively sized with the third port 916, and with the sealing O-rings 951, to provide a sealing connection between the injection housing 972 and the vacuum chamber 906. A distal portion 976 of the injection housing 972 defines a nozzle 978 in fluid communication with the reservoir 974. The nozzle 978 is configured to expel the injectate 142 from the reservoir 974 into the vacuum chamber 906. The distal portion 976 can also include a shield 980 at least partially surrounding the nozzle 978. The shield 980 can act as a physical barrier that contains any potential backsplash or rebound of the injectate 142 generated during jet injection. The shield 980 can also protect circuitry of the cup 902 from exposure to the injectate 142.

A distal end 979 of the nozzle 978 preferably extends distally beyond a distal end 981 of the shield 980. The jet injection device 970 includes a plunger 982 carrying a piston 984 at a distal end thereof. A distal tip 986 of the piston 984 and an interior surface 988 of the reservoir 974 at a distal end 990 thereof have complimentary geometries such that advancement of the piston 984 to the distal end 990 expels the jet of injectate 142 from the nozzle 978 and into the tissue 102. It should be appreciated that the reservoir 974 can be configured to carry a pre-measured volume or dose of the injectate. Furthermore, the plunger 982 can be controlled, such as by a firing mechanism or actuator, to expel a pre-determined dose of the injectate through the nozzle 978 and into the patient's tissue 102. Such a firing mechanism can include, by way of non-limiting examples, a pre-loaded or loadable spring or springs, a compressed gas canister, and the like.

The jet injection device 970 can constructed as disclosed more fully in any of U.S. Pat. No. 10,045,911, issued Aug. 14, 2018, entitled "Intradermal Injection Device" ("the '911 Reference"); U.S. Patent Publication No. 2019/0000489 A1, published Jan. 3, 2019, entitled "Intradermal Jet Injection Electroporation Device"; and US Patent Publication No. 2009/0137949 A1, published May 28, 2009, entitled "Needle-Free Injection Device with Nozzle Auto-Disable" ("the '949 Reference"), the entire disclosure of each of which is hereby incorporated by reference herein.

Figure 9B:
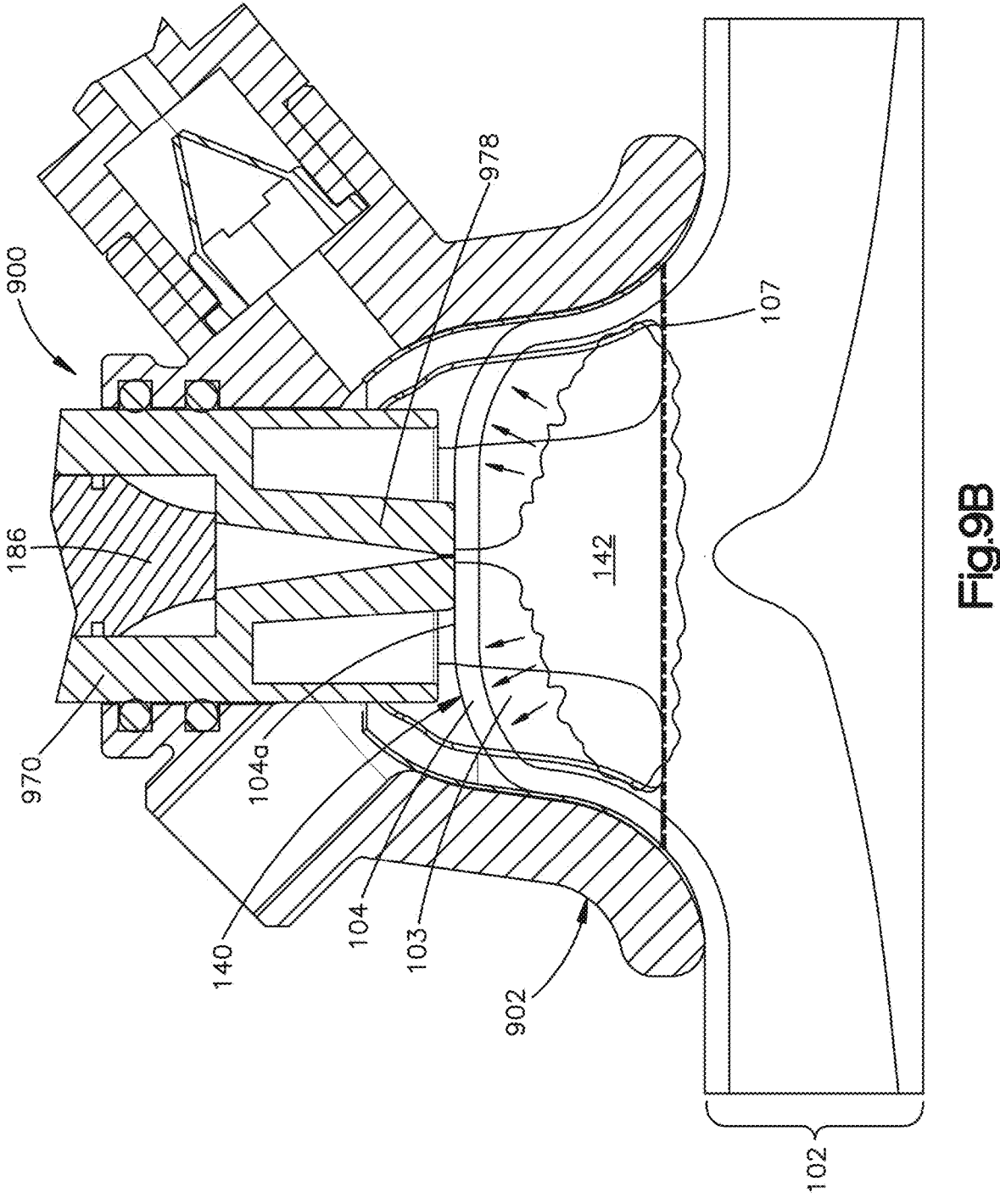
FIG. 9B is an enlarged sectional side view showing a representative stage of employing the electroporation assembly illustrated in FIG. 9A to inject an agent into tissue drawn into the vacuum chamber.

The needle-free vacuum cup 902 and the jet injection device 970 possess complimentary features that enhance the electroporation treatment provided thereby. For example, with reference to FIG. 9B, as vacuum pressure draws a mound 140 of tissue 102 into the vacuum chamber 6, the skin layer 104 on the mound 140 tightens, temporarily reducing elasticity of the skin layer 104, which allows the jet or stream of injectate exiting the nozzle 978 to puncture the skin layer 104 more efficiently with less injectate rebound. To assist in tightening the skin layer 104, the physician can employ sufficient vacuum pressure to draw the skin layer 104 into contact with the distal end 979 of the nozzle 978 such that the skin layer 104 deforms around the distal end 979 of the nozzle 978, thereby forming a depression 104a in the skin layer 104 at the contact interface with the distal end 979 and further stretching the skin layer 104 at the depression 104a. Such tightness at the skin layer 104 in combination with use of the jet injection device 970 allows the expelled injectate 142 to puncture the skin layer 104 and penetrate throughout the tissue mound 140 upon injection to a greater extent than with a needle injection (compare with FIG. 4C), and to a greater extent than with a jet injection device that is not assisted by vacuum pressure.

Injectate penetration throughout the tissue mound 140) can be characterized as the pressurized injectate forming thousands of microscopic cuts or paths within the tissue 102 as the injectate is forced throughout the tissue 102, particularly the adipose tissue 103, effectively permeabilizing the tissue. Furthermore, by thereafter subjecting the tissue 102 to vacuum pressure (i.e., such as in a continuation of the vacuum pulse that drew the tissue mound 140) into the chamber 906 and optionally one or more subsequent vacuum pulses), the injectate 142 already more extensively dispersed can be further dispersed throughout the tissue mound 140) responsive to the vacuum pressure according to the fluid dispersion mechanisms described above.

Referring now to FIGS. 10A-10D, another embodiment of a needle-free vacuum cup 1002 will be described, in which the vacuum cup 1002 has a vacuum chamber 1006 configured such that tissue 102 drawn therein is pulled at least partially into a plurality of apertures 1063 defined in electrodes 1008 within the vacuum chamber 1006. The vacuum cup 1002 of the present embodiment is similar to the vacuum cups described above, particularly the vacuum cup 902 described above with reference to FIGS. 9A-9B. Accordingly, like references numbers as used above denote common features in the present embodiment. For the sake of brevity, the following description focuses on differences between the vacuum cup 1002 of the present embodiment and the vacuum cup 902 described above.

Figures 10A, 10B, 10C:
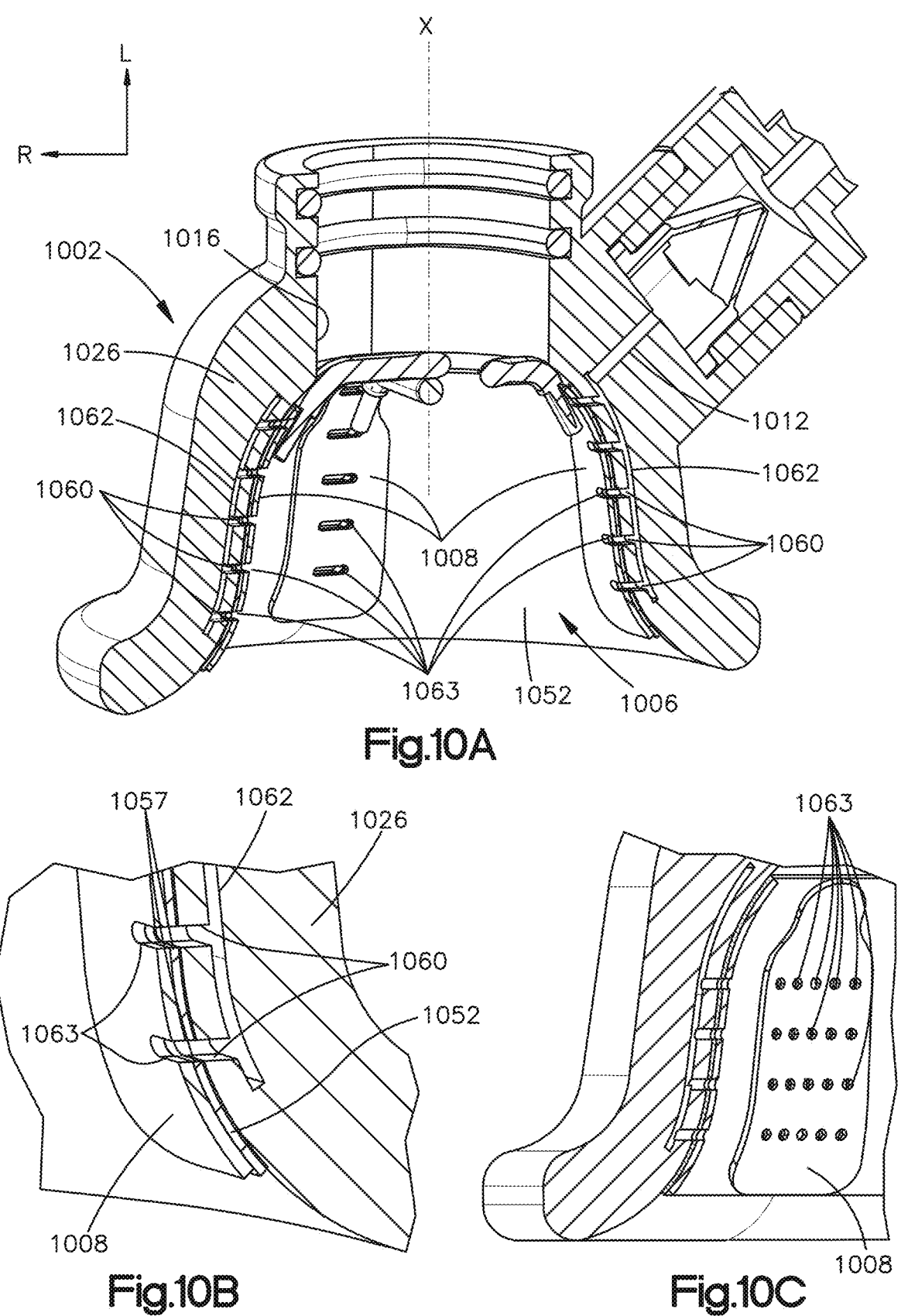
FIG. 10A is a sectional perspective view of another embodiment of a vacuum cup having a receptacle in which a needle-free injection device is received, wherein the vacuum cup has a cup housing that defines a manifold including a plurality of ports in fluid communication with the vacuum chamber through a corresponding plurality of apertures defined in the electrodes.
FIG. 10B is an enlarged perspective, partial sectional view of the corresponding ports and apertures shown illustrated in FIG. 10A.
FIG. 10C is a perspective, partial sectional view of an alternative arrangement of corresponding ports and apertures, according to another embodiment of the present disclosure.

Referring now to FIGS. 10A-10B, the vacuum cup 1002 of the present embodiment has a housing body 1026 that, as above, defines a first port 1012 for connection to the vacuum source 106, a second port (not shown) for providing circuitry with access to the vacuum chamber 1006, and a third port 1016 for providing sealed connection with the jet injection device 970. In the present embodiment, instead of the third port 1016 extending directly to the vacuum chamber 1006, the third port 1016 extends inwardly to an annular channel 1062 defined by the housing body 1026. The annular channel 1062 at least partially surrounds the vacuum chamber 1006 and is outwardly spaced therefrom along the radial direction R. The housing body 1026 further defines a plurality of housing ports 1060 that extend inwardly from the annular channel 1062 toward the vacuum chamber 1006. Accordingly, the housing body 1026 can define a manifold that defines the plurality of housing ports 1060. As above, the electrodes 1008 can be carried by a sleeve 1052 that is affixed to an interior surface 1022 of the housing body 1026. The sleeve 1052 defines sleeve ports 1057 that provide fluid communication between the housing ports 1060 and the apertures 1063. Thus, the sleeve ports 1057 also provide fluid communication between the annular channel 1062 and the vacuum chamber 1006. The vacuum pressure is supplied to the vacuum chamber 1006, in turn, through the third port 1016, the annular channel 1062, the housing ports 1060, the sleeve ports 1057, and the electrode apertures 1063. In embodiments where the electrodes 1008 are coupled directly to the interior surface 1022 of the housing body 1026, the electrode apertures 1063 can be directly contiguous with the housing ports 1060. The annular channel 1062 can extend annularly along an entire revolution about the central axis, although in other embodiments the channel 1062 can extend less than a full revolution about the central axis X.

As shown in FIG. 10A, each electrode 1008 can define a single column of apertures 1063, which can be elongated along the circumferential direction C. Each column can include five (5) apertures 1063, as shown, which can be characterized as a "5×1" (i.e., 5 rows by 1 column) array of apertures 1063 or "aperture array". Other aperture arrays are within the scope of the present disclosure. For example, as shown in FIG. 10C, the apertures 1063 of each electrode 1008 can be arranged in an aperture array having multiple rows and multiple columns of apertures 1063, which are aligned with corresponding rows and columns of sleeve ports 1057 and corresponding rows and columns of housing ports 1060. The aperture array can be a 4×5 array, although other aperture array configurations are within the scope of the present disclosure.

Figure 10D:
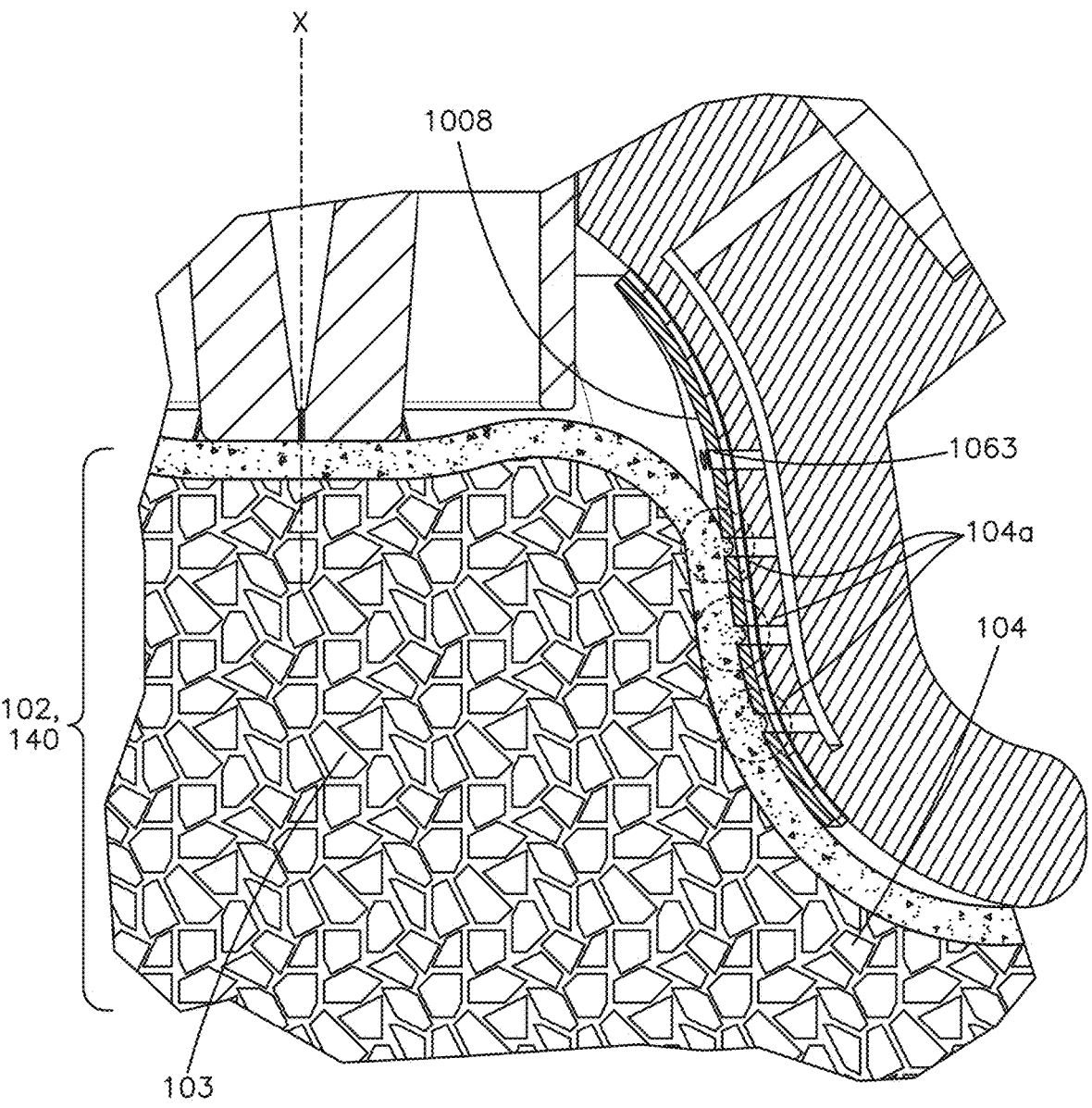
FIG. 10D is an enlarged sectional side view of a portion of the vacuum cup illustrated in FIG. 10A during use to provide an electroporation treatment to adipose tissue.

As shown in FIG. 10D, the apertures 1008 are configured such that the tissue 102 drawn into the vacuum chamber 1006 can at least partially extend within one or more of the apertures 1063, shown at highlighted areas 104a. This increases the adhesion force between the skin layer 104 and the electrodes 1008, and also increasing the contact surface area between the tissue 102 and the electrodes 1006. Moreover, by pulling the tissue 102, such as the skin layer 104, into the one or more apertures 1063 that communicate the vacuum pressure into the chamber 1006, the vacuum cup 1002 of the present embodiments can effectively pull and stretch the skin layer 104 of the mound 140, such as away from the central axis X, thereby allowing the jet-injected stream of injectate 142 to penetrate the tissue 102 more efficiently than in other embodiments. For example, by distributing the vacuum ports 1060 throughout the chamber 1006, vacuum pressure in the chamber 1006 is unlikely to pull the injectate out of the tissue at the injection site.

Furthermore, portions of the skin layer 104 extending into the apertures 1063 can disrupt and alter the top portion of the skin layer 104, thereby improving the electric field distribution within the tissue mound 140, similar to the manner described above with reference to the protrusions 664 of FIGS. 6A-6D.

With continued reference to FIGS. 10A-10D, it should be appreciated that the vacuum cup 1002 can be configured to sense the presence and/or absence of tissue within the individual apertures 1063, within the individual sleeve ports 1057, and/or within the individual housing ports 1060. For example, one or more and up to all of the individual apertures 1063 in each electrode 1008 can include an individual sensor that can sense the presence and/or absence of tissue within the associated aperture 1063. Such tissue sensors can include separate electrodes that can be configured to sense an electrical parameter that indicates the presence/absence of tissue, such as impedance, by way of non-limiting example. The separate, tissue-sensing electrodes of the foregoing example can be electrically isolated from the electroporation electrodes 1008 or alternatively on separate channels from the electroporation electrodes 1008. In other embodiments, the tissue sensors can be of another type, such as force-type sensors that can detect direct tissue contact or pressure sensors that can detect when the individual apertures 1063, sleeve ports 1057, and or housing ports 1060 are sealed, by way of non-limiting examples.

The tissue sensors can be connected to circuitry, such as wired circuitry or printed circuitry, in electrical communication with the controller 114. For example, such circuitry can be printed circuitry on the same printed circuit board (PCB) as the circuitry for controlling the electrodes 1008. The tissue sensors can be employed to map tissue adhesion throughout the chamber 1006. Such tissue adhesion mapping information can be employed for data collection purposes, and can additionally or alternatively be employed in an active pressure feedback mechanism for adjusting the level of vacuum pressure upward or downward based on the sensor readings in each aperture. In such tissue adhesion mapping embodiments, the tissue sensor circuitry preferably includes an individual circuit for each tissue sensor. As alternative to tissue adhesion mapping, the tissue sensors can collectively be on a shared circuit, and the controller 114 can calculate the change in collective sensor measurements (i.e., the overall "delta") compared to initial baseline measurements to provide an overall measure of how much tissue adherence to the chamber walls has occurred.

In additional embodiments of a jet-injection vacuum cup, such as the cups 902, 1002 described above, the distal end 979 of the nozzle 978 can be adapted to define an electrode of the array. By way of a non-limiting example of such an embodiment, the distal end 979 of the nozzle 978 can be coated with or fabricated from an electrically conductive material, such as a conductive paint, metal, or polymer, and can be in electrical communication with the controller 114. In this manner, the distal end 979 of the nozzle 978 can be employed to deliver electroporation pulses to and/or from the other electrodes on the interior surface of the vacuum chamber. In such embodiments, the other electrodes can be annular ring-type electrodes or semi-annular electrodes, such as those described above with reference to FIGS. 3I-3L, and/or those described below with reference to FIGS. 15A-15C. Such embodiments would allow for concentric electroporation pulse patters ("firing patterns"), including those discussed in more detail below. The inventors successfully used such a concentric electrode array in a vacuum cup to perform intradermal jet-injection of fluid into rabbits and guinea pigs and thereafter perform electroporation of intradermal tissue at the injection site.

As stated above, the inventors have discovered a number of beneficial results from the vacuum-assisted electroporation treatments using the vacuum cups described above. Such beneficial results including increased fluid dispersion of the injectate in subcutaneous tissue and skin tissue, and also increased infiltration of in vivo fluids at the treatment site.

Referring now to FIG. 11A, the effect of vacuum pressure on injection sites can be seen. In this example, equivalent volumes of methylene blue injectate were injected into porcine tissue at two sites using the same injection technique at the same subcutaneous depth. The injection site shown at left was not subjected to vacuum pressure. The injection site shown at right was subjected to vacuum pressure of approximately −10.6 psi for 15 seconds using the vacuum cup 2 described above with reference to FIGS. 2A-2F and having a base diameter D1 of about 15 mm, a chamber depth of L2 of about 15 mm, and an interior wall taper angle of about 4 degrees. Neither site was treated with electroporation. In this example, the vacuum pressure effectively redistributed fluid and subsequently held the injectate within a region underlying the cup. This would have provided a higher injectate concentration within the cup's treatment zone had electroporation been performed.

Referring now to FIGS. 11B-11C, a comparative study of vacuum pressure on fluid dispersion was performed on guinea pigs. The subjects were both administered an injection of methylene blue into adipose tissue. The injection in FIG. 11B was performed with a needle-free vacuum cup similar to that shown in FIG. 9A. In particular, the tissue was in the vacuum chamber responsive to vacuum pressure during the jet-injection. The injection in FIG. 11C was performed by a subcutaneous needle technique and vacuum pressure was not applied. Neither subject in this study was treated with electroporation. As demonstrated, the vacuum-assisted jet injection (FIG. 11B) caused significantly more injectate dispersion in the adipose layer than the subcutaneous needle injection without application of vacuum pressure (FIG. 11C).

Figures 34A, 34B:
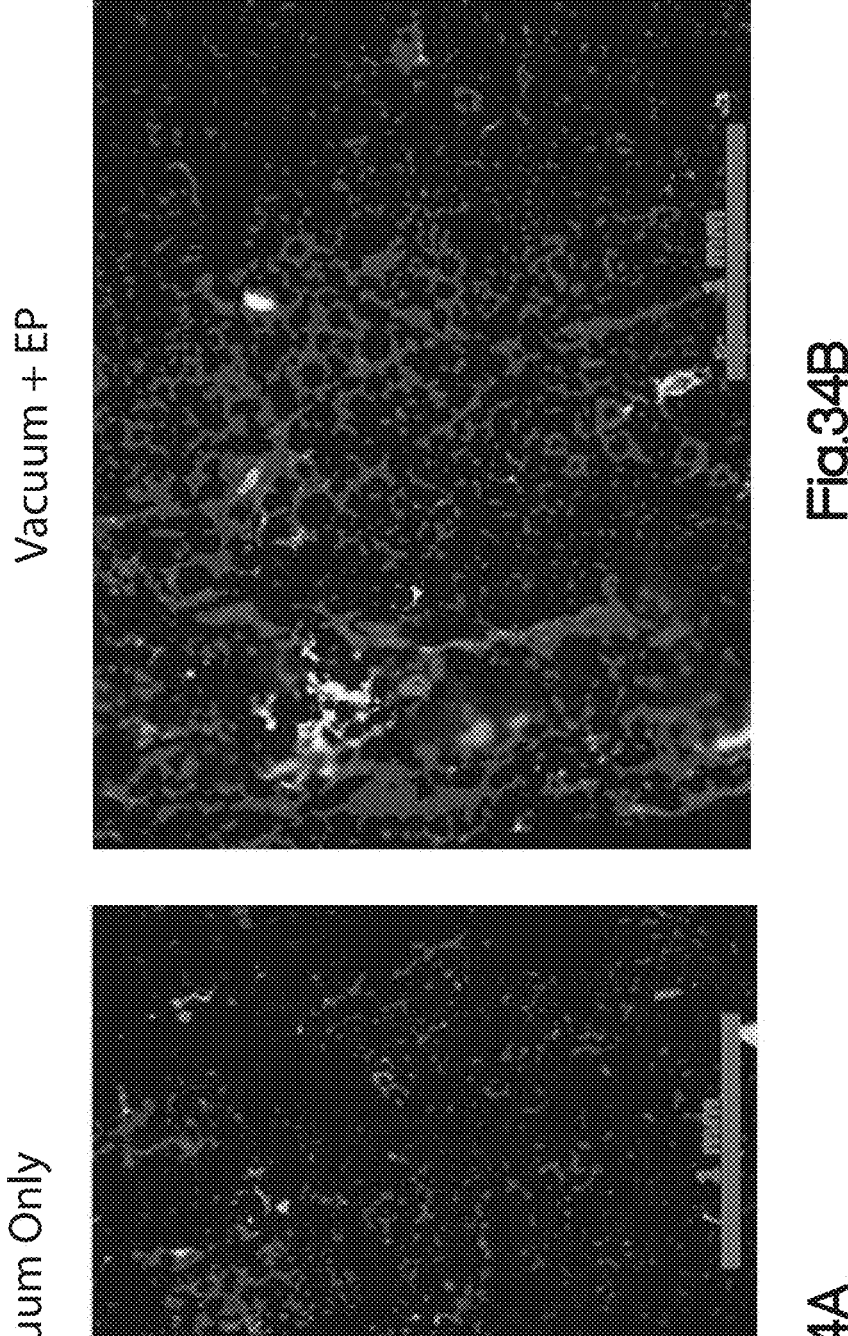
FIGS. 34A-34B show a side-by-side comparison of cellular infiltration (blue) in guinea pig adipose tissue following vacuum-assisted treatments; the treatment in FIG. 34A was a vacuum-only treatment (i.e., no electroporation) using a vacuum cup similar to that shown in FIG. 2A; the treatment in FIG. 35B was a vacuum-assisted electroporation treatment (i.e., vacuum pressure+electroporation) using the vacuum cup.

Referring now to FIGS. 34A-34B, a comparative study of the cumulative effect of electroporation and vacuum pressure on cellular infiltration in adipose tissue was performed on guinea pigs. A plasmid encoding the gene for green fluorescent protein (GFP) was injected into the adipose tissue via subcutaneous injection using a 29-gauge insulin syringe into the interscapular fat pad. The injection sites of both subjects were treated with the same vacuum pressure. The subject in FIG. 34B was further treated via electroporation at the injection site using a vacuum cup similar to that shown in FIG. 2A. The subject in FIG. 34A was not treated via electroporation. Histological sections were taken at the treatment site for comparison of GFP expression (visible as green fluorescence) and cellular infiltration (visible as blue fluorescence following 4',6-diamidino-2-phenylindole (DAPI) staining. As shown, GFP expression (green) is detectable following vacuum pressure in both subjects (i.e., regardless of whether the treatment site was electroporated). However, further application of electroporation in combination with the vacuum pressure (FIG. 34B) increased cellular infiltration (blue), in comparison to application of vacuum pressure only (FIG. 34A). These studies demonstrate that application of vacuum pressure in combination with electroporation can enhance immunogenicity.

Figure 12:
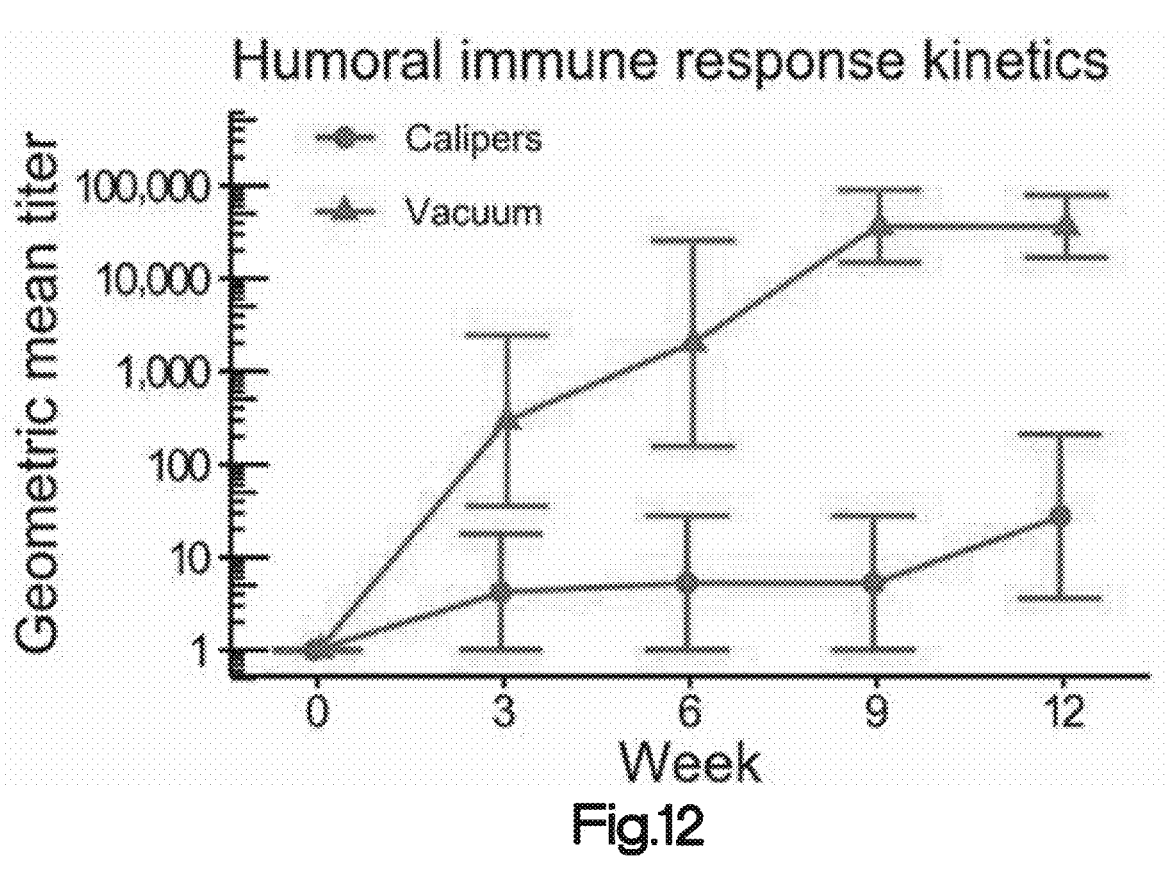
FIG. 12 is a graph showing 12-week humoral immunogenicity ELISA data in guinea pigs after electroporation treatments in adipose tissue with pGX 2013 (a DNA vaccine against influenza virus nucleoprotein (NP)), particularly showing comparative humoral immune responses following electroporation treatment with; the vacuum cup illustrated in FIG. 2A; and a caliper-electrode electroporation device.

Referring now to FIG. 12, test data shows that over a 12-week ELISA study comparing humoral immune responses in subject guinea pigs, subjects treated with the vacuum cup 2 shown in FIG. 2A (blue plot—"Vacuum") showed increased humoral immunogenicity over subjects treated with a caliper-type electroporation device (red plot—"Calipers") over the 12-week study. Subjects in both groups were injected with equivalent volumes of pGX 2013 (a DNA vaccine against influenza virus nucleoprotein (NP)) via needle injection in the adipose layer and treated with electroporation.

Figure 13:
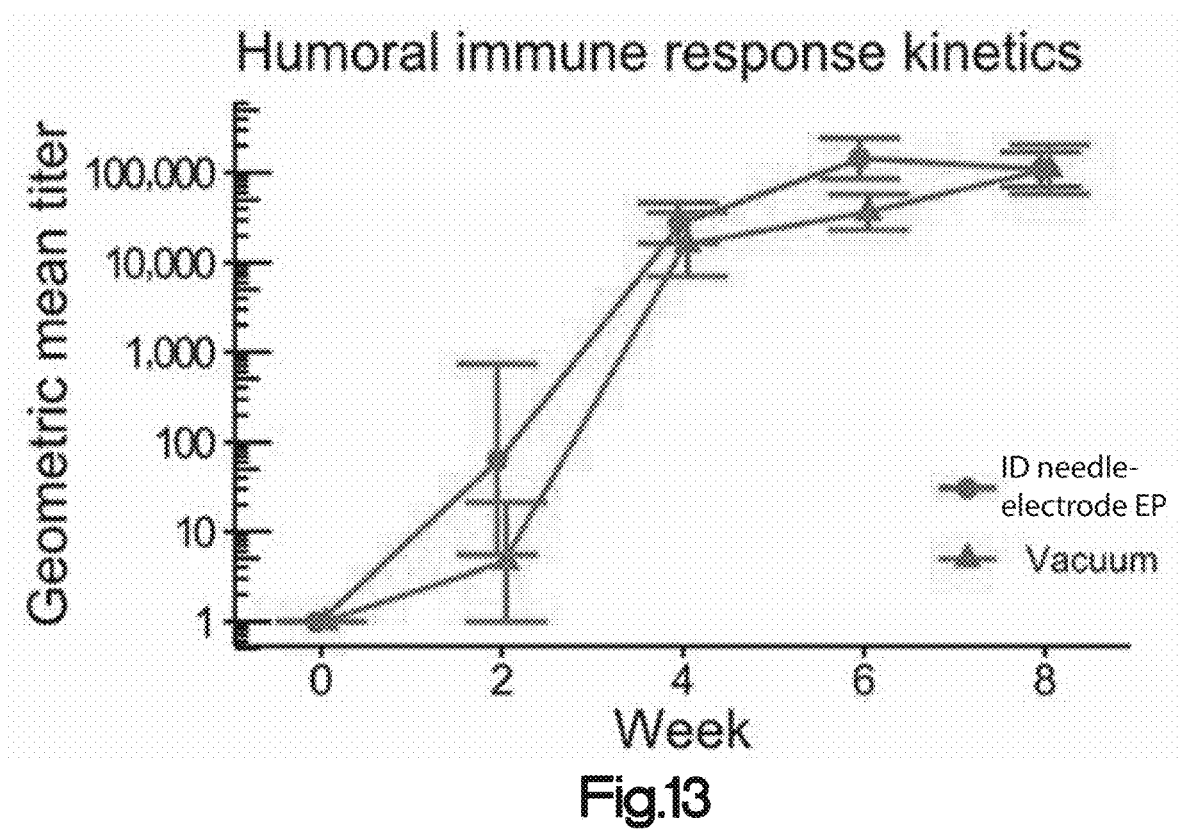
FIG. 13 is a graph showing 8-week humoral immunogenicity ELISA data in guinea pigs after treatments of pGX 2303 (a DNA vaccine against human respiratory syncytial virus fusion glycol-protein (RSV-F)), particularly showing comparative humoral immune responses following: electroporation treatment of adipose tissue with the vacuum cup illustrated in FIG. 2A; and electroporation treatment in skin with a prior art needle-array electroporation device.

Referring now to FIG. 13, over an 8-week ELISA study comparing humoral immune responses in subject guinea pigs, subjects treated with an injection of pGX 2303 (a DNA vaccine against human respiratory syncytial virus fusion glycol-protein (RSV-F)) in adipose tissue and electroporation using the vacuum cup 2 shown in FIG. 2A (blue plot—"Vacuum") showed comparable humoral immunogenicity to that of subjects treated with an intradermal injection of the vaccine and electroporation using an intradermal needle-electrode electroporation device (red plot—"ID needle-electrode EP"). Injections were of equivalent dose (20 ug). The intradermal injections were 100 μL and the adipose injections were 300 μL. The vacuum cup 2 had a 15 mm chamber diameter D1 with 4 electrodes.

Figure 14A:
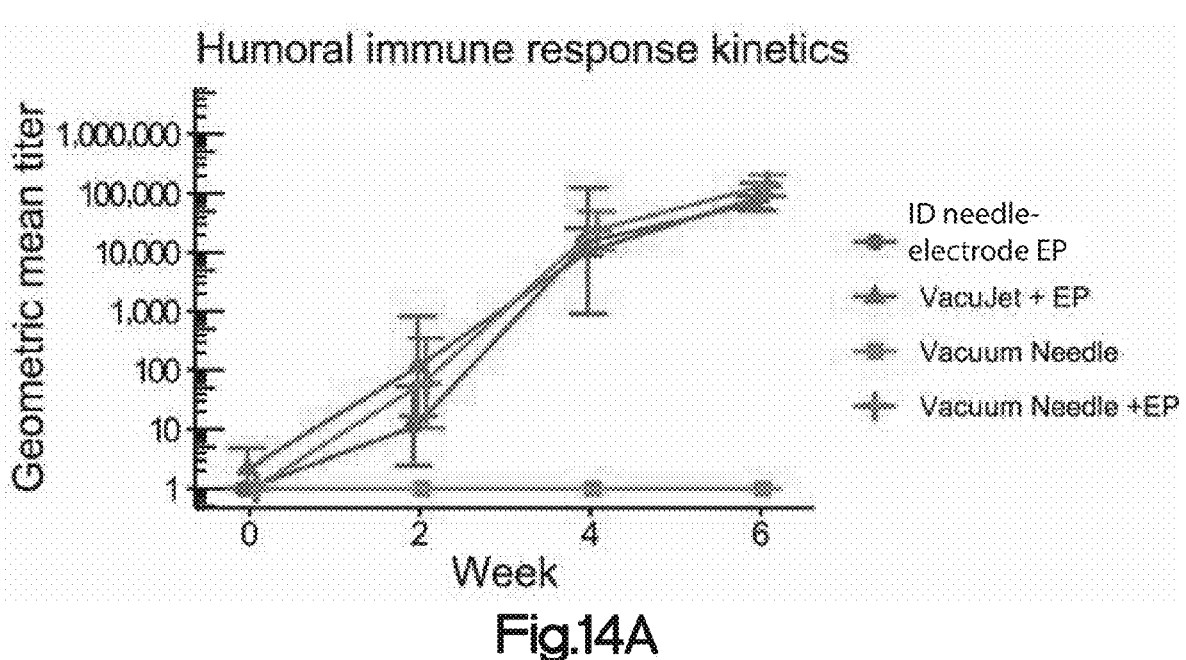
FIG. 14A is a graph showing 6-week humoral immunogenicity ELISA data in guinea pigs after treatments of pGX 2013 (a DNA vaccine against the influenza virus nucleoprotein (NP)), particularly showing comparative humoral immune responses following treatments involving: (1) electroporation of intradermal tissue using a prior art needle-array electroporation device: (2) electroporation of adipose tissue with the needle-free vacuum cup illustrated in FIG. 9A, with application of post-electroporation vacuum pressure: (3) injection into adipose tissue with the needle-injection vacuum cup illustrated in FIG. 2A, with application of post-injection vacuum pressure but without electroporation: (4) and electroporation of adipose tissue with the needle-injection vacuum cup illustrated in FIG. 2A, with application of post-electroporation vacuum pressure.
Figure 14B:
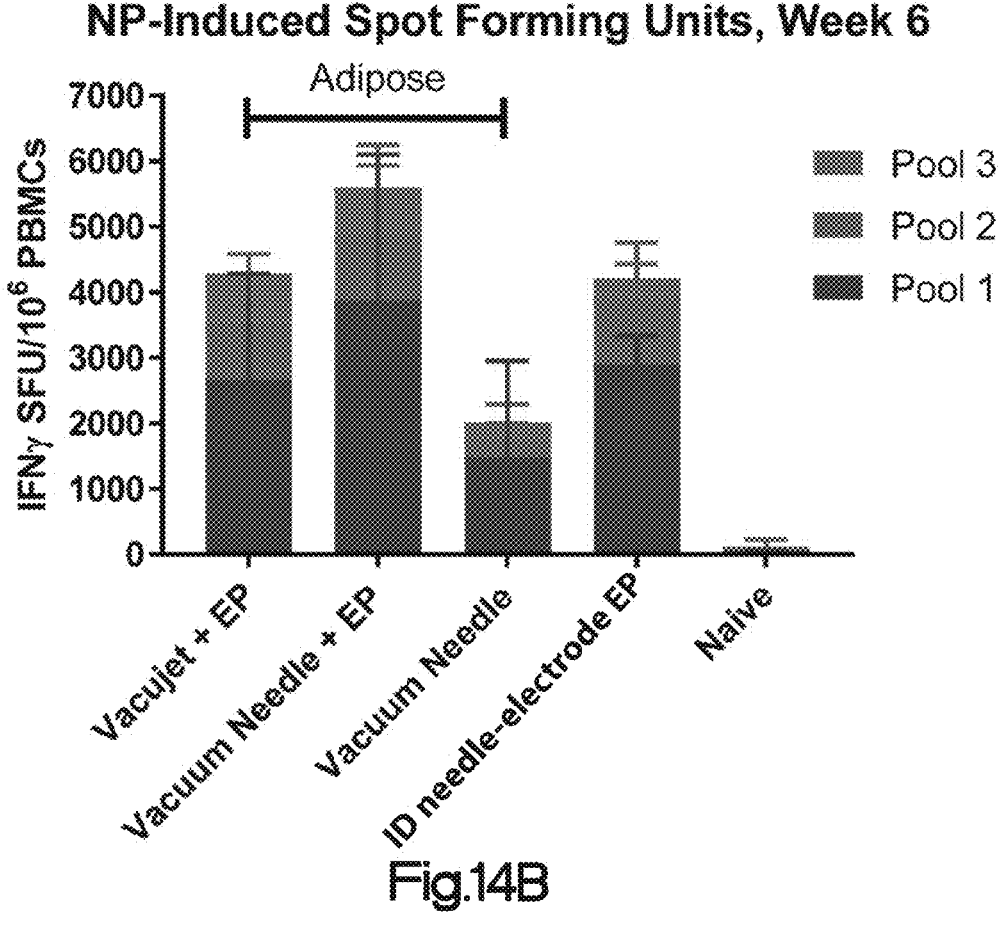
FIG. 14B is a chart showing cellular immune responses from the same study illustrated in FIG. 14A.

Referring now to FIGS. 14A-14B, a 6-week study compares humoral immunogenicity data in guinea pigs after treatments (at weeks 0, 2, and 4) with a DNA vaccine against the influenza nucleoprotein (pGX 2013). FIG. 14A shows ELISA data, while FIG. 14B shows ELISpot data from the same study. The following groups are represented in the graphs: (1) "ID needle-electrode EP" (red plot)—8 ug mantoux injection followed by intradermal electroporation with an intradermal needle-electrode electroporation device: (2) "Vacujet+EP" (blue plot)—40 ug jet injection into adipose tissue followed by vacuum-assisted electroporation using a device similar to that shown in FIG. 9A: (3) "Vacuum Needle" (green plot)—40 ug subcutaneous needle injection into adipose tissue followed by the application of negative vacuum pressure, without electroporation, using the device shown in FIG. 2A; and (4) Vacuum Needle+EP" (purple plot)—40 ug subcutaneous needle injection into adipose tissue followed by vacuum-assisted electroporation using the device shown in FIG. 2A.

These studies demonstrate that the needle-injection, vacuum-electroporation devices 2 and jet-injection, vacuum-electroporation devices 902 described herein produce humoral immune responses when treating adipose tissue that are comparable to the humoral responses produced by treatments with the intradermal needle-electrode electroporation device.

With reference to FIGS. 15A-22, vacuum cups configured to target electroporation in the skin layer 104 will now be described.

Referring now to FIGS. 15A-15B, an example vacuum cup 1502 is shown that includes an electrode array 1509 having one or more annular ring electrodes 1508 and a center electrode 1511 extending along a central axis X of the vacuum cup 1502. The vacuum cup 1502 of the present embodiment is similar to the vacuum cups 2, 502, 702, 802, 902, 1002 described above, particularly the vacuum cup 902 described above with reference to FIGS. 9A-9B. Accordingly, like references numbers as used above denote common features in the present embodiment. For the sake of brevity, the following description focuses on differences between the vacuum cup 1502 of the present embodiment and the vacuum cup 902 described above.

The vacuum cup 1502 of the present embodiment has a housing body 1526 that defines an interior surface 1522 that at least partially defines a vacuum chamber 1506. The housing body 1526 also defines a third port 1516 that extends proximally from the vacuum chamber 1506 along the central axis X. The center electrode 1511 extends through the third port 1516 and into the vacuum chamber 1506 from an end surface portion of the interior surface 1522. The third port 1516 also extends through a mounting formation 1548 for providing sealing engagement with the center electrode 1511. Similar to the manner described above, the mounting formation 1548 can carry one or more sealing members, such as sealing O-rings 1551, that sealing engage an exterior surface 1513 of the center electrode 1511. A distal portion 1513z of the exterior surface 1513 of the center electrode 1511 is configured to contact tissue 102 drawn into the vacuum chamber 1506. Accordingly, the distal portion 1513z can be referred to as a "contact surface" 1513z of the center electrode 1511. The contact surface 1513z can have a rounded profile, such as a hemispherical profile, having a radius R1 in a range of 0.5 mm to about 10 mm, and more particularly in a range of about 1 mm to about 7 mm, and more particularly in a range of about 1 mm to about 4 mm. The central axis X of the vacuum cup 1502 preferably extends through an apex of the contact surface 15132. The center electrode 1511 has a proximal portion 1518, which can be narrower than the portion of the center electrode 1511 in contact with the sealing O-rings 1551. Accordingly, the proximal portion 1518 can be referred to as a "stem" of the center electrode 1511.

Figure 42A:
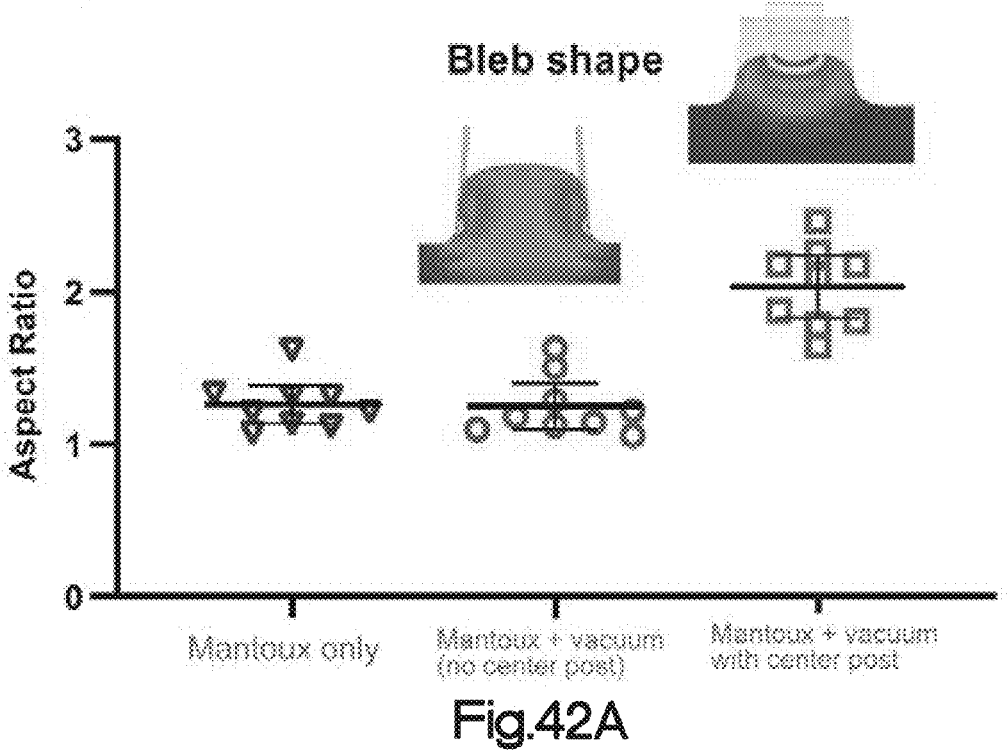
FIG. 42A is a graph showing comparative injectate fluid dispersions following mantoux injection and: (1) no application of vacuum pressure: (2) application of vacuum pressure using a vacuum cup having the electrode array shown in FIG. 40A; and (3) application of vacuum pressure using a vacuum cup having the electrode array shown in FIG. 40B.

Referring now to FIG. 15C, the electrode array 1509 is configured such that, during electroporation pulse delivery, the center electrode 1511 acts as a positive or negative electrode while one or both of the annular ring electrodes 1508 acts as the other of the positive or negative electrode (i.e., the opposite polarity of the center electrode 1511). In this manner, the center electrode 1511 effectively moves the electric field 145 during the pulse(s) upwards, focusing the electroporation field 144 in the skin layer 104. The vacuum cup 1502 of the present embodiment can be placed on the tissue 102 at the target zone after the agent has been injected in the skin layer 104, such as via needle injection, such as a Mantoux injection, for example, or an intradermal jet injection. It should be appreciated that, in other embodiments, the vacuum cup 1502 can employ a feature or "post" in place of the center electrode 1511. The post can present a surface that is shaped similar to surface 1513z within the vacuum chamber 1506. The post surface is configured to contact the skin drawn into the chamber 1506 via vacuum pressure. For example, the post can be configured to cause the tissue to conform or otherwise bend around a portion of the post surface during application of the vacuum pressure. Such tissue-post contact has been shown to advantageously enhance fluid dispersion in the tissue during application of vacuum pressure, as discussed in more detail below with reference to FIGS. 42A and 42D.

Referring now to FIG. 16A, versions of a vacuum-electroporation assembly 1600 are shown that each include a vacuum cup 1602 having an electrode array 1609 positioned on an end surface 1624 within the vacuum chamber 1606 opposite a distal opening 1620 thereof. The end surface 1624 can be substantially flat, and can be defined by an electrode support member 1652 positioned within the chamber 1606. The support member 1652 can be referred to as an "insert" and can carry the electrodes 1608 of the array 1609. For example, the support member 1652 can be a circuit board, such as a printed circuit board (PCB), having circuitry in electrical communication with a control unit, such as the controller 114 described above. The support member

1652 also defines a plurality of ports 1660 extending therethrough providing fluid communication between the vacuum chamber 1606 and an external port 1616 for connection to a vacuum source. In this manner, the ports 1660 in the support member 1652 communicate vacuum pressure into the chamber 1606, drawing tissue 102 therein and into contact with the electrodes 1608. The electrodes 1608 can have protruding and/or tipped geometries, such as conical, pyramidal, and the like, for pressing into the skin layer 104 of the tissue mound 140 draw in into the chamber 1606, thereby disrupting and altering the top layer of the skin 104, improving the electric field distribution therein, as described above.

The vacuum-electroporation assembly 1600 can be configured to receive an injection device, such as a needle-free injection device, such as the jet injection device 970 described above. Accordingly, the vacuum cup 1602 has a housing body 1626 that can define a receptacle 1616 for receiving at least the distal portion of the jet injection device 970, such that the nozzle 978 thereof is aligned with an injection aperture 1617 defined in the support member 1652. As shown, the nozzle 978 and the injection aperture can be concentrically aligned with the central axis of the vacuum cup 1602.

The housing body 1626 can also define a secondary or "stand-off" chamber 1607 offset from the vacuum chamber 1606, such that the support member 1652 separates or is interposed between the vacuum chamber 1606 and the stand-off chamber 1607. The stand-off chamber 1607 is configured to provide a stand-off distance L5 between the distal end of the nozzle 978 and the end surface 1624 for allowing a favorable formation of the injectate 142 stream between the nozzle 978 and the tissue 102 for purposes of intradermal dispersion of the injectate 142. In particular, the stand-off distances L5 can allow irregularities to form in the liquid stream as it approaches the skin 104. For example, such irregularities can include hundreds, thousands, or even greater numbers of micro- and/or nano-sized droplets, each approaching the skin 104 at velocities sufficient to effectively allow the stream to for hundreds or thousands of micro- and/or nano-sized cuts in the outer surface 101 of the skin 104, providing enhanced injectate dispersion localized in the skin layer 104. The stand-off distance L5, in conjunction with other factors such as jet injector nozzle geometry and injector force, can also be used a means of controlling the maximum penetration depth of the injectate. It should be appreciated that the stand-off distance L5 can also be characterized as a minimum stand-off distance between the distal end of the nozzle 978 and the outer surface 101 of the skin 104 during use. The stand-off distance L5 can be in a range from about 1.0 mm to about 20 mm.

As shown in FIG. 16B, the housing body 1626 can optionally define a cannulated shield 1685 that extends through the stand-off chamber 1607 and can abut a rear surface 1625 of the support member 1652 such that the cannulation of the shield 1685 is in fluid communication with the injection aperture 1617 of the support member 1652. In this manner, the cannulated shield 1685 can provide a straight, aligned, shielded passage from the distal end of the nozzle 978 to the vacuum chamber 1606, thereby protecting the support member 1652 (and its circuitry) from inadvertent exposure to the injectate stream.

Referring now to FIGS. 17A-17B, different embodiments of the support member 1652 are shown, in which the electrodes 1608 and ports 1660 are arranged in different patterns around the injection aperture 1617. As shown in FIG. 17A, the electrodes 1608 can be arrayed in a circular or ring pattern along a circumferential axis C2 concentric with the central axis X. The electrodes 1608 can be arrayed in a single concentric ring, or, as shown in FIG. 17B, can be arrayed in multiple rings which can be concentric with the central axis X or, alternatively, eccentric with respect to the central axis X. With continued reference to FIG. 17B, the ports 1660 can also be arranged in one or more annular rings about the central axis X. Moreover, the electrodes 1608 and/or the ports 1660 can also (or alternatively) be arranged in spoke patterns along respective axes R4, R5, extending radially outward from the central axis X. The respective axes R4, R5 of adjacent electrode 1608 "spokes" and adjacent port 1660 spokes can be offset from each other at respective angular intervals A5, A6 about the central axis, which can range from about 5 degrees to about 180 degrees, and more particularly from about 15 degrees to about 120 degrees. The axes R4, R5 can be linear, as shown, although in other embodiments the axes R4, R5 can be arcuate. It should be appreciated that the example electrode 1608 and port 1660 patterns are provided as non-limiting examples, and that other patterns, including asymmetrical and/or irregular patterns, are also within the scope of the present disclosure.

Figure 18A:
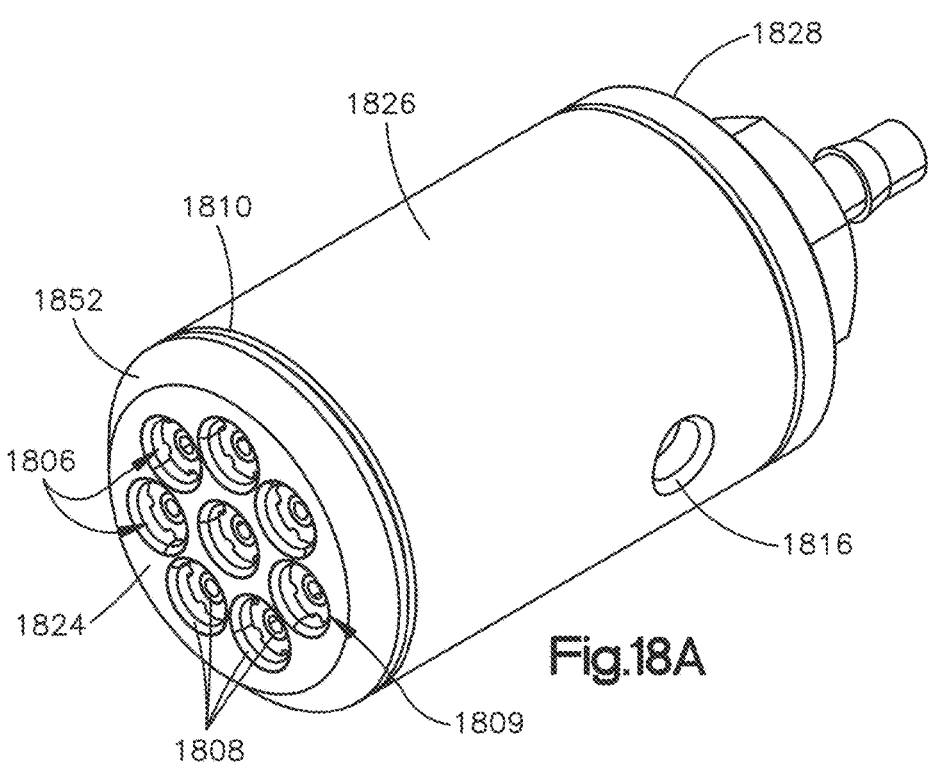
FIG. 18A is a perspective view of a vacuum-electroporation device having a plurality of distal vacuum chambers.
Figure 18B:
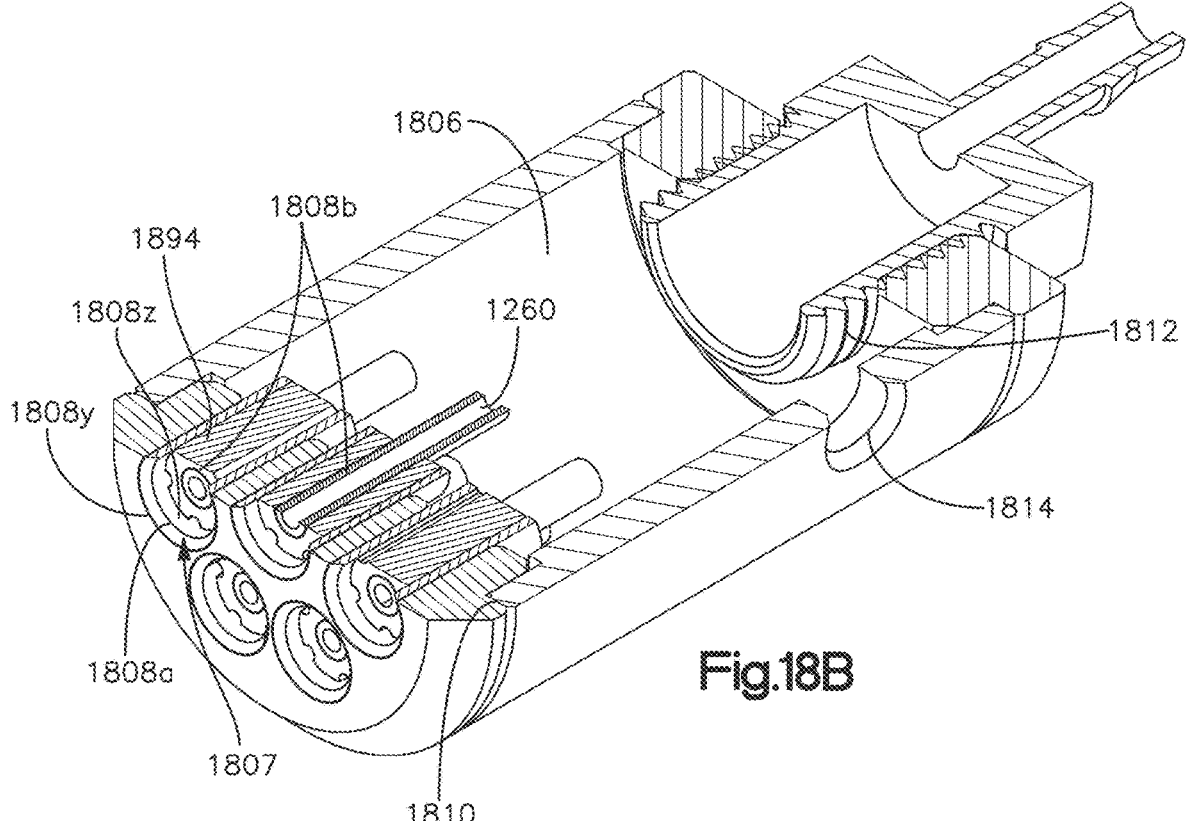
FIG. 18B is a sectional perspective view of the vacuum-electroporation device illustrated in FIG. 18A.

Referring now to FIGS. 18A-18B, in further embodiments, a vacuum electroporation device 1802 can include a plurality of distal vacuum chambers 1807 for induction of tissue therein, particularly skin. The electrodes 1808 are carried by an electrode support member 1852, which can be attached to a distal end 1810 of a vacuum housing body 1826 that defines a main vacuum chamber 1806. In this manner, a distal end surface 1824 of the support member 1852 defines a distal end of the device 1802. The housing body 1826 defines a main vacuum port 1812 for providing vacuum pressure to the main vacuum chamber 1806, and can define a second port 1814, such as for providing access for circuitry to extend within the main vacuum chamber 1806 and to the support member 1852.

Referring now to FIG. 18B, the electrodes 1808 of the present embodiment are arranged into pairs, each including an outer ring electrode 1808a and an inner ring electrode 1808b concentrically located with respect to each other. The outer and inner ring electrodes 1808a,b can be tubular members elongated along the longitudinal direction L and extend through the support member 1852 to a rear surface 1825 thereof, and optionally further into the main vacuum chamber 1806. The outer and inner ring electrodes 1808a,b of each pair are radially spaced from each other by an electrically insulative, annular layer 1894 of material, thereby electrically isolating the inner and outer ring electrodes 1808a,b from each other. In each concentric electrode pair, the outer ring electrodes 1808a extend to the distal end surface 1824 of the support member 1852, while the inner ring electrodes 1808b are proximally recessed from the distal end surface 1824. In this manner, the distal vacuum chambers 1807 are cooperatively defined by inner surfaces 1808z of the outer ring electrodes 1808a, distal ends of the inner ring electrodes 1808b, and distal end surfaces of the insulative layers 1894, and optionally also be optional distal lead-in surfaces 1808y of the outer ring electrodes 1808a.

As shown in FIGS. 18C-18D, the distal ends of the inner ring electrodes 1808b (and optionally also the distal ends of the insulative layers 1894) can be recessed from the distal surface 1824 at an offset distance L6, which can be in a range of about 0.05 mm to about 5.0 mm, and more particularly in a range of about 0.5 mm to about 2.0 mm, and preferably in a range of about 0.8 mm to about 1.2 mm. The device can define a device length L7 measured from the proximal end 1828 to the distal end surface 1824 along the longitudinal direction L. The device length L7 can be in a range of about 15.0 mm to about 200 mm, and more particularly in a range of about 20 mm to about 40 mm, although lengths L7 smaller than 15.0 mm and greater than 200 mm are also within the scope of the present embodiment.

As mentioned above, the inner ring electrodes 1808b can be tubular, particularly in a manner defining a port 1860 providing fluid communication with the main vacuum chamber 1806. In this manner, vacuum pressure applied to the main vacuum chamber 1806 is communicated to the distal vacuum chambers 1807 through the inner ring electrodes 1808b, thereby allowing the device 1802 to draw portions of the skin layer 104 into the distal vacuum chambers 1807 and into contact with the inner and outer ring electrodes 1808a,b. Such deformation of the skin layer 104 can disrupt and alter the top portion thereof, thus improving the electric field distribution within the skin layer 104, similar to the manner described above.

The inner and outer ring electrodes 1808a,b of each pair are preferably of opposite polarity, such the electroporation pulse(s) are delivered from one of the ring electrodes 1808a,b, through the tissue, and to the other of the ring electrodes 1808a,b of the pair.

As shown in FIG. 18, the electrode array 1809 can be a circular array that includes a central electrode pair 1808a,b and a circular pattern of peripheral electrode pairs 1808a,b arranged along a circumferential axis C2 concentrically around the central electrode pair 1808a,b. It should be appreciated that other array patterns are within the scope of the present embodiment. Adjacent electrode pairs 1808a,b of the periphery can be spaced from each other at respective angular intervals A5, similar to the manner described above.

Figures 19A, 19B, 20, 21A, 21B:
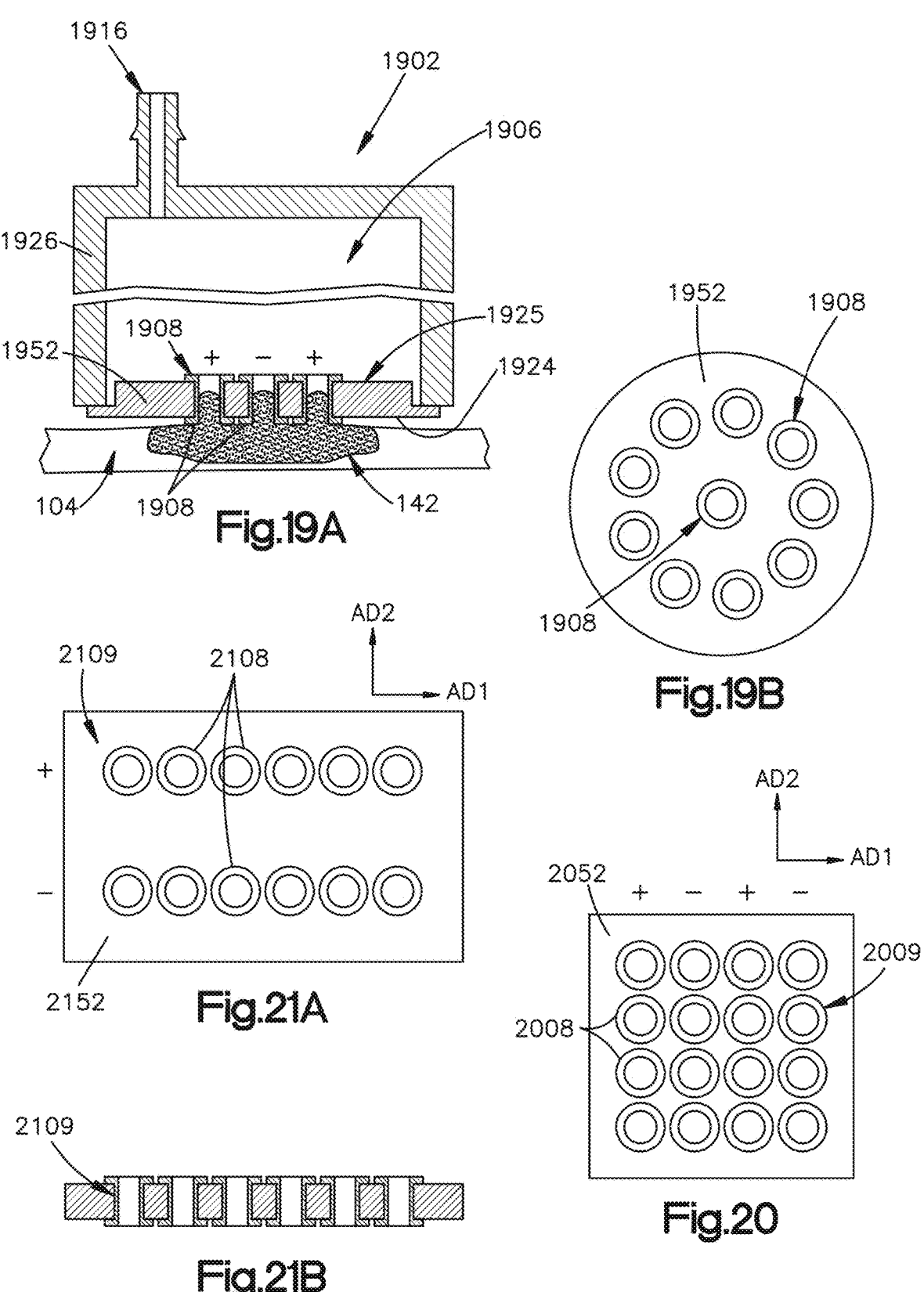
FIG. 19A is a sectional side view of a vacuum-electroporation device having a distal array of electrodes having vacuum ports therein, according to an embodiment of the present disclosure.
FIG. 19B is a bottom plan view of the vacuum-electroporation device illustrated in FIG. 19A, showing a plan view of the electrode array pattern, according to an embodiment of the present disclosure.
FIG. 20 is a plan view of an electrode support member having a square electrode array configured for use with a vacuum-electroporation device similar to that illustrated in FIG. 19A.
FIG. 21A is a plan view of an electrode support member having a rectangular electrode array that is otherwise similar to the electrode support member illustrated in FIG. 20.
FIG. 21B is a side sectional view of the electrode support member illustrated in FIG. 21A.

Referring now to FIGS. 19A-19B, in further embodiments, a vacuum electroporation device 1902 can include an electrode support member 1952 at a distal end 1910 of a housing body 1926, similar to the device 1802 of the embodiment above. In the present embodiment, each electrode 1908 is tubular and extends through the support member 1924 from a distal end surface 1924 thereof to a rear surface 1925 thereof, thereby defining a port 1960 in fluid communication with a vacuum chamber 1906 of the housing body 1926. The ports 1960 of the electrodes 1908 are sized so that an outer portion of the skin layer 104 can extend into the ports 1960 responsive to vacuum pressure in the vacuum chamber 1906. Each electrode 1908 of the present embodiment is a single-polarity (positive or negative) during an electric pulse. The electrodes 1908 are connected to circuitry that can deliver the electroporation signal such that, during an electric pulse, one or more of the electrodes 1908 is one polarity (positive or negative) while one or more of the other electrodes 1908 is the opposite polarity. For example, with continued reference to FIGS. 19A-19B, the electrodes 1908 can be arranged in a circular electrode array 1908 that includes a central electrode 1908 and a circular pattern of peripheral electrodes 1908 arranged concentrically around the central electrode 1908. One or more and up to each of the electroporation pulses can be delivered between the central electrode 1908 and at least one of the peripheral electrodes 1908. The electroporation signal can include a plurality of electroporation pulses delivered in a sequence employing a decentralized pattern of the electrodes 1908, similar to the manner described above.

Referring now to FIGS. 20 and 21A-21B, electrode support members 2052, 2152 can carry electrode arrays 2009, 2109 having non-circular patterns. As shown in FIG. 20, the support member 2052 can have a square electrode array 2009 that is substantially equidistance along first and second array directions AD1, AD2 that are substantially perpendicular to each other. In the illustrated embodiment, the array 2009 has a 4×4 array pattern, although other square array patterns are within the scope of the present disclosure, including, by way of non-limiting examples, 2×2, 3×3, 5×5, 6×6, 7×7, 8×8, 9×9, 10×10, etc.

As shown in FIGS. 21A-21B, the support member 2152 can have a rectangular electrode array 2109 that is longer along the first array direction AD1 than along the second array direction AD2. The array 2109 can include, for example, a first row of electrodes and a corresponding second row of electrodes, such as in a 2×6 (i.e., 2 rows by 6 columns) array 2109, although other rectangular array 2109 patterns are within the scope of the present disclosure, including, by way of non-limiting examples, 1×2, 1×3, 1×4, 2×3, 2×4, 2×5, 2×7, 2×8, 2×9, 2×10, 3×4, 3×5, 3×6, 3×7, 3×8, 3×9, 3×10, 4×5, 4×6, 4×7, 4, 8, 4×9, 4×10, 5×6, 5×7, 5, 8, 5×9, 5×10 electrode arrays 2109.

It should be appreciated that the square and rectangular electrode arrays 2009, 2109 described above can have virtually any number of electrodes 2008, 2108 arranged in their respective patterns. Such square and rectangular electrode arrays 2009, 2109 can produce a generally rectangular electric field that can be activated in a row- or column-wise fashion, allowing highly ordered electric fields along a given axis. For example, if injectate is intentionally injected, or happens to accumulate, along one axial direction of a tissue, additional rows or columns of electrodes 2008, 2108 can easily be activated to treat the desired tissue volume. In this regard, these electrode arrays 2009, 2109 can be characterized as providing a modular activation functionality. Additionally, a rectangular electrode array 2109 can be placed on the skin 104 over the target zone such that the first array direction AD1 (along which the array is elongate) is substantially aligned with the axis along which fluid was intentionally injected, or where fluid naturally distributed due to the presence of anisotropic features such as fibrous tissue, thereby encapsulating the injectate within the electroporation field for a longer duration as the injectate disperses through the tissue. Moreover, because the array 2109 also defines the array of vacuum ports, which disrupt the top layers of the skin 104 during application of vacuum pressure, the rectangular array 2109 can also effectively form disruption pathways in the intradermal tissue that further channel the dispersing injectate along the electroporation field.

Figure 22:
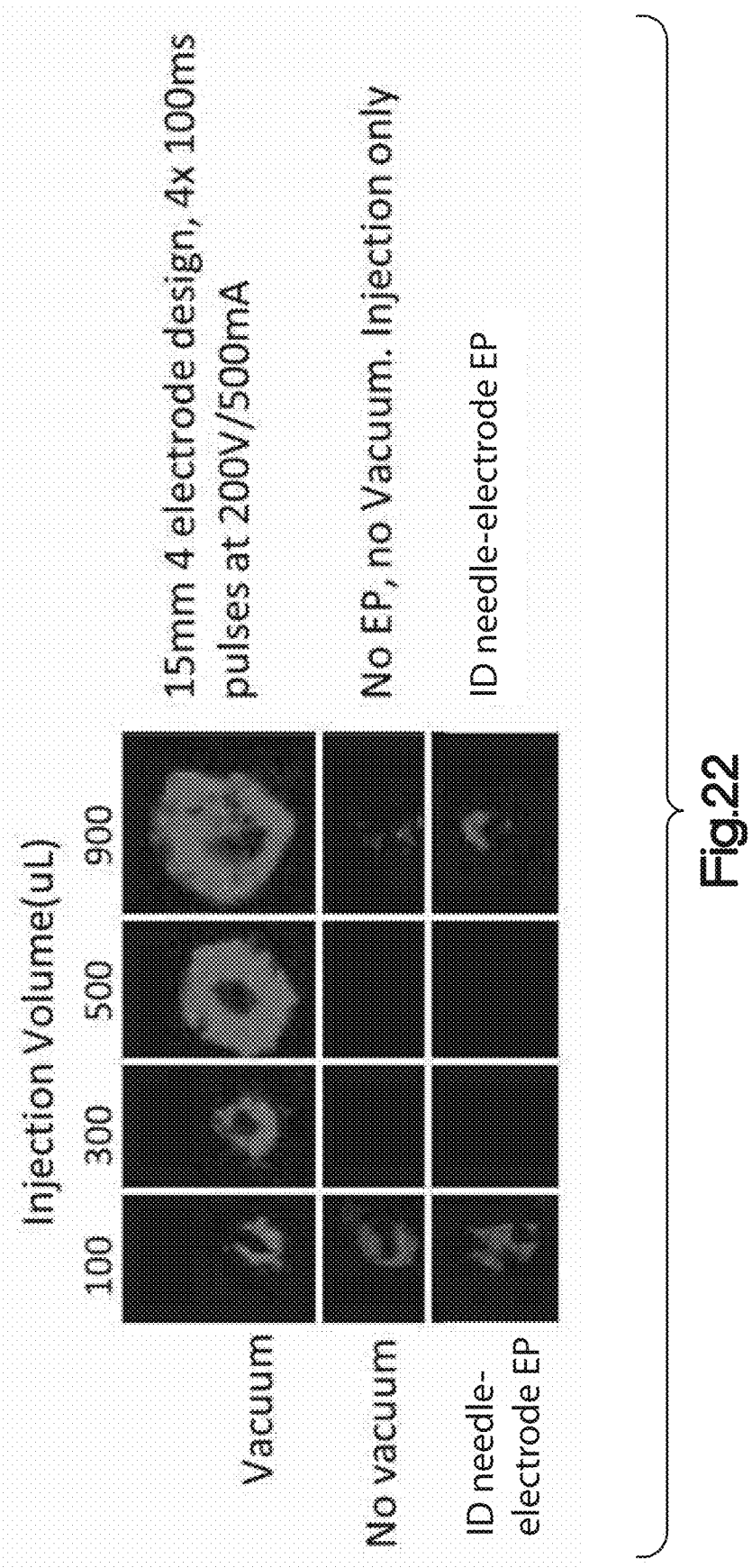
FIG. 22 is a diagram showing gene expression in guinea pig skin after intradermal injections of various volumes of a plasmid encoding the gene for green fluorescent protein (GFP) and then treated with various techniques and devices.

Referring now to FIG. 22, gene expression in guinea pig skin is shown after intradermal injections of various volumes of a plasmid encoding the gene for green fluorescent protein (GFP) and then electroporation treatments with various devices. In this study, at injection volumes of 100 uL, 300 uL, 500 uL, and 900 uL, vacuum-assisted electroporation of intradermal tissue using the vacuum cups 2, 902 described herein significantly increased gene expression in a manner proportional to injection volume. In a similar study, the inventors found that gene expression for GFP also increased with increased vacuum pressure. In contrast, gene expression using an intradermal needle-electrode electroporation device was not enhanced with increased injection volume. Further, increased injection volume alone in the absence of vacuum application or electroporation did not enhance gene expression. These studies demonstrate that vacuum pressure and injection volume influence gene expression.

Figure 35A:
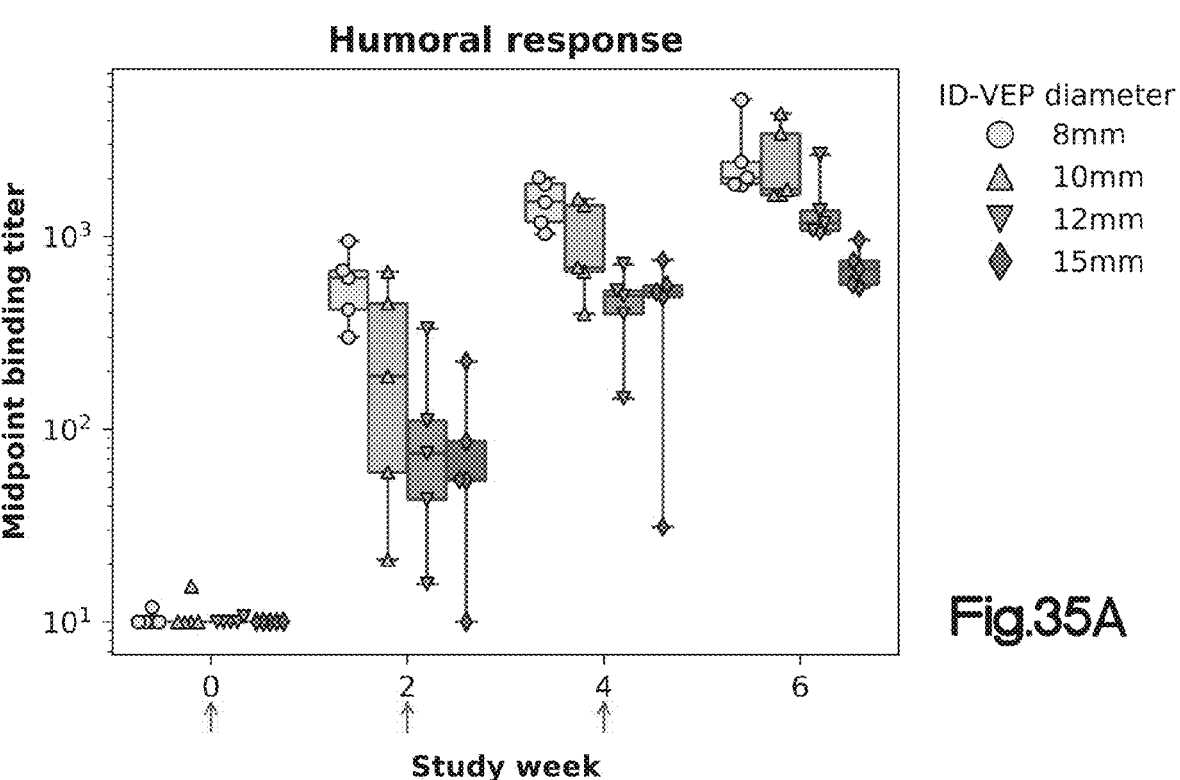
FIG. 35A is a graph showing 6-week humoral immunogenicity data in guinea pigs after treatments with a DNA vaccine against MERS, particularly showing comparative humoral immune responses following respective electroporation treatments in skin using vacuum cups similar to that illustrated in FIG. 2A and having various chamber diameters and the same electroporation parameters.
Figure 35B:
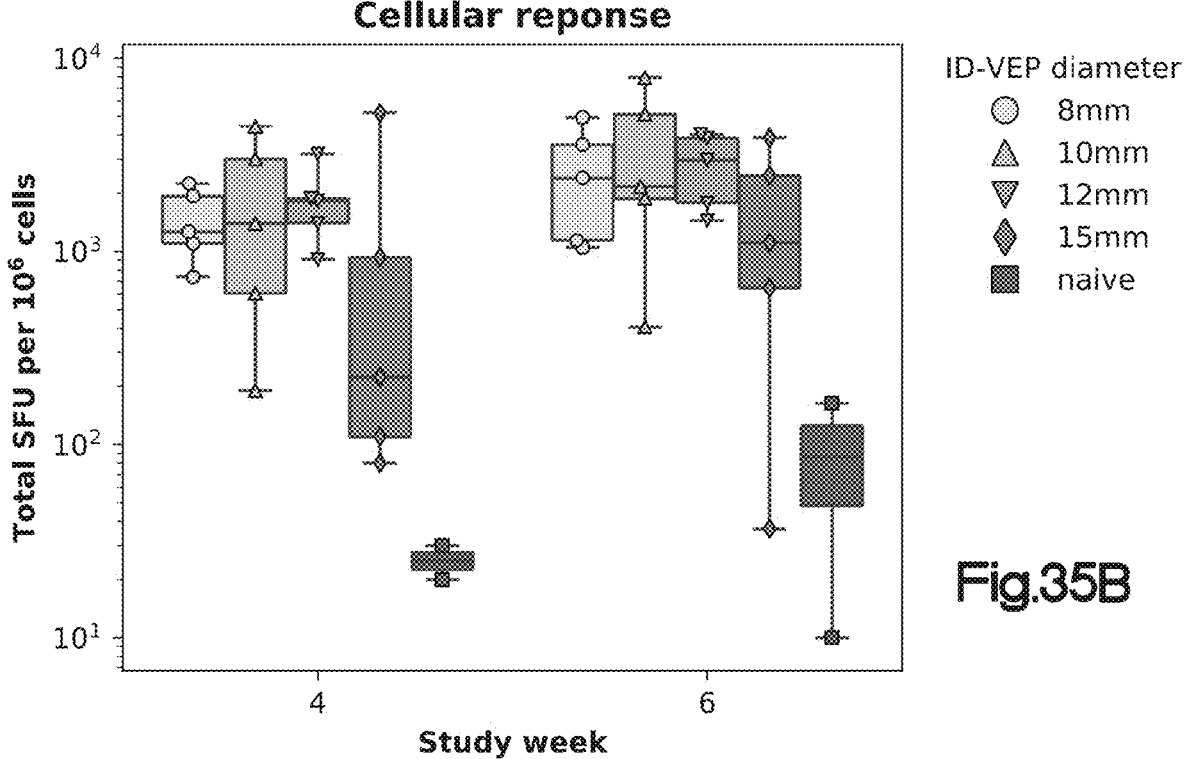
FIG. 35B is a chart showing cellular immune responses from the same study illustrated in FIG. 35A.

Referring now to FIGS. 35A-35B, a 6-week study evaluated the effects of chamber diameter D1 on immunogenicity in guinea pig skin at a given electroporation voltage and current using a vacuum-assisted electroporation device. FIG. 35A compares humoral immunogenicity ELISA data following intradermal vacuum-assisted electroporation treatments using vacuum cups having chamber diameters D1 of 8 mm, 10 mm, 12 mm, and 15 mm. The intradermal treatments for each vacuum cup included a 50 ug mantoux injection of a MERS DNA vaccine followed by electroporation using the same voltage and current. FIG. 35B shows cellular immune response ELISpot data at weeks 2 and 4 during the same study illustrated in FIG. 35A. This study demonstrates a direct, inverse correlation between humoral immune response and vacuum cup diameter at a given electroporation voltage and current limits. In terms of cellular immune response, this study also demonstrates that the vacuum cups having chamber diameters D1 from 8 mm to 12 mm produced similar results, with a decrease in cellular response occurring when the diameter D1 increased from 12 mm to 15 mm.

Figure 36A:
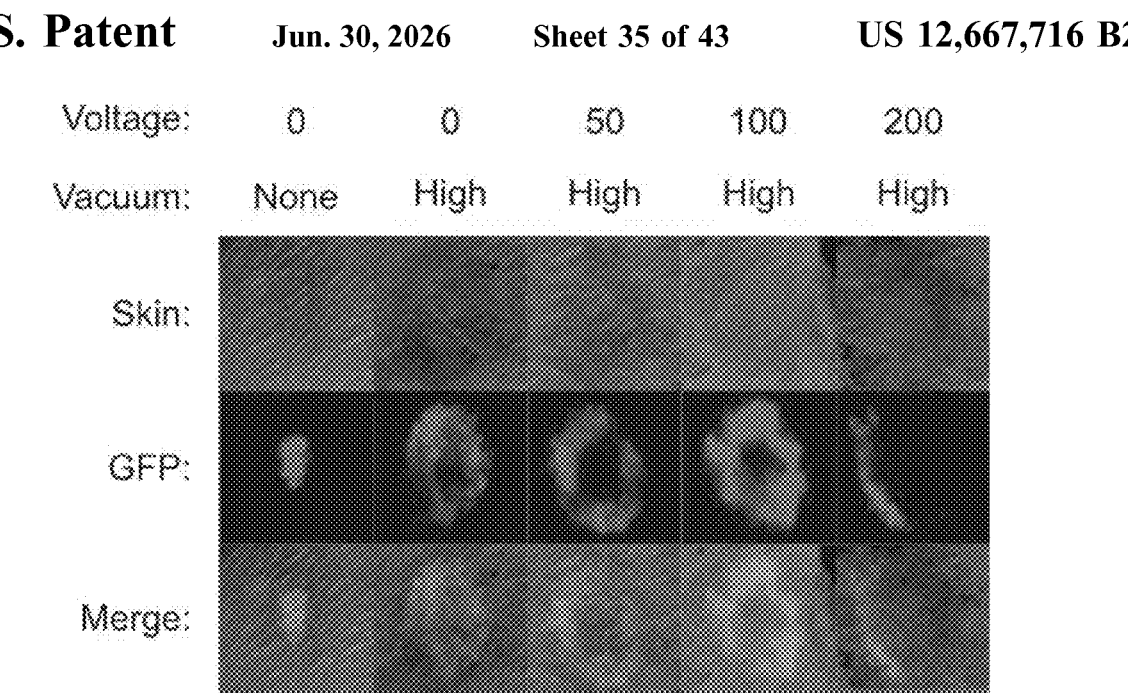
FIG. 36A is a diagram showing gene expression in guinea pig skin after intradermal injections of a plasmid encoding the gene for green fluorescent protein (GFP) and then treated at various vacuum pressures and electroporation voltages using a vacuum cup.
Figure 36B:
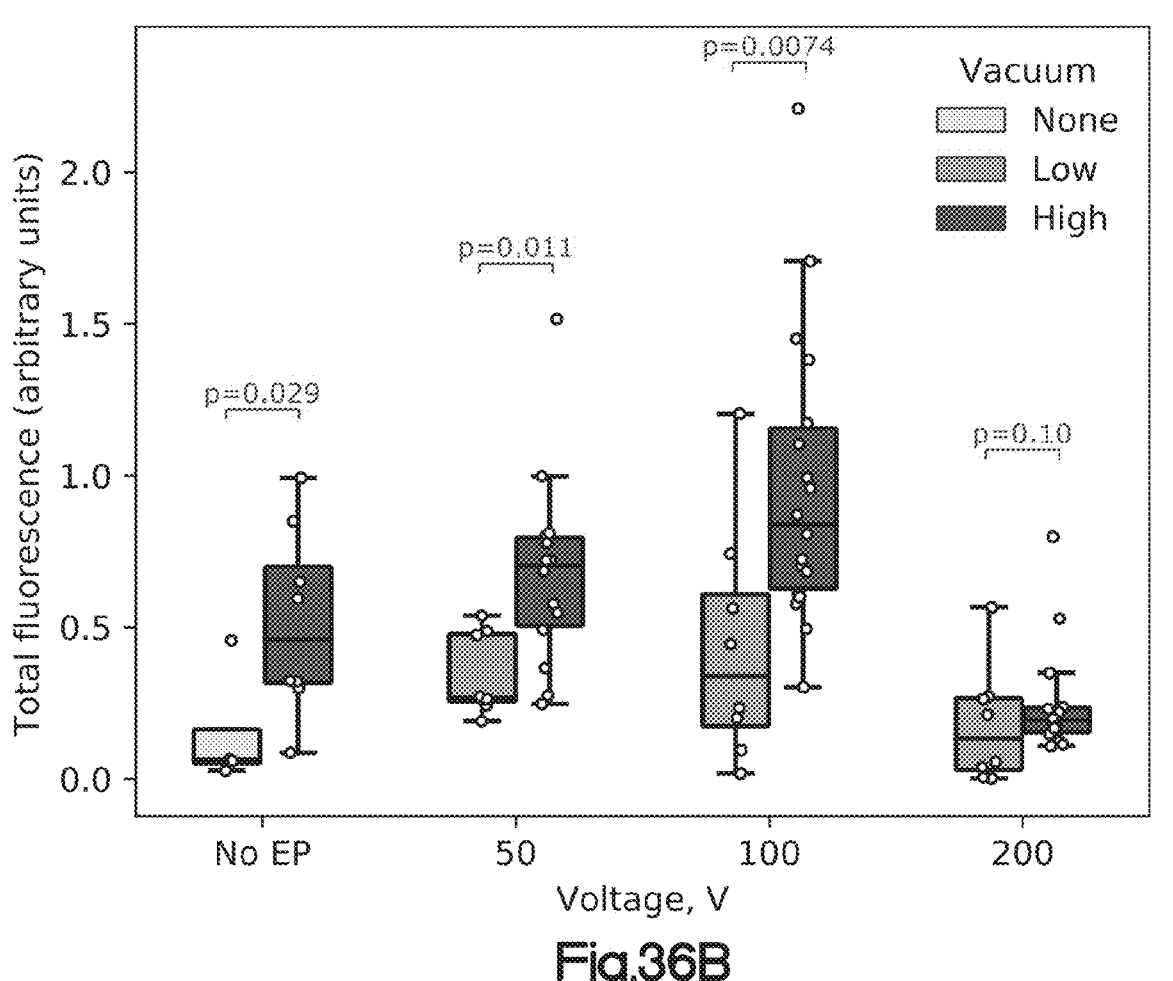
FIG. 36B is a graph showing measurements of the skin fluorescence signal from the results of GDF expression illustrated in FIG. 36A.

Referring now to FIGS. 36A-36B, a study evaluated favorable combinations of vacuum pressure and electroporation voltage parameters on gene expression in guinea pig skin. These studies employed intradermal injections (specifically, mantoux injection) of a plasmid encoding the gene for green fluorescent protein (GFP) and then performed electroporation treatments at various vacuum pressures and voltages using a vacuum cup similar to the cup 2 described above. Vacuum pressures of 0 kPa (no vacuum), 40 kPa, and 70 kPa and voltages of 0 V (no voltage), 50 V, 100 V, and 200 V were applied to the skin. The treatment site reactions and GFP expression were observed at 3-days following the treatments. FIG. 36A shows visual observations of the treatment site at the various vacuum pressures and voltages. In FIG. 36B, measurements of the skin fluorescence signal are plotted for the various voltages and vacuum pressures. These studies demonstrate that vacuum pressure and voltage independently increase GFP expression. These studies also demonstrate that, at each voltage tested, higher vacuum pressure enhanced GFP expression.

Figure 23:
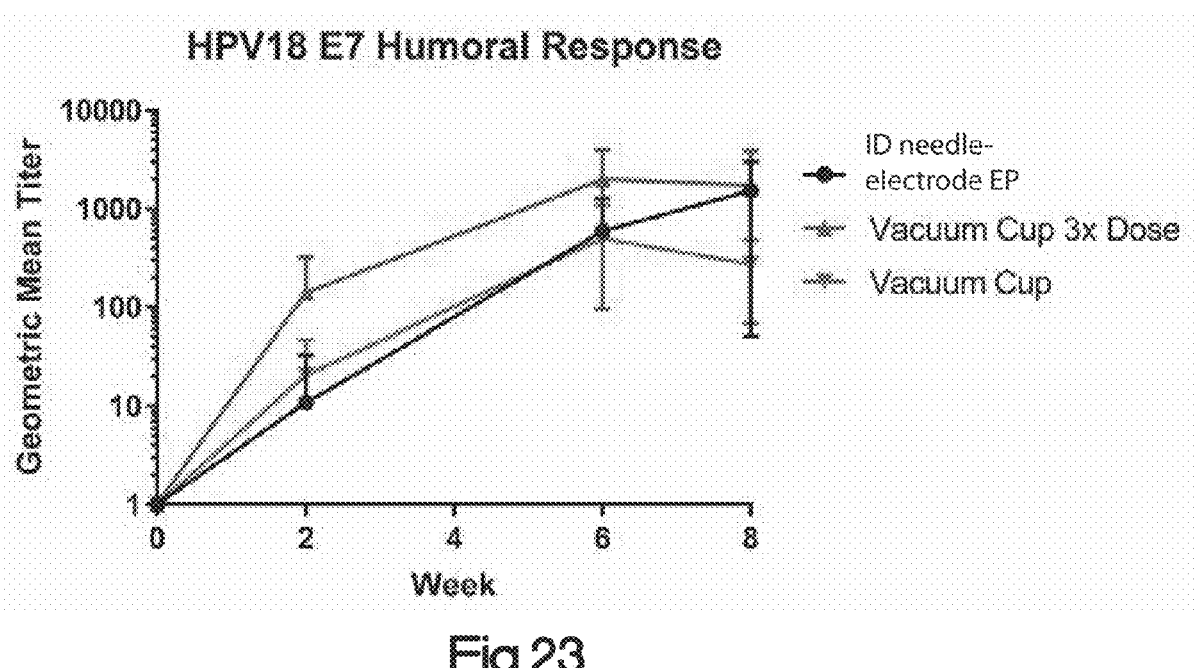
FIG. 23 is a graph showing 8-week humoral immunogenicity ELISA data in guinea pigs after treatments of an HPV DNA vaccine, particularly showing comparative humoral immune responses following respective electroporation treatments in skin using: a prior art needle-array electroporation device; the vacuum cup illustrated in FIG. 2A; and the vacuum cup illustrated in FIG. 2A with three times (3×) the dosage of the other treatments.

Referring now to FIG. 23, an 8-week study compares humoral immunogenicity ELISA data in guinea pigs after intradermal treatments of an HPV DNA vaccine followed by electroporation. The following groups are represented: (1) "ID needle-electrode EP" (black plot)—treatments using the intradermal needle-electrode electroporation device after a 100 uL mantoux injection of 66.7 ug of plasmid: (2) "Vacuum Cup" (red plot)—treatments using a 15 mm vacuum cup electroporation device that consisted of 4 wall electrodes (see, e.g., FIG. 2A) after a 1 mL injection of an equivalent dose of 66.7 ug of plasmid which was also formulated with 139 U/ml of Hylenex: (3) "Vacuum Cup 3× Dose" (maroon plot)—treatments using the same device and method as the "Vacuum Cup" group, but dosage was increased to 3 times that of the previously mentioned groups, which was 200 μg of plasmid. All groups were treated at weeks 0, 4, and 7.

Figure 24A:
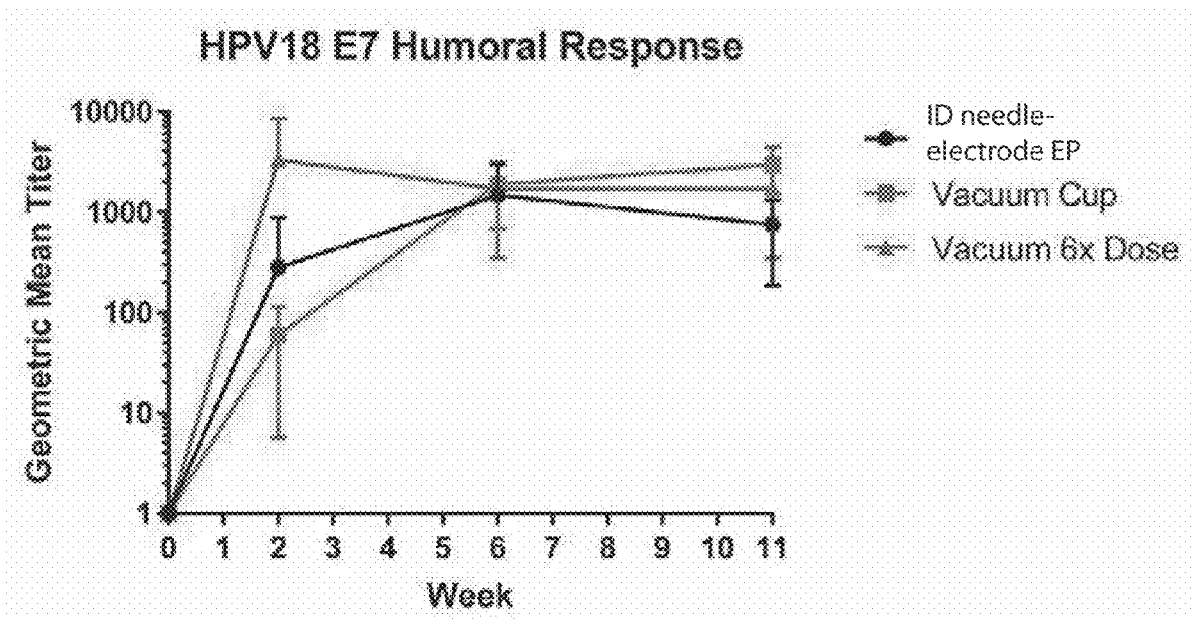
FIG. 24A is a graph showing 11-week humoral immunogenicity ELISA data in non-human primate models after treatments of an HPV DNA vaccine (pGX 3001&3002), particularly showing comparative humoral immune responses following respective electroporation treatments in skin using: a prior art needle-array electroporation device; the vacuum cup illustrated in FIG. 2A; and the vacuum cup illustrated in FIG. 2A with three times (3×) the dosage of the other treatments.
Figure 24B:
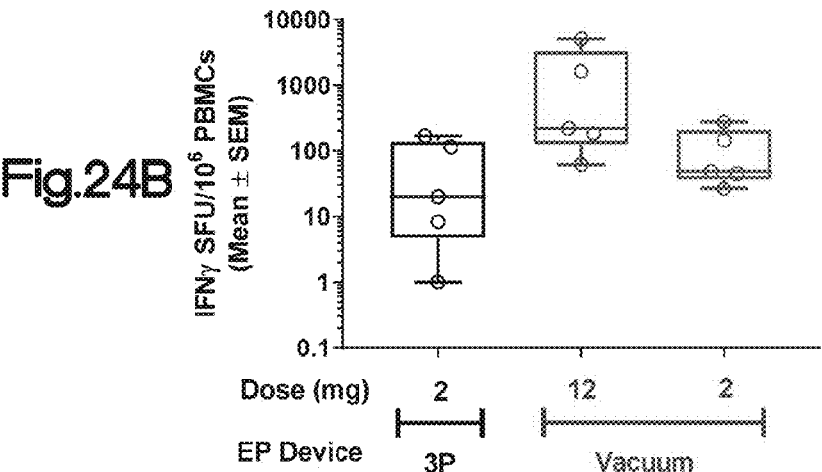
FIGS. 24B, 24C, and 24D are charts showing cellular immune responses from the same study illustrated in FIG. 24A.
Figure 24C:
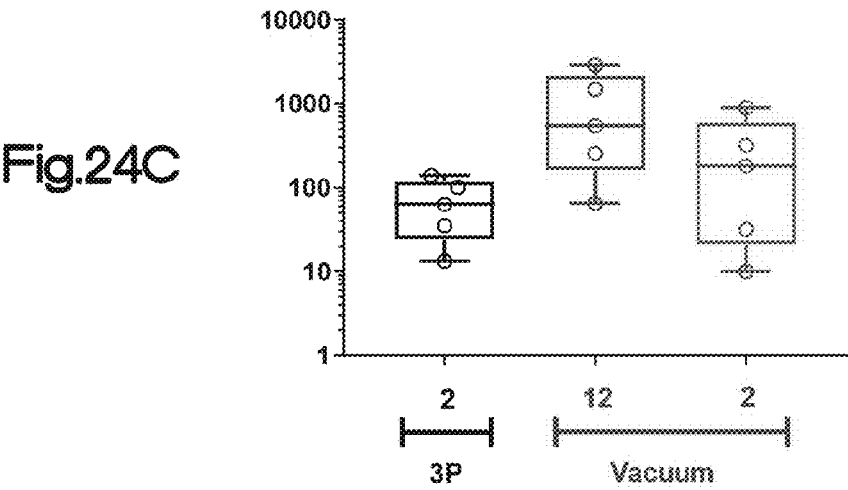
Figure 24D:
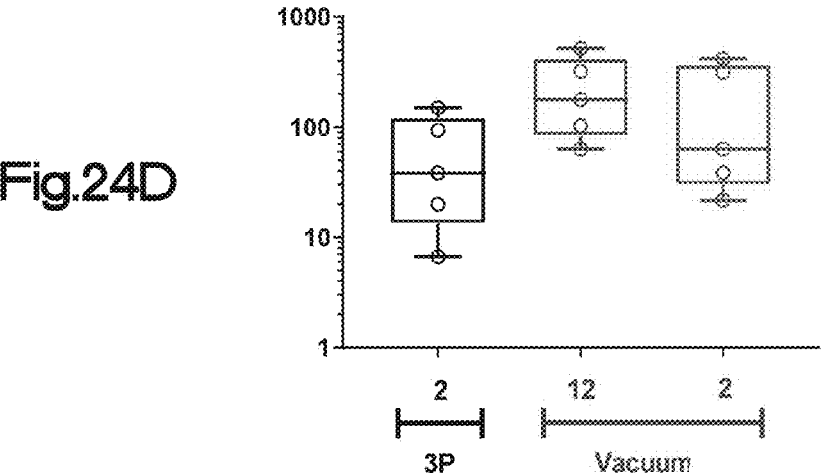

Referring now to FIG. 24A, an 11-week study compares humoral immunogenicity ELISA data in non-human primates after intradermal treatments of an HPV DNA vaccine (pGX 3001&3002) followed by electroporation. The following groups are represented: (1) "ID needle-electrode EP" (black plot)—treatments using the intradermal needle-electrode electroporation device: (2) "Vacuum Cup" (red plot)—treatments using the vacuum cup shown in FIG. 2A after injection of an equivalent dose as in "ID needle-electrode EP"; (3) "Vacuum Cup 6× Dose" (maroon plot)—treatments using the same device and method as the "Vacuum Cup" group, but dosage was increased to 6 times that of the previously mentioned groups. All groups were treated at weeks 0, 4, and 9. Referring now to FIGS. 24B-24D, cellular immune response ELISpot data is shown for each group at weeks 2, 6, and 11, respectively, of the same study shown in FIG. 24A. These studies demonstrate that the high-dose vacuum-assisted electroporation treatment (Group 3) produced a more rapid humoral and cellular response than the ID needle-electrode EP device (Group 1) while, at equivalent-doses, the vacuum-assisted electroporation treatment (Group 2) performed generally similar to the ID needle-electrode EP device (Group 1). Moreover, the high-dose vacuum-assisted electroporation treatment (Group 3) produced a cellular response at eleven (11) weeks about ten-times (10)×) greater than that of the ID needle-electrode EP device (Group 1).

Figure 37A:
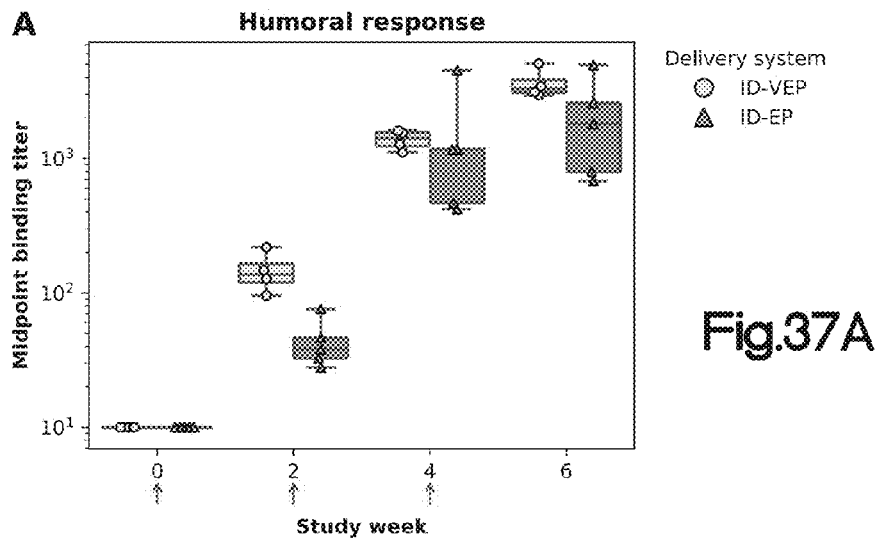
FIG. 37A is a graph showing 6-week humoral immunogenicity ELISA data in guinea pigs after treatments with a DNA vaccine against MERS, particularly showing comparative humoral immune responses following respective electroporation treatments in skin using: (1) a prior art needle-array electroporation device; and (2) a vacuum cup similar to that illustrated in FIG. 2A.
Figure 37B:
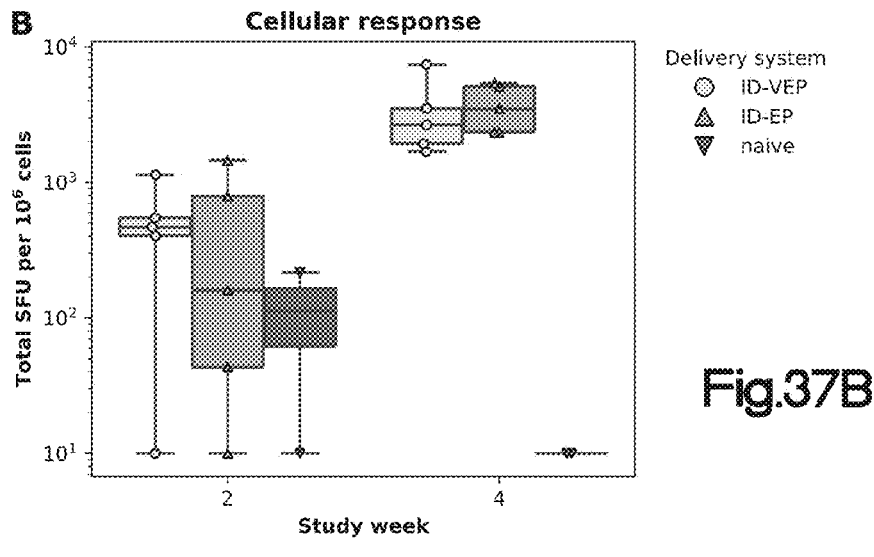
FIG. 37B is a chart showing cellular immune responses from the same study illustrated in FIG. 37A.

Referring now to FIGS. 37A-37B, a 6-week study compared the performance of a vacuum-assisted electroporation device against an intradermal needle-electrode electroporation device in terms of immunogenicity. FIG. 37A compares humoral immunogenicity ELISA data in guinea pigs after intradermal treatments with 50 μg of a MERS DNA vaccine via mantoux injection followed by electroporation. The groups represented in the graph are: (1) "ID-VEP"—treatments using a vacuum cup similar to that shown in FIG. 2A; and (2) "ID-EP" treatments using an intradermal needle-electrode electroporation device. Both groups were treated at weeks 0, 2, and 4. This study demonstrates that the vacuum cup generates a more rapid vet stronger humoral response compared to the intradermal needle-electrode electroporation device. FIG. 37B shows cellular immune response data at weeks 2 and 4 during the same study illustrated in FIG. 37A.

Figure 38:
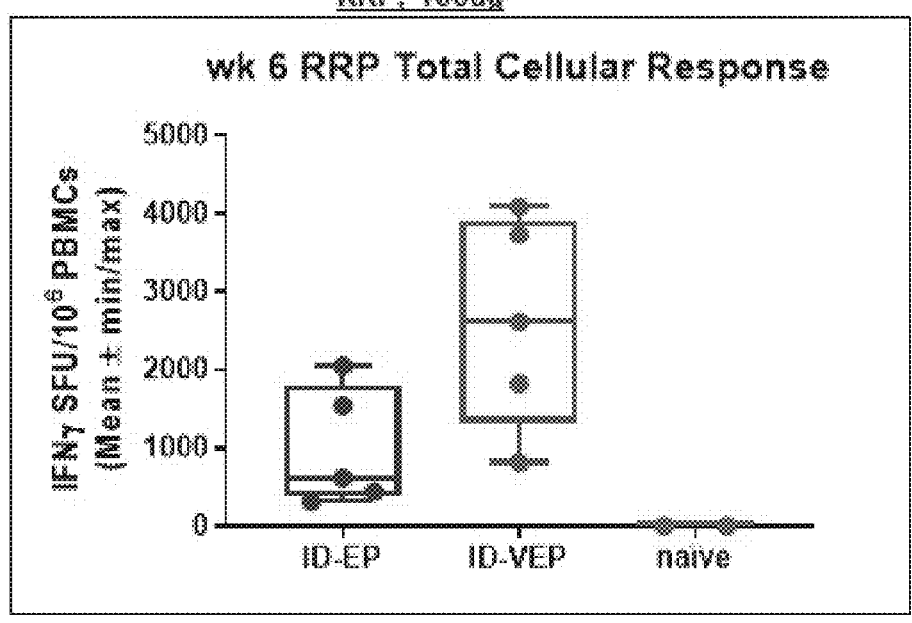
FIG. 38 is a chart showing cellular immune response in terms of spot forming units at Week 6 after treatments with a vaccine against Recurrent Respiratory Papillomatosis (RRP), particularly showing comparative responses following respective electroporation treatments in skin using: (1) a prior art needle-array electroporation device; and (2) a vacuum cup similar to that illustrated in FIG. 2A.

FIG. 38 shows a 6-week study comparing cellular immune response data in guinea pigs after intradermal treatments with 100 μg of a Recurrent Respiratory Papillomatosis (RRP) DNA vaccine via mantoux injection followed by electroporation. The groups represented in FIG. 38 include: (1) "ID-EP" treatment using an intradermal needle-electrode electroporation device; and (2) "ID-VEP"—treatment using a vacuum cup similar to that shown in FIG. 2A.

The studies shown in FIGS. 37B and 38 demonstrate that the vacuum cup generates a substantially equivalent cellular immune response compared to the intradermal needle-electrode electroporation device. Additionally, during the studies shown in FIGS. 37A-38, it was observed that there was no visible tissue damage at the vacuum cup treatment site within 7-10 days following the treatment.

Figure 39A:
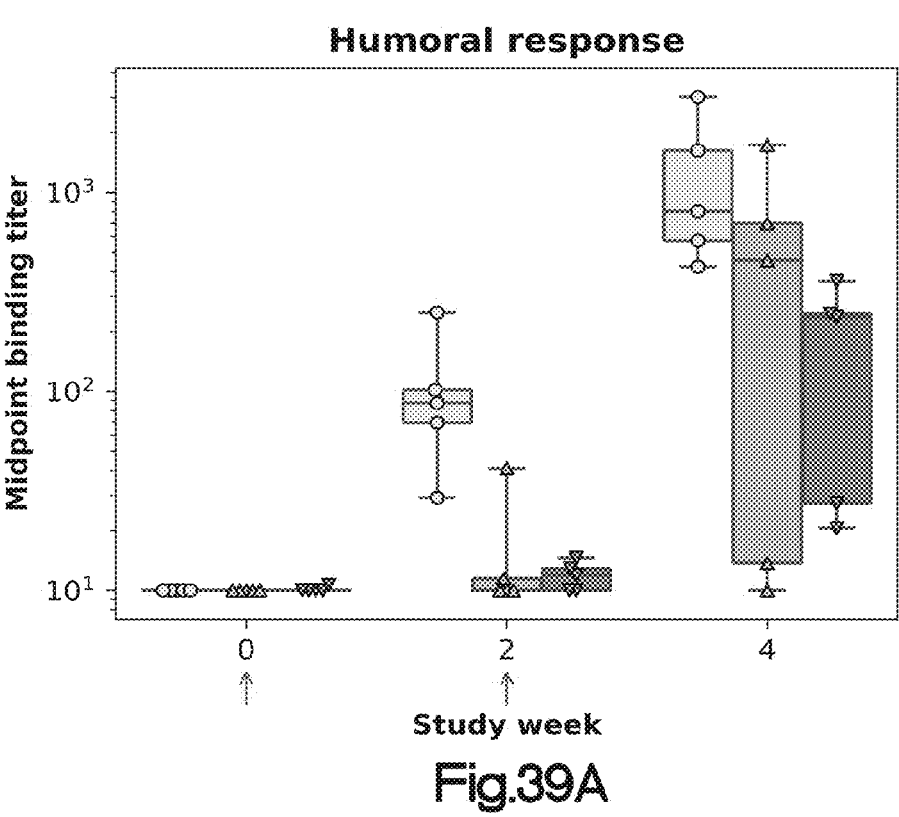
FIG. 39A is a graph showing 4-week humoral immunogenicity data in guinea pigs after treatments with a DNA vaccine against MERS, particularly comparing humoral immune responses following treatments in skin using mantoux injection only, mantoux injection following by vacuum pressure, and mantoux injection following by vacuum pressure and electroporation using vacuum cups similar to that illustrated in FIG. 2A.
Figure 39B:
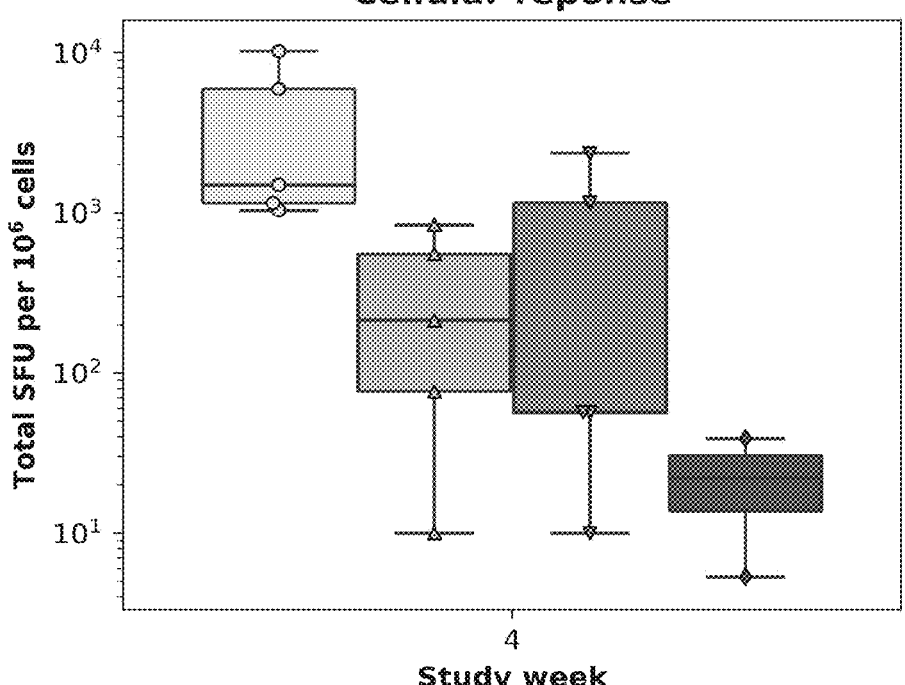
FIG. 39B is a chart showing cellular immune responses from the same study illustrated in FIG. 39A.

Referring now to FIGS. 39A-39B, a 4-week study evaluated the cumulative effects of vacuum pressure and electroporation on immunogenicity in skin. This study compares humoral and cellular immune responses in guinea pigs after intradermal treatments with 50 μg of a MERS DNA vaccine via mantoux injection. FIG. 39A shows humoral immunogenicity ELISA data at weeks 0, 2, and 4 for the following groups: (1) "ID-VEP"-vacuum-assisted electroporation treatments using a vacuum cup similar to that shown in FIG. 2A: (2) "ID-Vacuum"—vacuum-pulsed, non-electroporative treatments using the vacuum cup; and (3) "ID"—mantoux injection only. FIG. 39B shows cellular immune response ELISpot data at week 4 of the same study shown in FIG. 39A. These studies demonstrate that, following the mantoux injection, vacuum pressure alone (i.e., without electroporation) can generate at least a partial humoral response, although electroporation is essential for vacuum pressure to cause immunogenicity. The inventors believe that these studies also suggest that the foregoing immune responses are only partially explained by surface transfection of the DNA vaccine. Further studies confirmed that electroporative voltage is a stronger driver than vacuum pressure for immunogenicity.

Figure 40A:
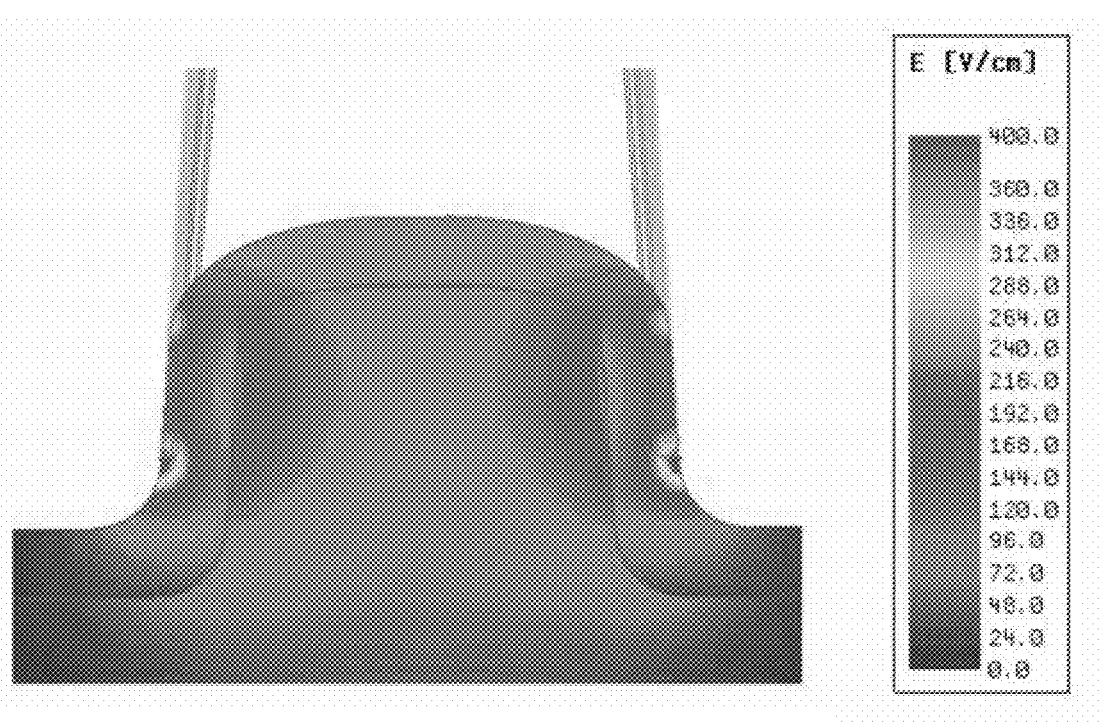
FIG. 40A illustrates a sectional side view of a simulated electrical field created by an electrode array having a pair of opposed electrodes, as generated in a mound of tissue drawn into a vacuum cup configured similar to the vacuum cup shown in FIG. 2A.
Figure 40B:
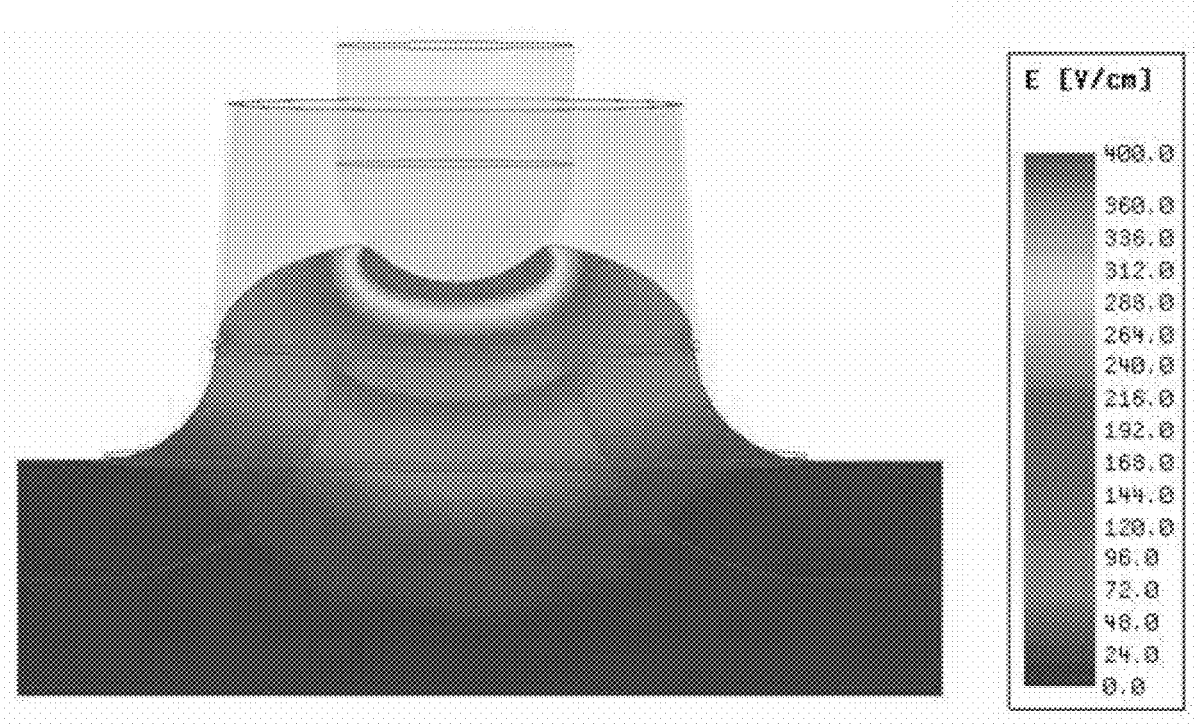
FIG. 40B illustrates a sectional side view of a simulated electrical field created by an electrode array having a pair of annular ring electrodes and a center, concentric electrode, as generated in a mound of tissue drawn into a vacuum cup configured similar to the vacuum cup shown in FIG. 15A.

Referring now to FIGS. 40A-40B, cross-sectional views of comparative electric fields are shown as generated by two different example electrode arrays in a mound of tissue drawn into a vacuum chamber. FIG. 40A shows an electric field generated by an electrode array having a pair of opposed electrodes configured similarly to those of the vacuum cup 2 shown in FIG. 2A. The electroporation pulse delivery pattern (also referred to as the "firing pattern") between the opposed electrodes 8 causes the electrical current to travel between the electrodes laterally across the tissue mound 140. FIG. 40B shows an electric field generated by an electrode array having two annular ring electrodes and a center electrode configured similarly to those of the vacuum cup 1502 shown in FIG. 15A. The electroporation pulse firing pattern in this example causes the electrical current to travel concentrically between the annular ring electrodes and the center electrode, thereby concentrating the electrical field in the skin layer 104 adjacent the center electrode. Thus. FIGS. 40A-40B demonstrate that electroporation pulse firing patterns between opposite electrodes (FIG. 40A) creates an electrical field that is more homogenous through the skin layer 104 compared to the electrical field created between annular ring electrodes and a center electrode (FIG. 40B). These differences in electrical field generation can be employed advantageously based on the particular electroporation treatment desired.

Figure 41A:
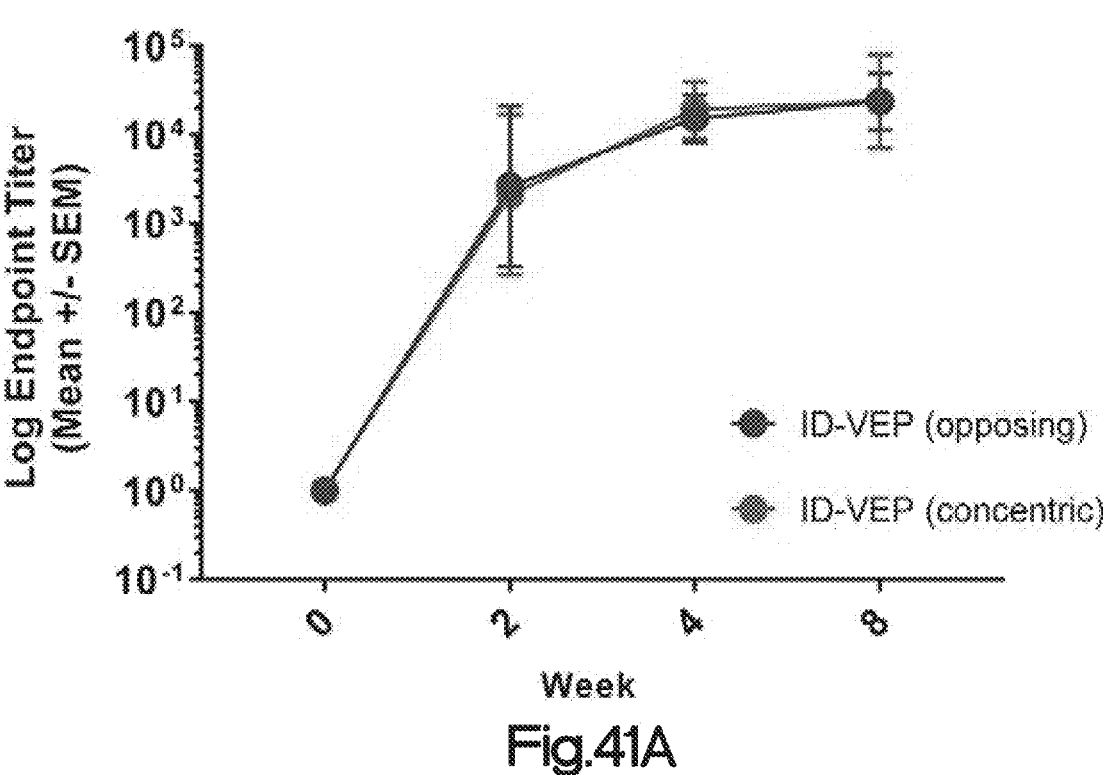
FIG. 41A is a graph showing 8-week humoral immunogenicity data in guinea pigs after treatments with a DNA vaccine against MERS, particularly comparing humoral immune responses following vacuum-assisted electroporation treatments in skin based on electrode pulse patterns using the electrode arrays shown in FIGS. 40A-40B.
Figure 41B:
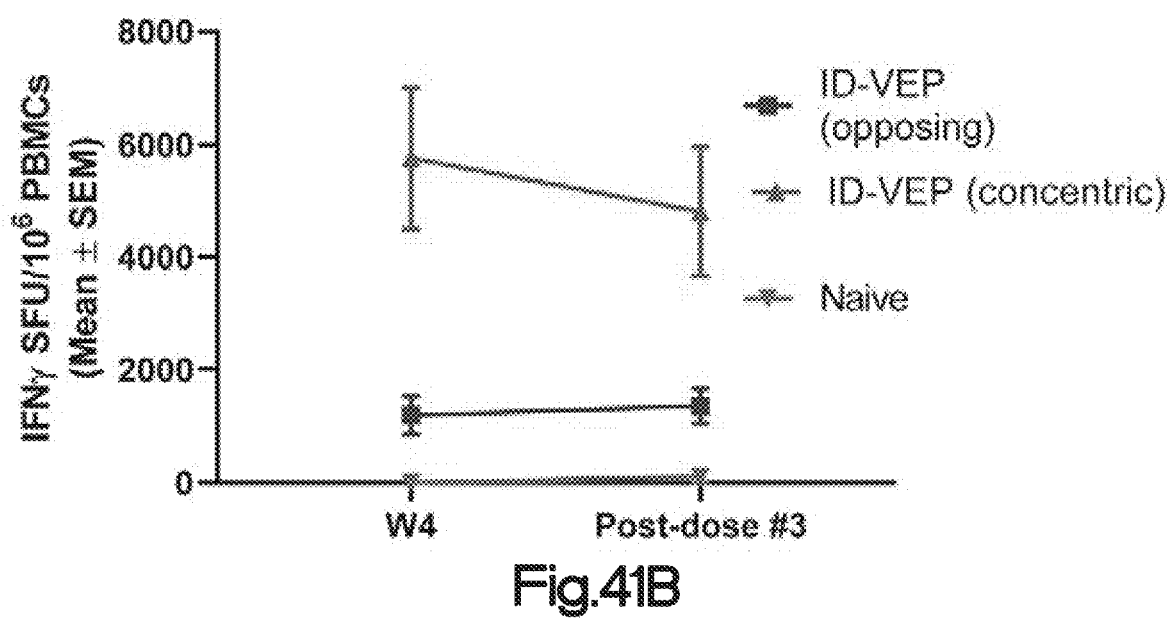
FIG. 41B is a chart showing cellular immune responses from the same study illustrated in FIG. 41A.

Referring now to FIGS. 41A-41B, an 8-week study evaluated the effect of electroporation pulse firing pattern on immunogenicity. In this study, humoral and cellular immune responses in guinea pigs were tested after intradermal treatments of a MERS DNA vaccine via mantoux injection and subsequent vacuum-assisted electroporation using vacuum cups having the electrode arrays shown in FIGS. 40A-40B. FIG. 41A shows humoral immunogenicity ELISA data at weeks 0, 2, 4, and 8 for both array configurations. Both groups were treated at weeks 0, 2, and 4. FIG. 41B charts cellular immune response ELISpot data at week 4 and subsequent to week 4 during the same study shown in FIG. 41A. This study demonstrates that the array configurations performed similarly in terms humoral response, while the concentric array significantly outperformed the opposed array in terms of cellular response.

Figures 42B, 42C, 42D:
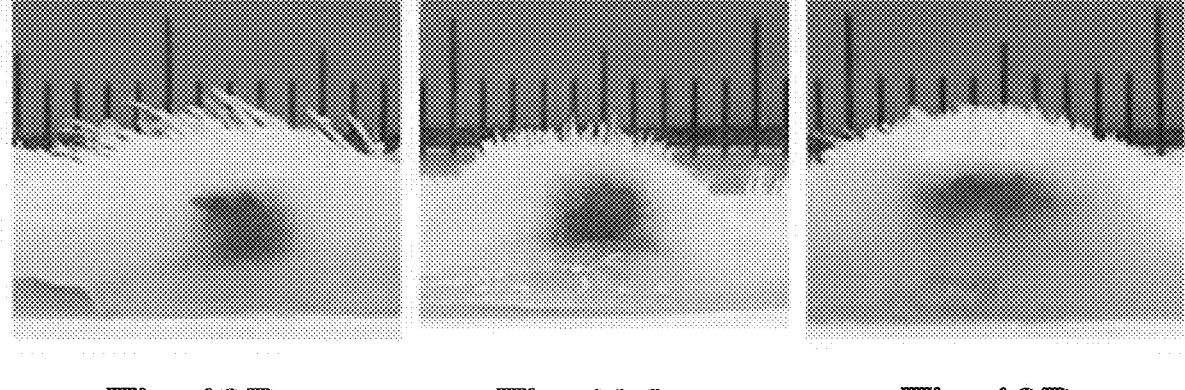
FIGS. 42B-42D are photographs showing the fluid dispersions charted in FIG. 42A.

Referring now to FIGS. 42A-42D, a study evaluated the comparative effect that a center electrode has on fluid dispersion in guinea pig skin. Fluid dispersion of a colored injectate was measured for three groups: (1) mantoux injection only (i.e., no vacuum pressure): (2) an array having opposed electrodes with no center electrode (see FIG. 40A); and (3) an array having a center electrode (see FIG. 40B). Equivalent volumes of an injectate were injected via mantoux injection to each Group. Vacuum pressure was applied to Groups 2 and 3. Electroporation was not performed in this study. FIGS. 42B, 42C, and 42D show the fluid dispersion in the tissue for Groups 1, 2, and 3, respectively. The results were charted in FIG. 42A according to visual aspect ratio of the colored injectate. The results demonstrate that the presence of the center electrode or feature can influence fluid dispersion of the injectate upon application of vacuum pressure. These results further suggest that the internal geometry of the vacuum chamber can influence fluid dispersion upon application of vacuum pressure.

Figure 26:
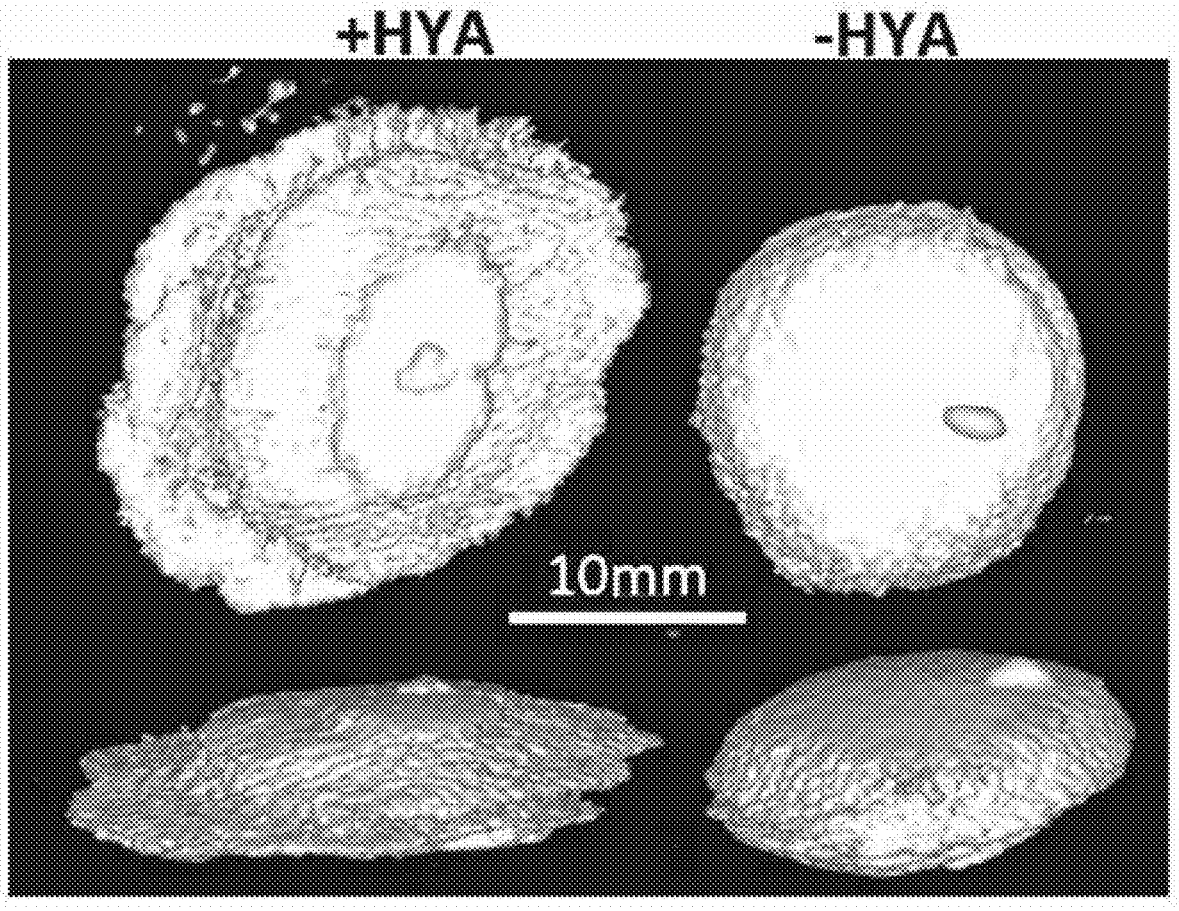
FIG. 26 is a composite image showing top and perspective views of the blebs illustrated in FIG. 25.
Figure 25:
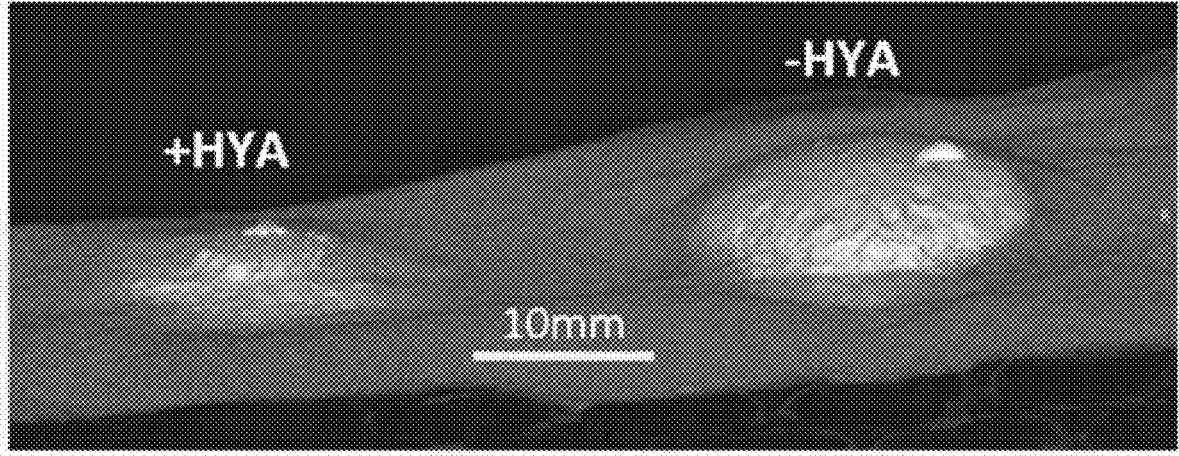
FIG. 25 is a tomography image showing a perspective view of a pair of blebs resulting from prior art mantoux injections; the bleb shown at left contains an agent that was pre-mixed with a hyaluronidase formulation; and the bleb shown at right was injected without a hyaluronidase formulation.

It should be appreciated that the intradermal vacuum-electroporation assemblies, devices, and cups described above can be employed with various formulations for enhancing the vacuum-assisted electroporation treatments. For example, the injectates 142 can include a mixture of the agent with a formulation for affecting a characteristic of the agent in a favorable manner. Non-limiting examples of such formulations include hyaluronidase and Hylenex (human recombinant hyaluronidase), which can temporarily break down the agent matrix, allowing injection at higher agent volumes with smaller, less painful lumps or blebs in the skin. As shown in FIGS. 25-26, mantoux injections including hyaluronidase produce blebs (shown at left) that are smaller, both in height and diameter, than those produced by injections that do not include hyaluronidase. The hyaluronidase formulation is described more fully in U.S. Patent Publication No. 2019/0284263 A1, published Sep. 19, 2019, entitled "In Vivo Use of Chondroitinase and/or Hyaluronidase to Enhance Delivery of an Agent" ("the '263 Reference"), the entire disclosure of which is incorporated by reference herein. By employing hyaluronidase in the injections performed with the vacuum-electroporation devices disclosed herein, the agents can be injected at higher volumes in intradermal tissues, allowing physicians to treat larger tissue volumes with devices herein having larger treatment zones 107. For example, the inventors have discovered, through numerous tests using vacuum cups having various chamber diameters D1 (e.g., 8 mm, 10 mm, and 12 mm) in combination with injectates 142 having a formulation that includes hyaluronidase (i.e., 50% Omnipaque 350+50% 150 U/mL hyaluronidase (final 75 U/mL hyaluronidase)), an 8 mm diameter vacuum cup can accommodate an injectate volume of 0.2 mL with substantially all the injectate pulled into the vacuum chamber; a 10 mm diameter vacuum cup can accommodate an injectate volume of about 0.4 mL with substantially all of the injectate pulled into the vacuum chamber; and a 12 mm diameter vacuum cup can accommodate an injectate volume of 0.8 mL with substantially all the injectate pulled into the vacuum chamber. The presence of hyaluronidase in the injectate formulation was observed to dramatically enhance the fluid dispersion of the injectate within the skin layer. The data from these tests strongly suggests that higher injectate volumes should employ hyaluronidase within the injectate formulation, otherwise the injection bleb is larger and does not spread as favorably laterally through the skin.

Figure 27:
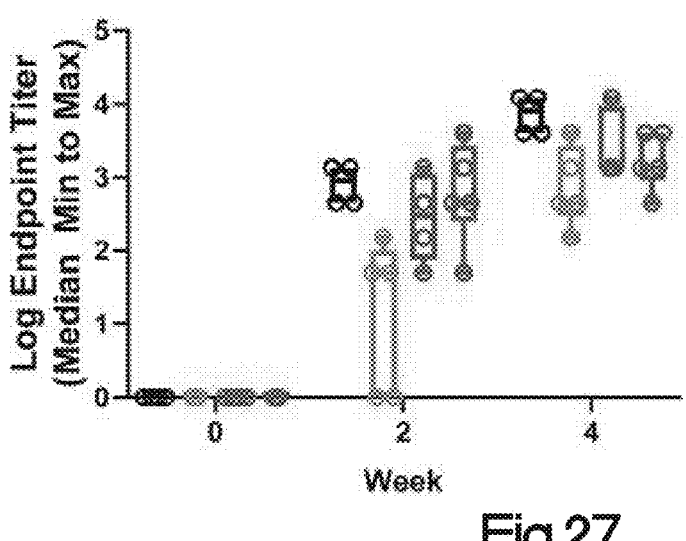
FIG. 27 is a plot showing 4-week humoral immune response data in terms of endpoint titers in guinea pigs after intradermal treatments with a DNA vaccine against MERS (pGX 9101), particularly showing comparative humoral immune responses following respective electroporation treatments in skin using: a prior art needle-array electroporation device, with and without a hyaluronidase formulation; and a version of the vacuum cup illustrated in FIG. 2A having a 15 mm chamber diameter, both with and without a hyaluronidase formulation.

Referring now to FIG. 27, a 4-week study compares humoral immune responses in guinea pigs in terms of endpoint titers after intradermal treatments with a DNA vaccine against MERs (pGX 9101), followed by electroporation. All groups received 50 µg of plasmid in 100 uL mantoux injections in the flank at weeks 0 and 2. The groups represented in the graph are: (1) "ID needle-electrode EP" (black plot)—treatments using the intradermal needle-electrode electroporation device: (2) "ID needle-electrode EP+HYA" (grey plot)—treatments using the intradermal needle-electrode electroporation device as in the previous group, but the formulation included 270 U/mL of intropharma hyaluronidase: (3) "15 mm Vacuum cup" (red plot)—treatments using the vacuum cup 2 shown in FIG. 2A, with a 15 mm chamber diameter D1; (4) the same vacuum cup in the "15 mm Vacuum cup" plot using a formulation that included 270) U/mL of intropharma hyaluronidase.

Figure 28:
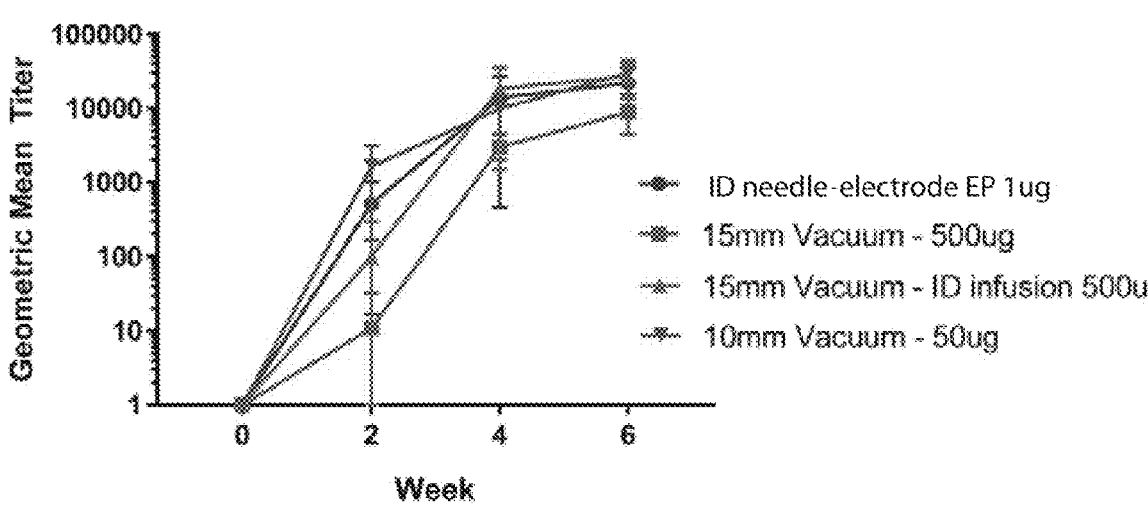
FIG. 28 is a graph showing 6-week humoral immunogenicity data in guinea pigs in terms of endpoint titers after intradermal treatments with a MERS DNA vaccine (pGX 9101), particularly showing comparative humoral immune responses following respective electroporation treatments in skin using: a prior art needle-array electroporation device; and versions of the vacuum cup illustrated in FIG. 2A having 15 mm and 10 mm chamber diameters.

Referring now to FIG. 28, a 6-week study compares humoral immune responses in guinea pigs in terms of endpoint titers after intradermal treatments with a DNA vaccine against MERs (pGX 9101), followed by electroporation at weeks 0, 2, and 4. The groups represented in the graph are: (1) "ID needle-electrode EP" (blue plot)—100 uL injection of 50 µg of plasmid followed by treatment with the intradermal needle-electrode electroporation device; (2) "15 mm Vacuum—500 ug" (red plot)—1 mL mantoux injection of 500 µg of plasmid, where the formulation includes 270 U/mL of Intropharma Hyaluronidase. The electroporation was delivered by the vacuum cup shown in FIG. 2A, with a 15 mm chamber diameter L1; (4) "15 mm Vacuum-ID infusion 500 ug" (green plot)—1 mL deep dermal injection of 500 µg of plasmid but infused over the course of at least 2 minutes, where the formulation includes 270 U/mL of Intropharma Hyaluronidase. The electroporation was delivered by the same vacuum cup 2 as in the preceding group: (4) "10 mm Vacuum—50 ug" (purple plot)—100 uL mantoux injection of 50 µg of plasmid followed by treatment with the vacuum cup 2 shown in FIG. 2A, with a 10 mm chamber diameter L.

Referring now to FIG. 29A, a 6-week study compares humoral immune responses in guinea pigs in terms of mean endpoint titers after intradermal injections of a DNA vaccine against Influenza nucleoprotein (pGX 2013), followed by electroporation at weeks 0, 3 and 6. The groups represented in the graph are: (1) "ID needle-electrode EP lug" (red plot)—treatments via a mantoux injection with 1 ug of plasmid and then electroporation using the intradermal needle-electrode electroporation device: (2) "Vacuum w/HYA 10 ug" (blue plot)—a 1 mL mantoux injection of 10 µg of plasmid in a formulation which included 139.5 U/mL Hylenex was treated with the vacuum cup 2 shown in FIG. 2A, with a 15 mm chamber diameter D1: (3) "Vacuum w/HYA lug" (green plot)—A 100 uL mantoux injection with 1 ug of plasmid which included 139.5 U/mL of Hylenex was then electroporated using the same vacuum cup 2 as in the preceding group: (4) "Vacuum w/o HYA lug" (purple plot)—A 100 uL mantoux injection with 1 ug of plasmid was then electroporated using the same vacuum cup 2 as in groups (2) and (3). FIGS. 29B and 29C show the cellular immune responses in terms of spot forming units at Week 2 (FIG. 29B) and week 4 (FIG. 29C) of the study in FIG. 29A.

Figure 43A:
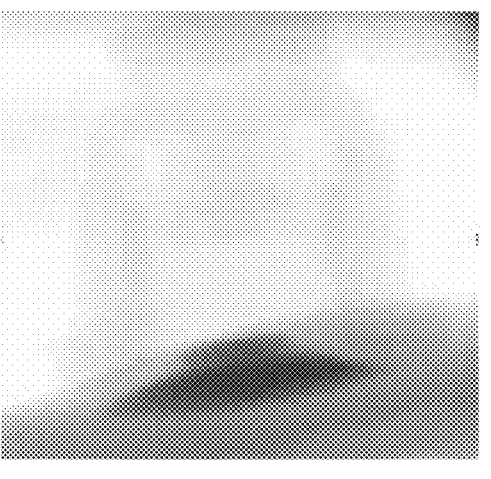
Figure 43B:
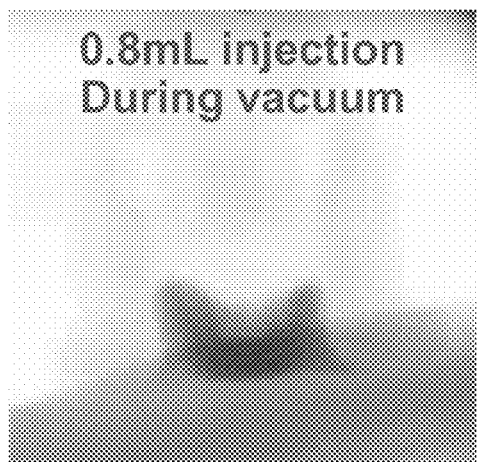
FIG. 43B shows the injectate during application of vacuum pressure in the chamber.
Figure 43C:
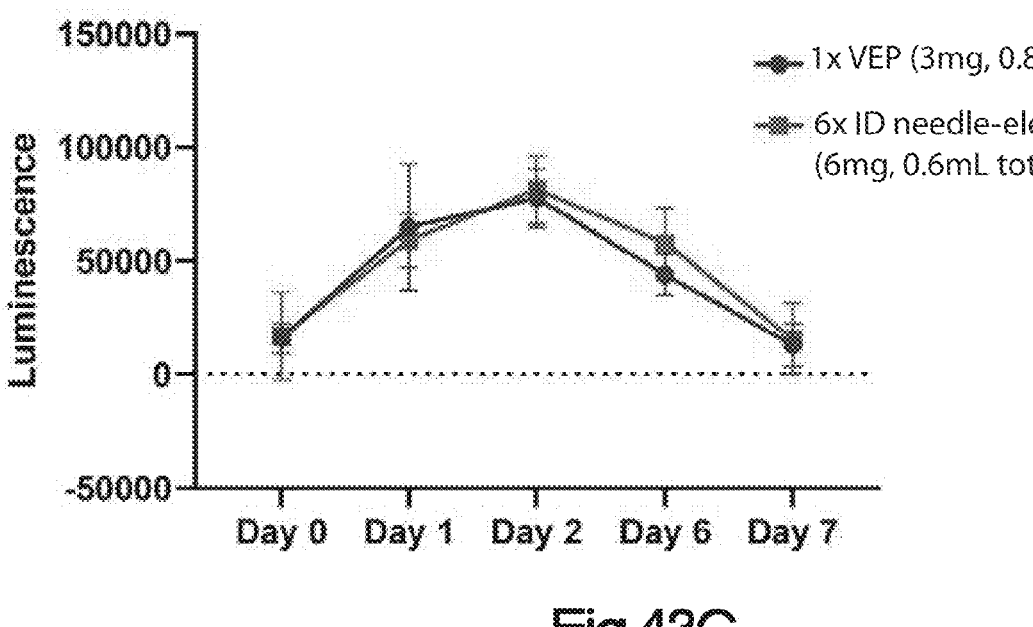
FIG. 43C is a graph showing comparing expressions of secreted alkaline phosphatase (SEAP) following: (1) a single high-injectate volume, vacuum-assisted electroporation treatment using the vacuum cup shown in FIGS. 43A-B; and (2) a six-injection, six-electroporation event treatment using a prior art needle-array electroporation device.

Referring now to FIGS. 43A-43C, a 7-day study evaluated the comparative effect of a single, high-volume injection and vacuum-assisted electroporation treatment versus a multi-injection, multi-electroporation treatment using an intradermal needle-electrode electroporation device in guinea pigs. The single high-volume vacuum-assisted electroporation treatment was performed using a 15 mm diameter vacuum cup having a pair of annular ring electrodes and a center (concentric) electrode, similar to the vacuum cup shown in FIG. 15A. The single injection was a 0.8 mL mantoux injection of plasmid encoding secreted alkaline phosphatase (SEAP) co-formulated with 135 U/mL of hyaluronidase, followed by vacuum-assisted electroporation. The multi-injection, multi-electroporation treatment comprised six (6) individual 0.1 mL mantoux injections each followed by electroporation using intradermal needle electrodes (totaling 0.6 mL of injectate and six (6) applications of electroporation). FIG. 43A shows the vacuum cup positioned over the injectate prior to application of vacuum pressure. FIG. 43B shows the injectate within the vacuum cup during application of vacuum pressure, in which is can be seen that the injectate within the tissue has deformed around the center electrode, thereby concentrating the injectate at the electroporation field (see FIG. 40B). FIG. 43C shows SEAP expression (as a readout for systemic protein production in the subjects) for both treatments at days 0, 1, 2, 6, and 7. This study demonstrates that the single, high-volume, vacuum-assisted electroporation treatment using the vacuum cup performs substantially equivalent to the six-injection, six-electroporation treatment using the needle-electrode device.

These studies demonstrate that vacuum-assisted electroporation using the devices and assemblies of the present disclosure enables high-volume delivery of DNA into skin. Furthermore, hyaluronidase formulations (e.g., Hylenex) enhances immunogenicity following vacuum-assisted electroporation of skin. Moreover, the vacuum cups described herein are adapted to take advantage of the significantly higher injectate volumes in intradermal tissue provided by hyaluronidase formulations, including injectate volumes of 1000 uL (1 mL) or higher. Stated differently, by employing hyaluronidase formulations with the vacuum cups of the present disclosure, the vacuum cups can treat significantly larger volumes of intradermal tissue. Additionally, the devices and assemblies of the present disclosure produce more rapid humoral responses than the intradermal needle-electrode electroporation device and comparable overall humoral immune responses relative to the intradermal needle-electrode electroporation device. Furthermore, these studies demonstrate that cellular response kinetics and magnitude can be enhanced through vacuum-assisted electroporation of intradermal tissue. The inventors have also found that using hyaluronidase formulations with vacuum-assisted electroporation of intradermal tissue effectively allows transfection of dermal layers below the superficial layer.

Figure 44:
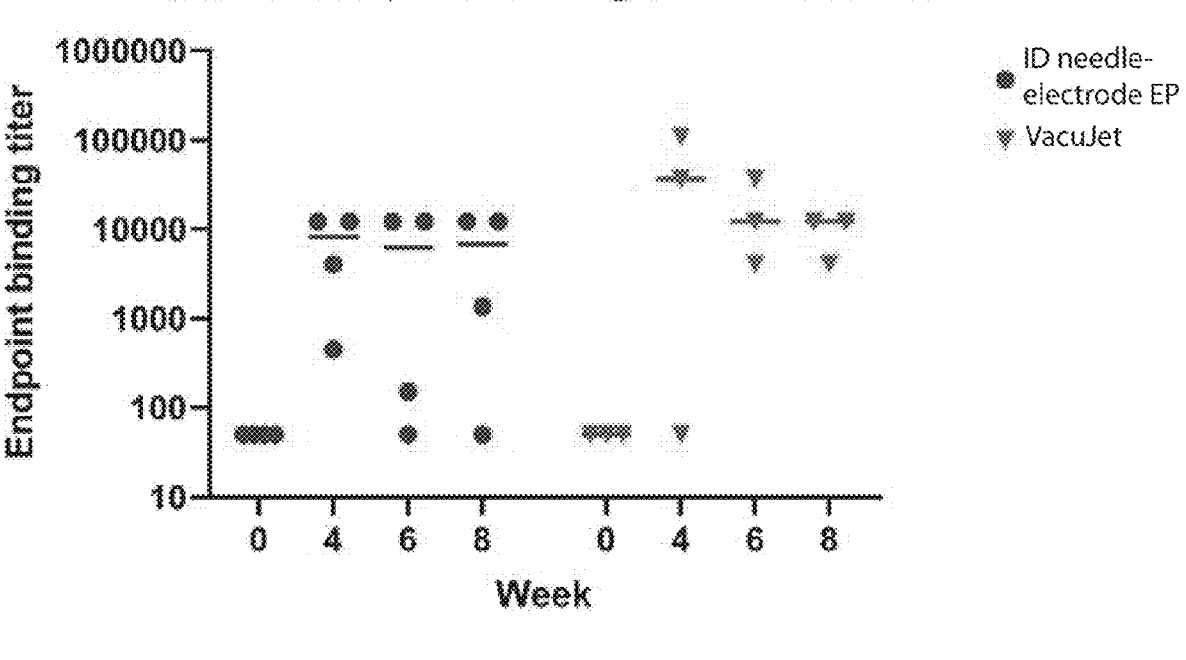
FIG. 44 is a chart showing 8-week humoral immunogenicity ELISA data in guinea pigs after electroporation treatments in skin tissue with pGX 2013, particularly showing comparative humoral immune responses following electroporation treatment with: (1) a jet-injection vacuum cup similar to that illustrated in FIG. 9A; and (2) a prior art needle-array electroporation device.

Referring now to FIG. 44, an 8-week study compares humoral immune responses data effect of electroporation pulse firing pattern on immunogenicity. In this study, humoral and cellular immune responses in guinea pigs were tested after intradermal treatments of a MERS DNA vaccine via mantoux injection and subsequent vacuum-assisted electroporation using vacuum cups having the electrode arrays shown in FIGS. 40A-40B. FIG. 41A shows humoral immunogenicity ELISA data at weeks 0, 2, 4, and 8 for both array configurations. Both groups were treated at weeks 0, 2, and 4. FIG. 41B charts cellular immune response ELISpot data at week 4 and subsequent to week 4 during the same study shown in FIG. 41A. This study demonstrates that the array configurations performed similarly in terms humoral response, while the concentric array significantly outperformed the opposed array in terms of cellular response.

Figures 45A, 45B, 45C, 46A, 46B, 46C, 47A, 47B, 47C:
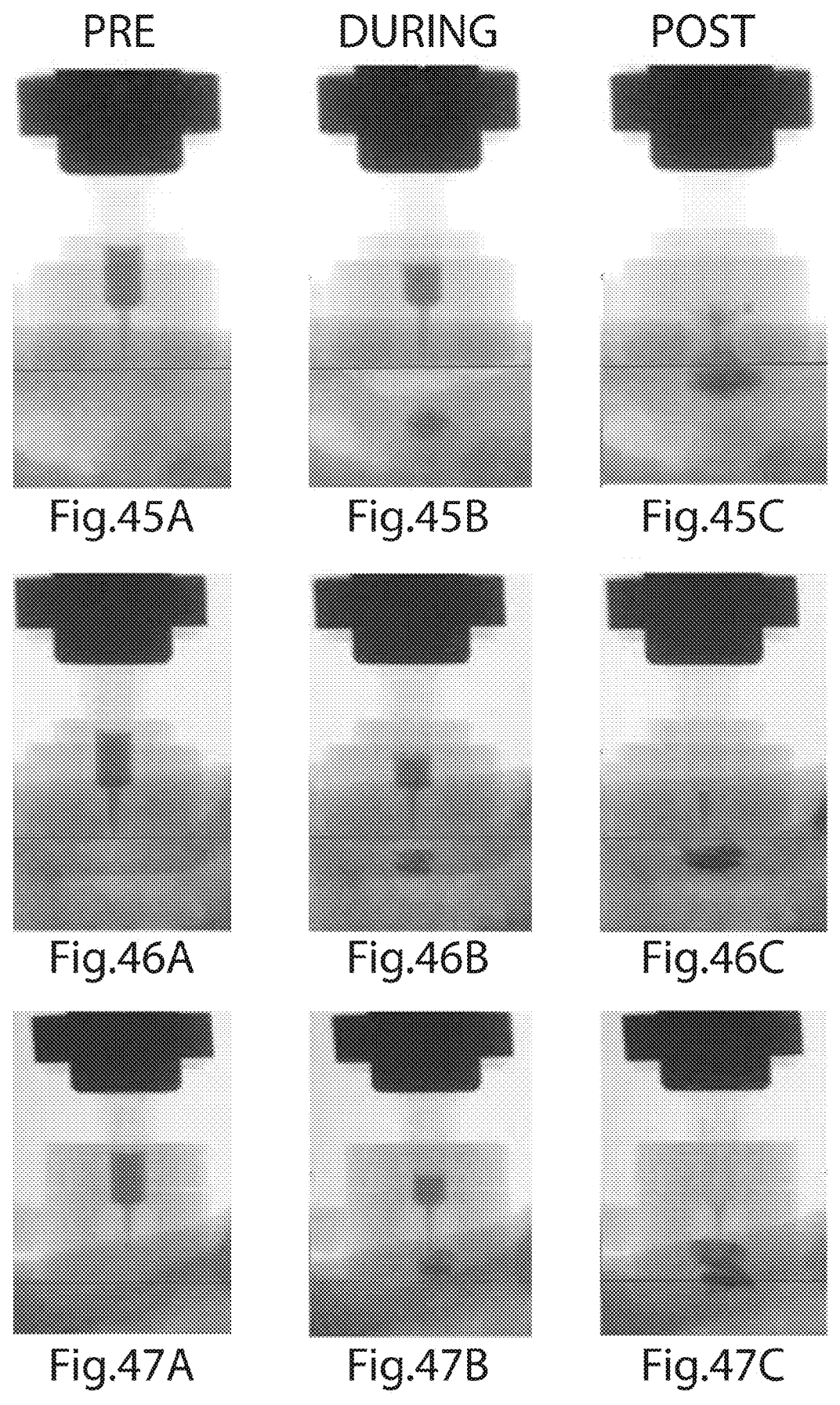

Referring now to FIGS. 45A-47C, fluoroscopic images show comparative tissue deflection in guinea pigs during jet injection at various vacuum pressures and nozzle-to-skin offset distances using a jet-injection vacuum cup configured similar to the vacuum cup 902 shown in FIG. 9. The injectate used in these images is 50% Omnipaque 350 solution to allow radiographic imaging. In each of these images, a superimposed lateral reference line indicates the distal end of the vacuum cup (and thus the distal end of the vacuum chamber and the initial skin-chamber interface prior to vacuum application). FIGS. 45A-45C show jet injection performed without application of vacuum pressure within the chamber. FIGS. 46A-46C show jet injection performed with vacuum pressure applied within the chamber and without a nozzle-to-skin offset distance. FIGS. 47A-47C show jet injection performed with vacuum pressure applied within the chamber and with a nozzle-to-skin offset distance of 3 mm. It should be noted that FIGS. 45A, 46A, and 47A show the tissue pre-injection; FIGS. 45B, 46B, and 47B show the tissue during jet injection; and FIGS. 45C, 46C, and 47C show the tissue post injection.

As shown in FIGS. 45A-45C, without application of vacuum pressure in the chamber, the jet causes significant tissue deflection (FIG. 45B), after which the tissue springs back toward the nozzle post-injection (FIG. 45C), although the injectate resides generally below the vacuum chamber.

As shown in FIGS. 46A-46C, when vacuum pressure is applied within the chamber during injection (FIG. 46B), tissue deflection is eliminated. However, as shown in FIG. 46C, the lack of a nozzle-to-skin offset distance results in the injectate residing below the vacuum chamber post-injection.

Referring now to FIGS. 47A-47C, when the jet injection is performed with a nozzle-to-skin offset distance of 3 mm and while vacuum pressure is applied within the chamber, tissue deflection is substantially eliminated during injection (FIG. 47B). When the skin is pulled into the vacuum chamber prior to injection, as in this study, there is intimate contact between the jet nozzle and the skin during injection, and the vacuum pressure is sufficient to prevent tissue deflection. Moreover, post-injection (FIG. 47C), the injectate resides within the chamber and greater vertical distribution compared to the non-offset setting shown in FIG. 46C, in which the injectate is compressed into a smaller vertical space. These tests demonstrate significant benefits provided by the jet-injection vacuum cups disclosed herein in terms of injectate fluid distribution.

It should be appreciated that although the embodiments described herein are configured to target electroporation in intradermal and/or subcutaneous tissue, any of the design parameters of the vacuum cups 2, 502, 702, 802, 902, 1002, 1502, 1602 and vacuum devices 1802, 1902 can be scaled upward or downward in size to target more specific and/or different tissue layers, such as specific tissue layers within the skin or even muscle layers, such as smooth muscle and skeletal muscle layers. Moreover, the design parameters of the vacuum cups 2, 502, 702, 802, 902, 1002, 1502, 1602 and vacuum devices 1802, 1902 herein can be adapted as needed to target electroporation of other types of tissues, including mucosal membranes, organs, etc.

Although the disclosure has been described in detail, it should be understood that various changes, substitutions, and alterations can be made herein without departing from the spirit and scope of the invention as defined by the appended claims. For example, features of the various embodiments described herein can be incorporated into one or more and up to all of the other embodiments described herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A device for vacuum-assisted in vivo electroporation of tissue, comprising:

a housing defining a chamber, at least one opening into the chamber at a distal end of the housing, an interior surface located within the chamber, and an end surface within the chamber and located opposite the opening;

at least one port extending through the housing, wherein the at least one port is remote from the at least one opening and is connectable to a vacuum source, such that the at least one port is configured to communicate vacuum pressure from the vacuum source to the chamber; and a plurality of electrodes positioned within the chamber, wherein the plurality of electrodes are configured to deliver one or more electroporation pulses to a targeted portion of tissue extending through the at least one opening and at least momentarily held in the chamber responsive to the vacuum pressure, wherein the plurality of electrodes comprises:

a first electrode that extends along the interior surface and is elongate in a circumferential direction along a circumference of the interior surface, wherein the first electrode is spaced from a proximal end of the chamber; and a second electrode that extends from the end surface, wherein the first and second electrodes are concentric with each other.

2. The device of claim 1, wherein the at least one opening is a single opening, and the opening is circular.

3. The device of claim 2, wherein the housing has a wall extending from the end surface to the opening, the wall defining the interior surface, wherein the interior surface at least partially defines the chamber.

4. The device of claim 3, wherein the second electrode is a single electrode centrally positioned with respect to the end surface, and the first electrode extends along an entire circumference of the interior surface.

5. The device of claim 1, wherein the plurality of electrodes have electrode surfaces that are exposed within the chamber, and at least some of the electrode surfaces are one or more of textured and protruding into the chamber.

6. The device of claim 1, wherein the housing is constructed of a material that is flexible, and the material comprises one or more of polycarbonate, polyetheretherketone, polyphthalamide, polyethylene, polytherimide, polyvinyl chloride, polytetrafluoroethylene, polyamide, polyimide, polysiloxane (silicone), polyethylene terephthalate, polyurethane, crosslinked or non-crosslinked rubbers, polyesters.

7. The device of claim 1, further comprising:
a signal generator in electrical communication with the plurality of electrodes and is configured to transmit the one or more electroporation pulses to the plurality of electrodes; and
a processor in electrical communication with the signal generator and at least one sensor positioned in the chamber, the at least one sensor configured to sense at least one parameter of the tissue during delivery of the one or more electroporation pulses and communicate feedback data of the at least one parameter to the processor, and the processor is configured to execute one or more algorithms utilizing the feedback data and adjust at least one pulse parameter of the one or more pulses during delivery of the one or more pulse.

8. The device of claim 1, wherein the plurality of electrodes are configured to apply pulses with potential magnitudes ranging from about 2 V to about 1000 V.

9. The device of claim 1, wherein the plurality of electrodes are configured to apply pulses with current magnitudes ranging from about 0.01 Amps to about 2.0 Amps, the pulses having pulse durations ranging from about 0.1 milliseconds to about 100 milliseconds.

10. The device of claim 1, wherein the targeted portion of the tissue is at least one of skin tissue and adipose tissue.

11. The device of claim 1, wherein:
the plurality of electrodes comprises a third electrode that extends along the interior surface, wherein the third electrode is elongate along the circumferential direction.

12. The device of claim 11, wherein the third electrode is spaced between the first electrode and the at least one opening into the chamber, and the third electrode is concentric with the first electrode.

13. The device of claim 12, wherein the first and third electrodes each extend along an entire circumference of the interior surface.

* * * * *